US011371016B2

(12) United States Patent
Kuwahara et al.

(10) Patent No.: US 11,371,016 B2
(45) Date of Patent: Jun. 28, 2022

(54) METHOD FOR PRODUCING RETINAL TISSUE

(71) Applicants: SUMITOMO PHARMA CO., LTD., Osaka (JP); RIKEN, Wako (JP); SUMITOMO CHEMICAL COMPANY, LIMITED, Tokyo (JP)

(72) Inventors: Atsushi Kuwahara, Kobe (JP); Suguru Yamasaki, Kobe (JP); Yoshiki Sasai, Kobe (JP); Masayo Takahashi, Wako (JP)

(73) Assignees: SUMITOMO PHARMA CO., LTD., Osaka (JP); RIKEN, Wako (JP); SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 16/095,339

(22) PCT Filed: Apr. 21, 2017

(86) PCT No.: PCT/JP2017/016120
§ 371 (c)(1),
(2) Date: Oct. 19, 2018

(87) PCT Pub. No.: WO2017/183732
PCT Pub. Date: Oct. 26, 2017

(65) Prior Publication Data
US 2019/0127690 A1 May 2, 2019

(30) Foreign Application Priority Data
Apr. 22, 2016 (JP) .............................. JP2016-086602

(51) Int. Cl.
A61K 35/30 (2015.01)
C07K 14/71 (2006.01)
(Continued)

(52) U.S. Cl.
CPC ............ *C12N 5/0607* (2013.01); *A61K 35/30* (2013.01); *A61L 27/3804* (2013.01);
(Continued)

(58) Field of Classification Search
None
See application file for complete search history.

(56) References Cited

U.S. PATENT DOCUMENTS 8,287,854 B2 10/2012 Phan
8,956,866 B2 2/2015 Idelson et al.
(Continued)

FOREIGN PATENT DOCUMENTS

CN 1630714 A 6/2005
CN 101330935 A 12/2008
(Continued)

OTHER PUBLICATIONS

Du et al., Invest Ophthalmol Vis Sci. Jul. 2010;51(7):3764-73. doi: 10.1167/iovs.09-4906. Epub Feb. 3, 2010.Regulation of retinal progenitor cell differentiation by bone morphogenetic protein 4 is mediated by the smad/id cascade. (Year: 2010).*
(Continued)

*Primary Examiner* — Aurora M Fontainhas
(74) *Attorney, Agent, or Firm* — Leydig, Voit & Mayer, Ltd.

(57) ABSTRACT

The present invention provides a method for producing a retinal cell or a retinal tissue, including the following steps (1)-(3):
(1) a first step of culturing pluripotent stem cells in the absence of feeder cells in a medium containing 1) a TGFβ family signal transduction pathway inhibiting substance and/or a Sonic hedgehog signal transduction pathway activating substance, and 2) a factor for maintaining undifferentiated state,
(Continued)

(2) a second step of culturing the cells obtained in the first step in suspension in a medium containing a Wnt signal transduction pathway inhibiting substance to form a cell aggregate, and
(3) a third step of culturing the aggregate obtained in the second step in suspension in the presence or absence of a Wnt signal transduction pathway inhibiting substance in a medium containing a BMP signal transduction pathway activating substance to obtain an aggregate containing a retinal cell or a retinal tissue.

22 Claims, 12 Drawing Sheets

(51) Int. Cl.
| | |
|---|---|
| A61P 27/02 | (2006.01) |
| C12N 5/074 | (2010.01) |
| G01N 33/50 | (2006.01) |
| A61L 27/38 | (2006.01) |
| A61L 27/54 | (2006.01) |
| C12N 5/0793 | (2010.01) |
| A61P 27/06 | (2006.01) |
| A61P 9/10 | (2006.01) |
| G01N 33/15 | (2006.01) |

(52) U.S. Cl.
CPC ....... *A61L 27/3834* (2013.01); *A61L 27/3895* (2013.01); *A61L 27/54* (2013.01); *A61P 9/10* (2018.01); *A61P 27/06* (2018.01); *C12N 5/062* (2013.01); *G01N 33/15* (2013.01); *G01N 33/5014* (2013.01); *A61L 2300/414* (2013.01); *A61L 2430/16* (2013.01); *C12N 2501/15* (2013.01); *C12N 2501/155* (2013.01); *C12N 2501/41* (2013.01); *C12N 2501/415* (2013.01); *C12N 2501/727* (2013.01); *C12N 2501/999* (2013.01); *C12N 2506/45* (2013.01); *C12N 2533/52* (2013.01); *G01N 2800/164* (2013.01)

(56) References Cited

U.S. PATENT DOCUMENTS

| | | |
|---|---|---|
| 9,850,465 B2 | 12/2017 | Parent et al. |
| 10,066,209 B2 | 9/2018 | Phan |
| 10,220,117 B2 | 3/2019 | Zhang et al. |
| 10,266,807 B2 | 4/2019 | Rajesh et al. |
| 10,724,000 B2 | 7/2020 | Graf et al. |
| 11,066,645 B2 | 7/2021 | Phan |
| 2003/0059868 A1 | 3/2003 | Greenwood et al. |
| 2003/0180947 A1 | 9/2003 | Wu et al. |
| 2006/0122111 A1 | 6/2006 | Furukawa |
| 2007/0122903 A1 | 5/2007 | Rezania et al. |
| 2008/0044901 A1 | 2/2008 | Sasai et al. |
| 2008/0248005 A1 | 10/2008 | Phan |
| 2009/0053809 A1 | 2/2009 | Zander et al. |
| 2010/0009442 A1 | 1/2010 | Sasai et al. |
| 2010/0119492 A1 | 5/2010 | Hans et al. |
| 2011/0027333 A1 | 2/2011 | Idelson et al. |
| 2011/0091869 A1 | 4/2011 | Sasai et al. |
| 2011/0223140 A1 | 9/2011 | Park et al. |
| 2011/0274662 A1 | 11/2011 | Malcuit et al. |
| 2012/0129211 A1 | 5/2012 | Kattman et al. |
| 2013/0040330 A1 | 2/2013 | Sasai et al. |
| 2014/0308743 A1 | 10/2014 | Sasai et al. |
| 2014/0329321 A1 | 11/2014 | Rajesh et al. |
| 2014/0341864 A1 | 11/2014 | Nakano et al. |
| 2015/0118749 A1 | 4/2015 | Idelson et al. |
| 2015/0125506 A1 | 5/2015 | Idelson et al. |
| 2015/0132787 A1 | 5/2015 | Sasai et al. |
| 2016/0010055 A1 | 1/2016 | Parent et al. |
| 2016/0102292 A1 | 4/2016 | Phan |
| 2016/0186134 A1 | 6/2016 | Keller et al. |
| 2016/0186136 A1 | 6/2016 | Sasai et al. |
| 2016/0237403 A1 | 8/2016 | Sawada et al. |
| 2016/0243285 A1 | 8/2016 | Zhang et al. |
| 2016/0244721 A1 | 8/2016 | Sawada et al. |
| 2016/0251616 A1 | 9/2016 | Nakano et al. |
| 2016/0264936 A1 | 9/2016 | Nakano et al. |
| 2016/0369233 A1 | 12/2016 | Graf et al. |
| 2016/0376554 A1 | 12/2016 | Kuwahara et al. |
| 2017/0067017 A1 | 3/2017 | Meyer et al. |
| 2017/0253853 A1 | 9/2017 | Sasai et al. |
| 2017/0275593 A1 | 9/2017 | Hanna et al. |
| 2017/0313976 A1 | 11/2017 | Kuwahara et al. |
| 2017/0313981 A1 | 11/2017 | Kuwahara et al. |
| 2017/0319748 A1 | 11/2017 | Kuwahara et al. |
| 2018/0119103 A1 | 5/2018 | Phan |
| 2018/0245039 A1 | 8/2018 | Ando et al. |
| 2018/0258388 A1 | 9/2018 | Ando et al. |
| 2020/0206387 A1 | 7/2020 | Takahashi et al. |
| 2020/0208103 A1 | 7/2020 | Sakaguchi et al. |
| 2021/0154370 A1 | 5/2021 | Nukaya et al. |
| 2021/0308188 A1 | 10/2021 | Nakano et al. |

FOREIGN PATENT DOCUMENTS

| | | |
|---|---|---|
| CN | 101688178 A | 3/2010 |
| CN | 102361970 A | 2/2012 |
| CN | 105358680 A | 2/2016 |
| CN | 105814192 A | 7/2016 |
| CN | 105829526 A | 8/2016 |
| CN | 107109367 A | 8/2017 |
| CN | 107326009 A | 11/2017 |
| CN | 108064274 A | 5/2018 |
| CN | 108291206 A | 7/2018 |
| CN | 110945119 A | 3/2020 |
| CN | 111094554 A | 5/2020 |
| CN | 111164205 A | 5/2020 |
| CN | 112601814 A | 4/2021 |
| EP | 2128244 A1 | 12/2009 |
| EP | 2302036 A2 | 3/2011 |
| EP | 3211072 A1 | 8/2017 |
| JP | 2012-507285 A | 3/2012 |
| JP | 2012-070731 A | 4/2012 |
| JP | 2012-245007 A | 12/2012 |
| JP | 2013-099345 A | 5/2013 |
| WO | WO 1995/013364 A1 | 5/1995 |
| WO | WO 2006/053629 A1 | 5/2006 |
| WO | WO 2009/148170 A1 | 12/2009 |
| WO | WO 2010/053472 A1 | 5/2010 |
| WO | WO 2011/043591 A2 | 4/2011 |
| WO | WO 2011/055855 A1 | 5/2011 |
| WO | WO 2012/135621 A2 | 10/2012 |
| WO | WO 2013/065763 A1 | 5/2013 |
| WO | WO 2013/077425 A1 | 5/2013 |
| WO | WO 2014/134213 A1 | 9/2014 |
| WO | WO 2015/011031 A1 | 1/2015 |
| WO | WO 2015/025967 A1 | 2/2015 |
| WO | WO 2015/053375 A1 | 4/2015 |
| WO | WO 2015/054526 A2 | 4/2015 |
| WO | WO 2015/068505 A1 | 5/2015 |
| WO | WO 2015/107738 A1 | 7/2015 |
| WO | WO 2016/032263 A1 | 3/2016 |
| WO | WO 2016/039317 A1 | 3/2016 |
| WO | WO 2016/063985 A1 | 4/2016 |
| WO | WO 2016/063986 A1 | 4/2016 |
| WO | WO 2017/043604 A1 | 3/2017 |
| WO | WO 2017/043605 A1 | 3/2017 |

OTHER PUBLICATIONS

Akopian et al., "Comparison of defined culture systems for feeder cell free propagation of human embryonic stem cells," *In Vitro Cell. Dev. Biol. Anim.*, 46(3-4): 247-258 (2010).

Amoroso et al., "Accelerated High-Yield Generation of Limb-Innervating Motor Neurons from Human Stem Cells," *J. Neurosci.*, 33(2): 574-586 (2013).

(56) References Cited

OTHER PUBLICATIONS

Boucherie et al., "Brief Report: Self-Organizing Neuroepithelium from Human Pluripotent Stem Cells Facilitates Derivation of Photoreceptors," *Stem Cells*, 31(2): 408-414 (2013).
Chambers et al., "Highly efficient neural conversion of human ES and iPS cells by dual inhibition of SMAD signaling," *Nat. Biotechnol.*, 27(3): 275-280 (2009).
Chen, "Chemically defined conditions for human iPSC derivation and culture," *Nat. Methods*, 8(5): 424-429 (2011).
Davis-Dusenbery et al., "How to make spinal motor neurons," *Development*, 141(3): 491-201 (2014).
Denayer et al., "Canonical Wnt Signaling Controls Proliferation of Retinal Stem/Progenitor Cells in Postembryonic Xenopus Eyes," *Stem Cells*, 26(28): 2063-2074 (2008).
Doi et al., "Isolation of Human Induced Pluripotent Stem Cell-Derived Dopaminergic Progenitors by Cell Sorting for Successful Transplantation," *Stem Cell Reports*, 2(3): 337-350 (2014).
Eiraku, "Self-Organized Formation of Polarized Cortical Tissues from ESCs and Its Active Manipulation by Extrinsic Signals," *Cell Stem Cell*, 3(5): 519-532 (2008).
Eiraku et al., "Relaxation-expansion model for self-driven retinal morphogenesis," *Bioessays*, 34(1): 17-25 (2011).
Eiraku et al., "Self-organizing optic-cup morphogenesis in three-dimensional culture," *Nature*, 472(7341): 51-56 (2011).
Faravelli et al., "Motor neuron derivation from human embryonic and induced pluripotent stem cells: experimental approaches and clinical perspectives," *Stem Cell Res. Ther.*, 5(4): 87 (2014).
Fuhrmann, "Wnt signaling in eye organogenesis," *Organogenesis*, 4(2): 60-67 (2008).
Furuta et al., "BMP4 is essential for lens induction in the mouse embryo," *Genes Dev.*, 12(23): 3764-3775 (1998).
Hu et al., "Neural differentiation of human induced pluripotent stem cells follows developmental principles but with variable potency," *Proc. Natl. Acad. Sci. U.S.A.*, 107(9): 4335-4340 (2010).
Ikeda et al., "In vitro neuronal differentiation induction using ES cells—telencephalic precursors and neural retinal precursors," *Experimental Medicine*, 24(2): 188-194 (2006).
Kadoshima et al., "Self-organization of axial polarity, inside-out layer pattern, and species-specific progenitor dynamics in human ES cell-derived neocortex," *Proc. Natl. Acad. Sci. U.S.A.*, 110(50): 20284-20289 (2013).
Kubo et al., "Wnt2b controls retinal cell differentiation at the ciliary marginal zone," *Development*, 130(3): 587-598 (2003).
Kubo et al., "Hairy1 acts as a node downstream of Wnt signaling to maintain retinal stem cell-like progenitor cells in the chick ciliary marginal zone," *Development*, 136(11): 1823-1833 (2009).
Kuwahara et al., "Generation of a ciliary margin-like stem cell niche from self-organizing human retinal tissue," *Nat. Common.*, 6: 6286 (2015).
Lamba et al., "Efficient generation of retinal progenitor cells from human embryonic stem cells," *Pro Natl., Acad. Sci. U.S.A.*, 103(34): 12769-12774 (2006).
Lancaster et al., "Cerebral organoids model human brain development and microcephaly," *Nature*, 501(7467): 373-379 (2013).
Lang, "Pathways regulating lens induction in the mouse," *Int. J. Dev. Biol.*, 48(8-9): 783-791 (2004).
La Torre et al., "Production and Transplantation of Retinal Cells from Human and Mouse Embryonic Stem Cells," *Retinal Development: Methods and Protocols, Methods in Molecolar Biology*, 884: 229-246 (2012).
Messina et al., "Noggin-Mediated Retinal Induction Reveals a Novel Interplay Between Bone Morphogenetic Protein Inhibition, Transforming Growth Factor β, and Sonic Hedgehog Signaling," *Stem Cells*, 33(8): 2496-2508 (2015).
Morizane et al., "Neural Induction with a Dopaminergic Phenotype from Human Pluripotent Stem Cells Through a Feeder-Free Floating Aggregation Culture," *Methods Mol. Biol.*, 1018: 11-19 (2013).
Muguruma et al., "Ontogeny-recapitulating generation and tissue integration of ES cell-derived Purkinje cells," *Nat. Neorosci.*, 13(10): 1171-1180 (2010).

Nakagawa et al., "A novel efficient feeder-free culture system for the derivation of human induced pluripotent stem cells," *Sci. Rep.*, 4: 3594 (2014).
Nakano et al., "Self-Formation of Optic Cups and Storable Stratified Neural Retina from Human ESCs," *Cell Stem Cell*, 10(6): 771-785 (2012).
Osakada et al., "Control of neural differentiation from pluripotent stem cells," *Inflammation and Regeneration*, 28(3): 166-173 (2008).
Osakada et al., "Toward the generation of rod and con photoreceptors from mouse, monkey and human embryonic stem cells," *Nat. Biotechnol.*, 26(2): 215-224 (2008).
Osakada et al., "In vitro differentiation of retinal cells from human pluripotent stem cells by small-molecule induction," *J. Cell Sci.*, 122(17): 3169-3179 (2009).
Osakada et al., "Neural Induction and Patterning in Mammalian Pluripotent Stem Cells," *CNS & Neurological Disorders—Drug Targets*, 10(4): 419-432 (2011).
Ozair, "Neural induction and early patterning in vertebrates," *WIREs Dev. Biol.*, 2(4): 479-498 (2013).
Sasai, "Self-organization as seen in pattern formation of neural tissue: Challenge to Emergent Biology," *Brain Science Review*, 99-112 (2014).
Seiler et al., "Visual restoration and transplant connectivity in degenerate rats implanted with retinal progenitor sheets," *Eur. J. Neurosci.*, 31: 508-520 (2010).
Stephens et al., "Loss of adenomatous polyposis *coli* (apc) Results in an Expanded Ciliary Marginal Zone in the Zebrafish Eye," *Dev. Dyn.*, 239(7): 2066-2077 (2010).
Suga et al., "Self-formation of functional adenohypophysis in three-dimensional culture," *Nature*, 480(7375): 57-62 (2011).
Trousse et al., "BMP4 Mediates Apoptotic Cell Death in the Developing Chick Eye," *J. Neurosci.*, 21(4): 1292-1301 (2001).
Vugler et al., "Embryonic stem cells and retinal repair," *Mech. Dev.*, 124(11-12): 807-829 (2007).
Watanabe et al., "Directed differentiation of telencephalic precursors from embryonic stem cells," *Nat. Neurosci.*, 8(3): 288-296 (2005).
Wei et al., "Isolation and identification of retinal stem cells in mouse eye," *Journal of Third Military Medical University*, 25(24): 2161-2164 (2003).
Yang et al., "Directed Differentiation into Neural Lineages and Therapeutic Potential of Porcine Embryonic Stem Cells in Rat Parkinson's Disease Model," *Cell Reprogram.*, 12(4): 447-461 (2010).
Yang et al., "Efficient generation of lens progenitor cells and lentoid bodies from human embryonic stem cells in chemically defined conditions," *FASEB J.*, 24(9): 3274-3283 (2017).
Zhou et al., "Differentiation of human embryonic stem cells into cone photoreceptors through simultaneous inhibition of BMP, TGFβ and Wnt signaling," *Development*, 142(19): 3294-3306 (2015).
European Patent Office, Communication Pursuant to Rule 164(1) EPC in European Patent Application No. 15852504.8 (dated May 14, 2018).
European Patent Office, Extended European Search Report in European Patent Application No. 15852504.8 (dated Sep. 6, 2018).
Japanese Patent Office, International Search Report in International Patent Application No. PCT/JP2017/016120 (dated Jul. 11, 2017).
European Patent Office, Extended European Search Report in European Patent Application No. 17786064.0 (dated Oct. 17, 2019).
Loebel et al., "Lineage choice and differentiation in mouse embryos and embryonic stem cells," *Dev. Biol.*, 264(1): 1-14 (2003).
Miyazawa et al., "Two major Smad pathways in TGF-β superfamily signaling," *Genes to Cell*, 7(12): 1191-1204 (2002).
Stanton et al., "Small-molecule modulators of the Sonic Hedgehog signaling pathway," *Mol. BioSyst.*, 6(1): 44-54 (2010).
European Patent Office, Supplementary European Search Report in European Patent Application No. 15852025 (dated Apr. 20, 2018).
Shafaie et al., "In Vitro Cell Models for Ophthalmic Drug Development Applications," *BioRes. Open Access*, 5(1): 94-108 (2016).
Zacharias et al., "In Vitro Evidence for Mycophenolic Acid Dose-Related Cytotoxicity in Human Retinal Cells," *Retina*, 33(10): 2155-2161 (2013).
U.S. Appl. No. 15/521,334, filed Apr. 24, 2017.

(56) References Cited

OTHER PUBLICATIONS

U.S. Appl. No. 15/521,387, filed Apr. 24, 2017.
Zhang et al., "Rapid and Efficient Generation of Neurons from Human Pluripotent Stem Cells in a Multititre Plate Format," *J. Vis. Exp.*, 73: e4335 (2013).
European Patent Office, Extended European Search Report in European Patent Application No. 21166628.4 (dated Jul. 19, 2021).

* cited by examiner

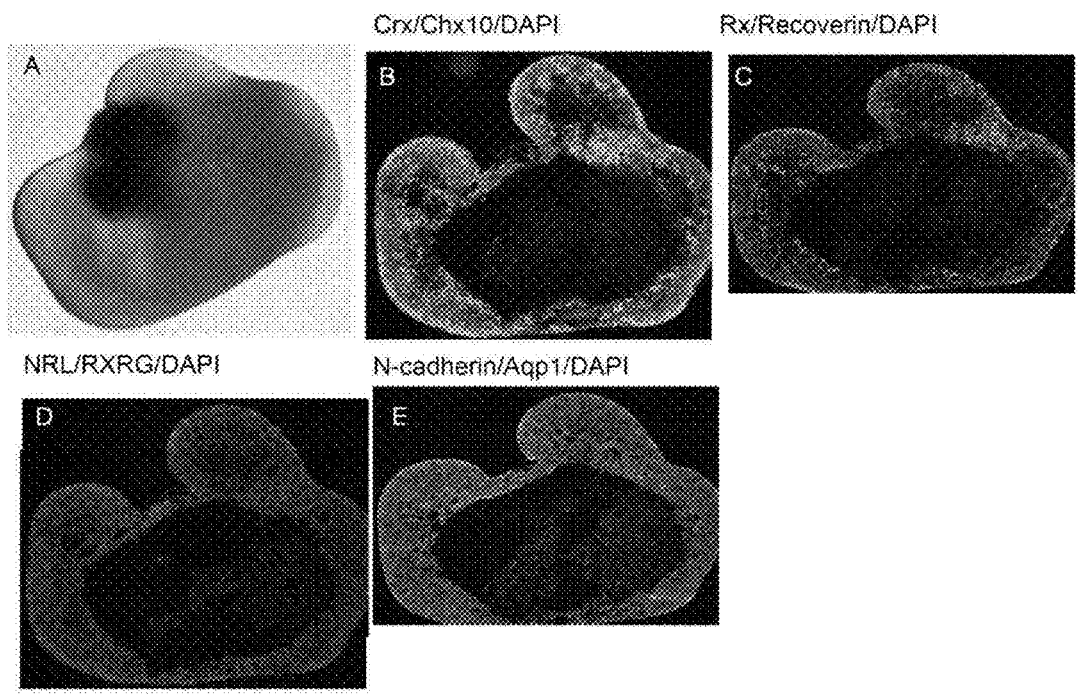

METHOD FOR PRODUCING RETINAL TISSUE

CROSS-REFERENCE TO RELATED APPLICATIONS

This patent application is the U.S. national phase of International Patent Application No. PCT/JP2017/016120, filed Apr. 21, 2017, which claims the benefit of Japanese Patent Application No. 2016-086602, filed on Apr. 22, 2016, which are incorporated by reference in their entireties herein.

TECHNICAL FIELD

The present invention relates to a method for producing retinal cells or a retinal tissue from pluripotent stem cells.

BACKGROUND ART

As a method for producing a neural tissue such as a retinal tissue from pluripotent stem cells, a method for producing a neural tissue which comprises forming uniformed aggregates of pluripotent stem cells in a serum-free medium, culturing them in suspension, culturing them in suspension in a medium for differentiation induction in the presence of a differentiation-inducing factor and the like as appropriate to induce differentiation of pluripotent stem cells into the intended neural cells has been reported (patent document 1 and non-patent document 1). For example, a method for obtaining a multi-layered retinal tissue from pluripotent stem cells (non-patent document 2 and patent document 2), and a method for obtaining a multi-layered retinal tissue which comprises forming uniformed aggregates of pluripotent stem cells in a serum-free medium containing a Wnt signal transduction pathway inhibiting substance, followed by culturing them in suspension in the presence of a basement membrane preparation, and then culturing them in suspension in a serum-containing medium (non-patent document 3 and patent document 3), and a method for obtaining a retinal tissue by culturing an aggregate of pluripotent stem cells in suspension in a medium containing a BMP signal transduction pathway activating substance (patent document 5 and non-patent document 10) are known. In addition, a method for inducing differentiation of pluripotent stem cells into a hypothalamic tissue (patent document 4 and non-patent document 4), and a method inducing differentiation of pluripotent stem cells into neural progenitor cells (non-patent document 5 and 6) have also been reported.

The pluripotent stem cells as a starting material of these production methods, particularly in the case of primate pluripotent stem cells, could be cultured while maintaining an undifferentiated state in the presence of feeder cells and with the addition of a factor for maintaining undifferentiated state. In recent years, improvement has been made in the culture to maintain undifferentiated state, and a method of culturing primate pluripotent stem cells in the absence of feeder cells (feeder-free) with the addition of a factor for maintaining undifferentiated state has been reported (non-patent documents 7, 8 and 9). A method for stably producing neural cells or a neural tissue such as retina and the like, which uses pluripotent stem cells subjected to feeder-free culture by this method as a starting material has been desired.

DOCUMENT LIST

Patent Documents patent document 1: WO 2009/148170
patent document 2: WO 2011/055855
patent document 3: WO 2013/077425
patent document 4: WO 2013/065763
patent document 5: WO 2015/025967

Non-Patent Documents non-patent document 1: Cell Stem Cell, 3, 519-32 (2008)
non-patent document 2: Nature, 472, 51-56 (2011)
non-patent document 3: Cell Stem Cell, 10(6), 771-775 (2012)
non-patent document 4: Nature, 480, 57-62 (2011)
non-patent document 5: Nature Biotechnology, 27(3), 275-80 (2009)
non-patent document 6: Proc Natl Acad Sci USA, 110(50), 20284-9 (2013)
non-patent document 7: Nature Methods, 8, 424-429 (2011)
non-patent document 8: Scientific Reports, 4, 3594 (2014)
non-patent document 9: In Vitro Cell Dev Biol Anim., 46, 247-58 (2010)
non-patent document 10: Nature Communications, 6, 6286 (2015)

SUMMARY OF INVENTION

Technical Problem

The problem to be solved by the present invention is provision of a method for producing retinal cells or a retinal tissue from pluripotent stem cells cultured while maintaining an undifferentiated state in the absence of feeder cells.

Solution to Problem

The present inventors have conducted intensive studies in an attempt to solve the aforementioned problems and found that a cell aggregate maintaining an undifferentiated state can be formed with high efficiency by culturing pluripotent stem cells in the absence of feeder cells (under feeder-free conditions) in a medium containing a TGFβ family signal transduction pathway inhibiting substance and/or a Sonic hedgehog signal transduction pathway activating substance, and then culturing them in suspension in a medium containing a Wnt signal transduction pathway inhibiting substance. In addition, the present inventors have found that neural tissues such as a retinal tissue and the like and neural cells can be induced with high efficiency by using this high quality cell aggregate, which resulted in the completion of the present invention.

That is, the present invention relates to the following.
[1] A method for producing a retinal cell or a retinal tissue, comprising the following steps (1)-(3):
(1) a first step of culturing pluripotent stem cells in the absence of feeder cells in a medium containing 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension in a medium containing a Wnt signal transduction pathway inhibiting substance to form a cell aggregate, and
(3) a third step of culturing the aggregate obtained in the second step in suspension in the presence or absence of a Wnt signal transduction pathway inhibiting substance in a medium containing a BMP signal transduction pathway activating substance to obtain an aggregate containing a retinal cell or a retinal tissue.

[2] The production method of [1], wherein the pluripotent stem cells are cultured for 0.5 hr-144 hr in the first step.
[3] The production method of [1] or [2], wherein the culturing in the first step is performed by adhesion culture.
[4] The production method of any of [1] to [3], wherein, in the second step, the cells obtained in the first step are dispersed, and the dispersed cells are cultured in suspension.
[5] The production method of any of [1] to [4], wherein the factor for maintaining undifferentiated state comprises at least an FGF signal transduction pathway activating substance.
[6] The production method of [5], wherein the FGF signal transduction pathway activating substance is bFGF.
[7] The production method of any of [1] to [6], wherein the medium used for suspension culture in the second step further comprises a Sonic hedgehog signal transduction pathway activating substance.
[8] The production method of [7], wherein the pluripotent stem cells are human pluripotent stem cells and, in the second step, the concentration of the Sonic hedgehog signal transduction pathway activating substance in the medium is a concentration corresponding to Sonic hedgehog signal transduction activity of SAG at 10 nM to 700 nM.
[9] The production method of any of [1] to [8], wherein the TGFβ family signal transduction pathway inhibiting substance is a TGFβ signal transduction pathway inhibiting substance or a BMP signal transduction pathway inhibiting substance.
[10] The production method of any of [1] to [9], wherein the TGFβ family signal transduction pathway inhibiting substance is one or more substances selected from the group consisting of Lefty, SB431542, A-83-01 and LDN193189.
[11] The production method of any of [1] to [10], wherein the Sonic hedgehog signal transduction pathway activating substance is one or more substances selected from the group consisting of Shh, SAG and Purmorphamine.
[12] The production method of any of [1] to [11], wherein, in the third step, the BMP signal transduction pathway activating substance is added to the medium between day 1 and day 9 from the start of the second step.
[13] The production method of [12], wherein, in the third step, the BMP signal transduction pathway activating substance is added to the medium between day 1 and day 6 from the start of the second step.
[14] The production method of [13], wherein, in the third step, the BMP signal transduction pathway activating substance is added to the medium between day 1 and day 3 from the start of the second step.
[15] The production method of any of [1] to [14], wherein the BMP signal transduction pathway activating substance is one or more proteins selected from the group consisting of BMP2, BMP4, BMP7 and GDF7.
[16] The production method of any of [1] to [15], wherein the BMP signal transduction pathway activating substance is BMP4.
[17] The production method of any of [1] to [16], wherein, in the third step, the aggregate is cultured in a medium containing a Sonic hedgehog signal transduction pathway activating substance at a concentration not more than a concentration corresponding to Sonic hedgehog signal transduction activity of SAG at 700 nM.
[18] The production method of any of [1] to [16], wherein, in the third step, the concentration of the Sonic hedgehog signal transduction pathway activating substance in the medium is not more than a concentration corresponding to Sonic hedgehog signal transduction activity of SAG at 700 nM.
[19] The production method of any of [1] to [18], wherein the culturing is performed in a medium containing a Wnt signal transduction pathway inhibiting substance for 3 days to for 18 days from the start of the second step.
[20] The production method of any of [1] to [19], wherein the culturing is performed in a medium containing a Wnt signal transduction pathway inhibiting substance for 10 days from the start of the second step.
[21] The production method of any of [1] to [20], wherein the Wnt signal transduction pathway inhibiting substance is IWR-1-endo.
[22] The production method of any of [1] to [21], wherein the third step comprises the following steps:
(i) a step of culturing the aggregate obtained in the second step in suspension in the presence or absence of a Wnt signal transduction pathway inhibiting substance in a medium containing a BMP signal transduction pathway activating substance to obtain a cell aggregate containing a retinal cell or a retinal tissue and having an existence ratio of Chx10 positive cells of not less than 20% and not more than 100%;
(ii) a step of culturing the cell aggregate obtained in step (i) in a serum-free medium or serum-containing medium containing a Wnt signal transduction pathway activating substance and/or an FGF signal transduction pathway inhibiting substance for only a period before the appearance of a cell expressing RPE65 gene;
(iii) a step of culturing the cell aggregate obtained in step (ii), in which the RPE65 gene-expressing cell does not appear, in a serum-free medium or a serum-containing medium without a Wnt signal transduction pathway activating substance.
[23] The production method of any of [1] to [22], wherein the aggregate obtained in the third step comprises one or more cells selected from the group consisting of retinal progenitor cell, neural retinal progenitor cell, photoreceptor precursor cell, photoreceptor cell, rod photoreceptor cell, cone photoreceptor cell, horizontal cell, amacrine cell, interneuron, ganglion cell, bipolar cell, retinal pigment epithelial cell, and ciliary marginal zone cell.
[24] The production method of any of [1] to [23], wherein the pluripotent stem cells are human pluripotent stem cells.
[25] The production method of any of [1] to [24], wherein the pluripotent stem cells are induced pluripotent stem cells.
[26] The production method of any of [1] to [25], wherein a uniformed aggregate is formed in the second step.
[27] The production method of any of [1] to [26], wherein the suspension culture is performed in the absence of a basement membrane preparation.
[28] A reagent for evaluating toxicity or efficacy of a test substance, comprising a retinal cell or a retinal tissue produced by the method of any of [1] to [27].
[29] A method for evaluating toxicity or efficacy of a test substance, comprising bringing the substance into contact with a retinal cell or a retinal tissue produced by the method of any of [1] to [27], and detecting an influence of the substance on the cell or tissue.
[30] A medicament for treating a disease due to a disorder of a retinal cell or a retinal tissue, comprising a retinal cell or a retinal tissue produced by the method of any of [1] to [27].
[31] The medicament of [30], wherein the retinal cell or retinal tissue is a retinal progenitor cell, a retinal layer-specific neural cell or a retinal tissue.
[32] A method for treating a disease due to a disorder of a retinal cell or a retinal tissue, comprising transplanting an effective amount of a retinal cell or a retinal tissue produced by the method of any of [1] to [27] to a subject in need of the transplantation.

[33] A retinal cell or a retinal tissue produced by the method of any of [1] to [27] for use in the treatment of a disease due to a disorder of a retinal cell or a retinal tissue.
[34] A pharmaceutical composition comprising a retinal cell or a retinal tissue produced by the method of any of [1] to [27] as an active ingredient.

Advantageous Effects of Invention

According to the present invention, a high quality cell aggregate, as well as retinal cells or retinal tissues can be produced with high efficiency from pluripotent stem cells cultured in the absence of feeder cells.

BRIEF DESCRIPTION OF DRAWINGS

FIG. 15 shows bright field observation results of a photoreceptor cell-containing retinal tissue induced from human iPS cells (A). Observation results (B-E) of expression of Crx, Chx10, Rx, Recoverin, NRL, RXRG, N-cadherin and Aqp1 in the photoreceptor cell-containing retinal tissue by immunohistostaining are shown. Counterstained with DAPI (B-E).
FIG. 16 shows the comparison results of expression of Chx10 in cell aggregates formed from human iPS cells under various culture conditions by immunohistostaining.

DESCRIPTION OF EMBODIMENTS

1. Definition

Figure 1:
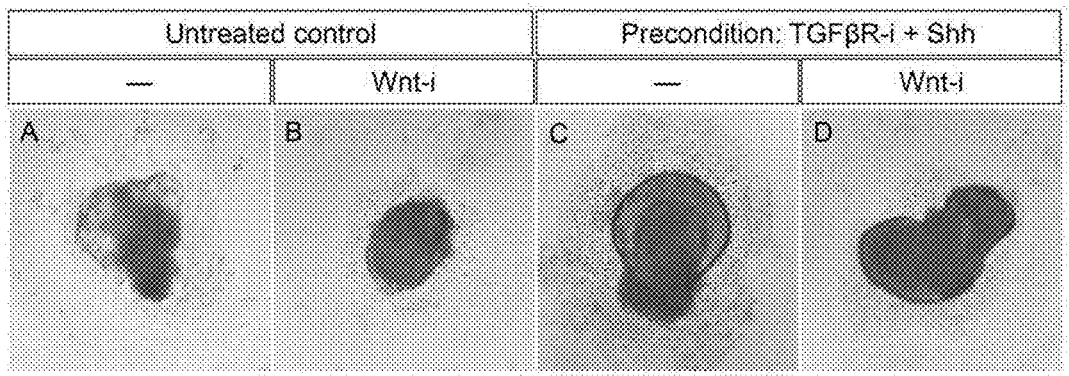
FIG. 1 shows the comparison results of morphology of cell aggregates by bright field observation between the conditions of with (C, D) or without (A, B) Precondition.

In the present invention, "stem cell" means an undifferentiated cell having differentiation potency and proliferative capacity (particularly self-renewal competence) maintaining differentiation potency. The stem cell includes subpopulations such as pluripotent stem cell, multipotent stem cell, unipotent stem cell and the like according to the differentiation potency. Pluripotent stem cell refers to a stem cell capable of being cultured in vitro and having a potency to differentiate into any cell lineage belonging to three germ layers (ectoderm, mesoderm, endoderm) and/or extraembryonic tissues (pluripotency). The multipotent stem cell means a stem cell having a potency to differentiate into plural types of tissues or cells, though not all kinds. The unipotent stem cell means a stem cell having a potency to differentiate into a particular tissue or cell.

Pluripotent stem cell can be induced from fertilized egg, clone embryo, germ stem cell, stem cell in a tissue, somatic cell and the like. Examples of the pluripotent stem cell include embryonic stem cell (ES cell), EG cell (embryonic germ cell), induced pluripotent stem cell (iPS cell) and the like. Muse cell (Multi-lineage differentiating stress enduring cell) obtained from mesenchymal stem cell (MSC), and GS cell produced from reproductive cell (e.g., testis) are also encompassed in the pluripotent stem cell. Embryonic stem cell was first established in 1981, and has also been applied to the generation of knockout mouse since 1989. In 1998, human embryonic stem cell was established, which is also being utilized for regenerative medicine. ES cell can be produced by culturing an inner cell mass on a feeder cell or in a medium containing LIF. The production methods of ES cell are described in, for example, WO 96/22362, WO 02/101057, U.S. Pat. Nos. 5,843,780, 6,200,806, 6,280,718 and the like. Embryonic stem cells are available from given organizations, or a commercially available product can be purchased. For example, human embryonic stem cells, KhES-1, KhES-2 and KhES-3, are available from Kyoto University's Institute for Frontier Medical Sciences. Rx:: GFP strain (derived from KhES-1), which is a human embryonic stem cell, is available from Incorporated Administrative Agency RIKEN. EB5 cell, which is a mouse embryonic stem cell, is available from Incorporated Administrative Agency RIKEN, and D3 cell line, which is a mouse embryonic stem cell, is available from ATCC.

Nuclear transfer ES cell (ntES cell), which is one of the ES cells, can be established from a clone embryo produced by transplanting the nucleus of a somatic cell into an enucleated egg.

EG cell can be produced by culturing a primordial germ cell in a medium containing mSCF, LIF and bFGF (Cell, 70: 841-847, 1992).

The "induced pluripotent stem cell" in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of a plurality of genes selected from the group consisting of reprogramming genes including Oct3/4, Sox2, Klf4, Myc (c-Myc, N-Myc, L-Myc), Glis1, Nanog, Sall4, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc (Stem Cells, 2013; 31:458-466).

Induced pluripotent stem cell was established by Yamanaka et al. in mouse cell in 2006 (Cell, 2006, 126(4), pp. 663-676). In 2007, Induced pluripotent stem cell was also established from human fibroblast, and has pluripotency and self-renewal competence similar to those of embryonic stem cells (Cell, 2007, 131(5), pp. 861-872; Science, 2007, 318(5858), pp. 1917-1920; Nat. Biotechnol., 2008, 26(1), pp. 101-106).

Besides the production method based on direct reprogramming by gene expression, induced pluripotent stem cell can also be obtained from somatic cell by the addition of a compound and the like (Science, 2013, 341, pp. 651-654).

It is also possible to obtain established induced pluripotent stem cell and, for example, human induced pluripotent cell lines established by Kyoto University such as 201B7 cell, 20137-Ff cell, 253G1 cell, 253G4 cell, 1201C1 cell, 1205D1 cell, 1210B2 cell or, 1231A3 cell and the like are available from Kyoto University and iPS Academia Japan, Inc. As the established induced pluripotent stem cell, for example, Ff-I01 cell, Ff-I14 cell and QHJI01s04 cell established by Kyoto University are available from Kyoto University.

While the somatic cell used for producing induced pluripotent stem cell is not particularly limited, tissue-derived fibroblast, blood-lineage cells (e.g., peripheral blood mononuclear cell (PBMC), T cell), hepatocyte, pancreatic cell, intestinal epithelial cell, smooth muscle cell and the like can be mentioned.

When an induced pluripotent stem cell is produced by reprogramming by the expression of several kinds of genes, the means for gene expression is not particularly limited. Examples of the aforementioned means include an infection method using a virus vector (e.g., retrovirus vector, lentivirus vector, adenovirus vector, adeno-associated virus vector, Sendaivirus vector which is cytosolic RNA vector), a gene transfer method using a plasmid vector which is a non-viral vector (e.g., plasmid vector, episomal vector) (e.g., calcium phosphate method, lipofection method, RetroNectin method, electroporation method), a gene transfer method using an RNA vector (e.g., calcium phosphate method, lipofection method, electroporation method), a method with direct injection of protein (e.g., method using a needle, lipofection method, electroporation method) and the like.

An induced pluripotent stem cell can be produced in the presence of a feeder cell or in the absence of feeder cells (feeder-free). When an induced pluripotent stem cell is produced in the presence of a feeder cell, the induced pluripotent stem cell can be produced by a known method in the presence of a factor for maintaining undifferentiated state. While a medium to be used for producing an induced pluripotent stem cell in the absence of feeder cells, i.e., a medium containing a factor for maintaining undifferentiated state (undifferentiation maintenance medium) is not particularly limited, a known maintenance medium for embryonic stem cells and/or induced pluripotent stem cells, and a medium well known to those of ordinary skill in the art as a medium for establishing an induced pluripotent stem cell under feeder-free conditions can be used. As the undifferentiation maintenance medium for establishing an induced pluripotent stem cell under feeder-free conditions, many synthetic media have been developed and are commercially available and, for example, Essential 8 medium (manufactured by Life Technologies) can be mentioned. Essential 8 medium is DMEM/F12 medium containing L-ascorbic acid-2-phosphate magnesium (64 mg/l), sodium selenite (14 μg/l), insulin (19.4 mg/l), NaHCO3 (543 mg/l), transferrin (10.7 mg/l), bFGF (100 ng/mL), and a TGFβ family signal transduction pathway activating substance (TGFβ 1 (2 ng/mL) or Nodal (100 ng/mL)) as additives (Nature Methods, 8, 424-429 (2011)). Examples of other commercially available feeder-free medium (undifferentiation maintenance medium) include Essential 6 medium (manufactured by Life Technologies), Stabilized Essential 8 medium (manufactured by Life Technologies), S-medium (manufactured by DS Pharma Biomedical), StemPro (manufactured by Life Technologies), hESF9 (Proc Natl Acad Sci USA. 2008 Sep. 9; 105(36):13409-14), TeSR medium (manufactured by STEMCELL Technologies), mTeSR1 (manufactured by STEMCELL Technologies), mTeSR2 (manufactured by STEMCELL Technologies), and TeSR-E8 (manufactured by STEMCELL Technologies). In addition to these, examples of other feeder-free medium (undifferentiation maintenance medium) include StemFit (registered trade mark) (manufactured by Ajinomoto Co., Inc.). When an induced pluripotent stem cell is to be produced, for example, an induced pluripotent stem cell can be produced by gene transfer of 4 factors of Oct3/4, Sox2, Klf4, and Myc into somatic cell by using a Sendaivirus vector in the absence of feeder cells.

The pluripotent stem cell to be used in the present invention is preferably ES cell or induced pluripotent stem cell, more preferably induced pluripotent stem cell.

As the multipotent stem cell, tissue stem cells (also called stem cell in a tissue, tissue-specific stem cell or somatic stem cell) such as hematopoietic stem cell, neural stem cell, retinal stem cell, mesenchymal stem cell and the like can be mentioned.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of neural cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODOSHA CO., LTD. (1995); and so on.

To be specific, for example, the genomic DNA comprising the target gene to be modified (e.g., cell marker gene, histocompatibility antigen gene, disease-related gene and so on) is isolated, and a targetting vector used for homologous recombination of the target gene is produced using the isolated genomic DNA. The produced targetting vector is introduced into stem cells and the cells that showed homologous recombination between the target gene and the targetting vector are selected, whereby stem cells having the modified gene on the chromosome can be produced.

Examples of the method for isolating genomic DNA comprising the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic gene comprising the target gene can also be isolated using genomic DNA library screening system (manufactured by Genome Systems), Universal GenomeWalker Kits (manufactured by CLONTECH) and so on. A polynucleotide encoding the target protein can also be used instead of genome DNA. The polynucleotide can be obtained by amplifying the corresponding polynucleotide by the PCR method.

Production of targetting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targetting vector, any of replacement type or insertion type can be used. As the selection method, methods such as positive selection, promoter selection, negative selection, polyA selection and so on can be used.

Examples of a method for selecting the desired homologous recombinant from the selected cell lines include Southern hybridization method, PCR method and so on for the genomic DNA.

In addition, a genetically modified pluripotent stem cell can also be produced by genome editing. The genome editing is a genetic modification technique to perform gene-specific destruction, knock-in of reporter gene and the like by techniques such as Zinc Finger system, CRISPR/Cas9 system, Transcription Activator-Like Effector Nucleases (TALEN) and the like.

In the CRISPR/Cas9 genome editing system, in general, an expression vector or mRNA of Cas9 (DNA cleaving enzyme) and an expression vector or guide RNA itself expressing the guide RNA under the control of polymerase III promoter and the like are introduced into cells. The guide RNA may be a fusion RNA of RNA (crRNA) complementary to the target genome sequence and tracrRNA. When protospacer adjacent motif (PAM—sequence NGG) is present at the 3' terminal of the target genomic sequence, Cas9 dissociates the DNA double strand, recognizes the target sequence by the guide RNA, and cleaves both strands, and a mutation is introduced in the process of repairing the cleavage site.

The transcription activator-like effector nuclease (TALEN) is a system using a TAL effector produced by plant pathogenic bacterium *Xanthomonas* spp. TALEN is, in general, an artificial nuclease in which the DNA binding domain of TAL effector and the DNA cleavage domain of FokI nuclease are fused. The DNA binding domain consists of a repeat sequence of 34 amino acids, and one repeat recognizes one base of the target DNA. The 12th and the 13th amino acids in the repeat sequence are called repeat variable di-residues (RVD) and the target base is determined by this sequence. The FokI domain dimerizes on the target sequence and shows nuclease activity by designing two pairs of TALEN molecules to face each other on a specific sequence on the genome. The cleaved DNA double strand is repaired by the mechanism in the cell and a mutation is introduced during the process. When genome editing by TALEN is performed, an expression vector or mRNA of TALEN is introduced into the cell.

The "mammal" in the present invention encompasses rodents, ungulata, carnivora, primates and the like. The rodents encompass mouse, rat, hamster, guinea pig and the like. Ungulata encompass swine, bovine, goat, horse, sheep and the like. Carnivora encompasses dog, cat and the like. The "primates" in the present invention refers to mammals belonging to the primate, and the primates include prosimian such as lemur, loris, tupai and the like, and anthropoidea such as monkey, ape, human and the like.

The pluripotent stem cells to be used in the present invention are mammalian pluripotent stem cells, preferably pluripotent stem cells of rodents (e.g., mouse, rat) or primates (e.g., human, monkey), more preferably a human pluripotent stem cell, more preferably a human induced pluripotent stem cell (iPS cell) or human embryonic stem cell (ES cell).

The "suspension culture" or "suspension culture method" in the present invention refers to culture while maintaining a state in which cells or cell aggregates are suspended in a medium and a method of performing the culture. That is, the suspension culture is performed under conditions in which cells or cell aggregates are not adhered to a culture vessel and the like, and culture performed under conditions permitting adhesion to a culture vessel and the like (adhesion culture or adhesion culture method) is not included in the category of suspension culture. In this case, adhesion of cell means that a strong cell-substratum junction is formed between a cell or cell aggregate and a culture vessel. More particularly, suspension culture refers to culture under conditions in which a strong cell-substratum junction is not formed between a cell or cell aggregate and a culture vessel, and adhesion culture refers to culture under conditions in which a strong cell-substratum junction is formed between a cell or cell aggregate and a culture vessel and the like.

In a cell aggregate in suspension culture, a planar cell-cell adhesion is formed. In cell aggregates in suspension culture, a cell-substratum junction is hardly formed with a culture vessel and the like and, even if it is formed, its contribution is small. In some embodiments, an endogenous cell-substratum junction is present inside the aggregate, but a cell-substratum junction is hardly formed with a culture vessel and the like and, even if it is formed, its contribution is small.

The planar cell-cell adhesion (plane attachment) means that a cell attaches to another cell via planes. More particularly, the planar cell-cell adhesion means that, for example, not less than 1%, preferably not less than 3%, more preferably not less than 5%, of the surface area of a cell adheres to the surface of another cell. A surface of a cell can be observed by staining with a reagent (e.g., DiI) that stains membranes, immunostaining of cell adhesion factors (e.g., E-cadherin and N-cadherin).

The culture vessel to be used when performing suspension culture is not particularly limited as long as it enables "culture in suspension" and those of ordinary skill in the art can appropriately determine same. Examples of such culture vessel include flask, tissue culture flask, culture dish (dish), petri dish, tissue culture dish, multidish, microplate, microwell plate, micropore, multiplate, multiwell plate, chamber slide, schale, tube, tray, culture bag, spinner flask, Erlenmeyer flask, and roller bottle. To enable suspension culture, these culture vessels are preferably non-cell-adhesive. Useful non-cell-adhesive culture vessels include culture vessels whose surfaces have not undergone an artificial treatment for improving adhesiveness to cells (e.g., surface treatment with extracellular matrix such as basement membrane preparation, laminin, entactin, collagen, gelatin etc., and the like, or coating treatment with polymer such as polylysine, polyornithine and the like or positive electric charge treatment and the like), and the like. As a non-cell-adhesive culture vessel, culture vessels whose surfaces have been artificially treated to decrease adhesiveness to the cells (e.g., superhydrophilic treatment with MPC polymer and the like, protein low adsorption treatment etc.) and the like can be used. Roller culture using spinner flask, roller bottle and the like may be performed. The culture surface of the culture vessel may be a flat bottom or may have concaves and convexes.

A culture vessel used for adhesion culture is not particularly limited as long as "adhesion culture" can be performed, and those of ordinary skill in the art can appropriately select a culture vessel suitable according to the culture scale, culture conditions and period for the culture. Examples of such culture vessel include flasks, tissue culture flasks, culture dishes (dishes), tissue culture dishes, multi-dishes, microplates, micro-well plates, multi-plates, multiwell plates, chamber slides, schale, tubes, trays, culture bags, microcarrier, bead, stack plate, spinner flask and roller bottles. To enable adhesion culture, these culture vessels are preferably cell-adhesive. Cell-adhesive culture vessels include culture vessels whose surfaces have been artificially treated to improve adhesiveness to cells, and specifically, a surface-processed culture vessel, or, a culture vessel whose inside is coated with a coating agent can be mentioned. Examples of the coating agent include extracellular matrix such as laminin [including laminin α5β1γ1 (hereinafter laminin 511), laminin α1β1γ1 (hereinafter laminin 111) and the like and laminin fragment (laminin 511E8 etc.)], entactin, collagen, gelatin, vitronectin, Synthemax (Corning Incorporated), Matrigel and the like, or polymers such as polylysine, polyornithine and the like. Examples of the surface-processed culture vessel include culture vessels surface-processed by a positive electric charge treatment and the like.

The medium to be used for culturing cells in the present invention can be prepared from a medium generally used for culturing animal cells as a basal medium. Examples of the basal medium include media that can be used for culturing animal cells such as BME medium, BGJb medium, CMRL1066 medium, Glasgow MEM (GMEM) medium, Improved MEM Zinc Option medium, IMDM medium, Medium199 medium, Eagle MEM medium, αMEM medium, DMEM medium, F-12 medium, DMEM/F-12 medium, IMDM/F12 medium, Ham's medium, RPMI1640 medium, Fischer's medium, and mixed medium thereof etc.

The "serum-free medium" in the present invention means a medium free of unadjusted or unpurified serum. In the present invention, a medium containing purified blood-derived components and animal tissue-derived components (e.g., growth factor) is also included in a serum-free medium unless unadjusted or unpurified serum is contained therein.

The serum-free medium may contain a serum alternative. Examples of the serum alternative include one appropriately containing albumin, transferrin, fatty acid, collagen precursor, trace element, 2-mercaptoethanol or 3' thiolglycerol, or equivalents of these etc., and so on. Such serum alternative may be prepared by, for example, the method described in WO98/30679. The serum alternative may be a commercially available product. Examples of such commercially available serum alternative include Knockout™ Serum Replacement (Life Technologies, now ThermoFisher: hereinafter sometimes to be indicated as KSR), Chemically Defined Lipid Concentrated (manufactured by Life Technologies) and Glutamax™ (manufactured by Life Technologies), B27 (manufactured by Life Technologies), N2 supplement (manufactured by Life Technologies) and ITS supplement (manufactured by Life Technologies).

The serum-free medium to be used for suspension culture may appropriately contain a fatty acid or lipid, amino acid (e.g., non-essential amino acids), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 0.5% to about 30%, preferably about 1% to about 20%) of commercially available KSR (manufactured by Life Technologies) (e.g., medium of 1:1 mixture of F-12 medium and IMDM medium supplemented with 10% KSR, Chemically-defined Lipid concentrated, and 450 μM 1-monothioglycerol) may be used as such serum-free medium. In addition, as a product equivalent to KSR, the medium disclosed in JP-A-2001-508302 can be mentioned.

The "serum-containing medium" in the present invention means a medium containing unadjusted or unpurified serum. The medium may contain a fatty acid or lipid, amino acid (e.g., non-essential amino acids), vitamin, growth factor, cytokine, antioxidant, 2-mercaptoethanol, 1-monothioglycerol, pyruvic acid, buffering agent, inorganic salts and so on.

In one embodiment, the culture in the present invention may be preferably performed under xeno-free conditions. The "xeno-free" means conditions eliminating components derived from species different from that of the cell to be cultured.

In the present invention, the "medium containing a substance X" and "in the presence of a substance X" refer to a medium supplemented with an exogenous substance X or a medium containing an exogenous substance X, or in the presence of an exogenous substance X. That is, when the cells or tissues present in the medium endogenously express, secrete or produce a substance X, the endogenous substance X is distinguished from the exogenous substance X, and a medium free of exogenous substance X is understood to fall outside the category of the "medium containing a substance X", even when it contains the endogenous substance X.

For example, a "medium containing a TGFβ family signal transduction pathway inhibiting substance" is a medium supplemented with an exogenous TGFβ family signal transduction pathway inhibiting substance or a medium containing an exogenous TGFβ family signal transduction pathway inhibiting substance.

In the present invention, a "feeder cell" refers to a cell other than a stem cell that co-exists when culturing the stem cell. Examples of the feeder cells used for culturing pluripotent stem cells while maintaining undifferentiated state include mouse fibroblasts (MEF etc.), human fibroblasts, SNL cells and the like. As the feeder cells, feeder cells that underwent a growth suppression treatment is preferable. Examples of the growth suppression treatment include treatment with a growth inhibitor (e.g., mitomycin C), gamma irradiation, UV irradiation and the like. Feeder cells used for culturing pluripotent stem cells while maintaining undifferentiated state contributes to the maintenance of undifferentiated state of pluripotent stem cell by secretion of a humoral factor (preferably factor for maintaining undifferentiated state), or production of a scaffold for cell adhesion (extracellular matrix).

In the present invention, "the absence of feeder cells (feeder-free)" means culture in the absence of feeder cells. The absence of feeder cells means, for example, conditions free of addition of feeder cells, or conditions substantially free of feeder cells (e.g., the ratio of the number of feeder cells relative to the total number of cells is not more than 3%, preferably not more than 0.5%).

In the present invention, an "aggregate" of cells refers to a clump formed by assembly of cells dispersed in a medium, wherein the cells are adhered to each other. Cell clumps, embryoid bodies, spheres, spheroids are also encompassed in the cell aggregates. Preferably, a planar cell-cell adhesion is formed in the aggregate of cells. In some embodiments, cells sometimes form a cell-cell junction and/or a cell adhesion, for example, adherence junction, in some or all of the aggregates. The "aggregate" in the present invention specifically includes an aggregate produced in the second step of the above-mentioned present invention [1], which is formed by cells dispersed at the time of the start of the suspension culture, and an aggregate produced in the third step of the above-mentioned present invention [1], which contains induced retinal cells differentiated from pluripotent stem cell, and the "aggregate" also includes an aggregate already formed at the time of the start of suspension culture of the second step in the above-mentioned present invention [1]. The cell aggregate formed in the second step encompasses "embryoid body (EB)".

In the present invention, "uniformed aggregates" means that the size of each aggregate is constant when a plurality of aggregates are cultured, and that the variance in the length of the maximum diameter is small when the size of the aggregates are evaluated by the length of the maximum diameter. More specifically, it means that not less than 75% of aggregates in the whole aggregate population are within mean±100%, preferably mean±50%, more preferably mean±20%, of the maximum diameter in the population of the aggregates.

In the present invention, to "form uniformed cell aggregates" means to "rapidly aggregate a given number of dispersed cells" to form cell aggregates uniform in size, when gathering the cells to form cell aggregates and culturing the aggregates in suspension.

"Dispersion" refers to dividing cells or a tissue into small cell clusters (not less than 2 cells and not more than 100 cells, preferably not more than 50 cells) or single cells by a dispersion treatment such as enzymatic treatment, physical treatment and the like. A given number of dispersed cells is a collection of a certain number of cell clusters or single cells.

Examples of the method of dispersing pluripotent stem cells include a mechanical dispersion treatment, a cell dispersion solution treatment, and a cell protecting agent addition treatment. These treatments may be performed in combination. Preferably, a cell dispersion solution treatment is performed and then a mechanical dispersion treatment is performed.

As a method of mechanical dispersion treatment, a pipetting treatment or scraping operation by a scraper can be mentioned.

As a cell dispersion solution to be used for the cell dispersion solution treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

When pluripotent stem cells are dispersed, cell death of the pluripotent stem cells may be suppressed by treating with a cell protecting agent. As a cell protecting agent to be used for the cell protecting agent treatment, an FGF signal transduction pathway activating substance, heparin, an IGF signal transduction pathway activating substance, serum, and serum alternative can be mentioned. To suppress cell death induced by dispersion (particularly, cell death of human pluripotent stem cells), a Rho-associated coiled-coil kinase (ROCK) inhibiting substance or a Myosin inhibiting substance may be added at the time of dispersion. As a ROCK inhibiting substance, Y-27632, Fasudil (HA1077), H-1152 and the like can be mentioned. As a Myosin inhibiting substance, Blebbistatin can be mentioned. As a preferable cell protecting agent, a ROCK inhibiting substance can be mentioned.

For example, a method for dispersing pluripotent stem cells includes a method involving treating a colony of pluripotent stem cells with a cell dispersion solution (TrypLE Select) in the presence of a ROCK inhibiting substance as a cell protecting agent, and further dispersing them by pipetting.

In the production method of the present invention, it is preferable to form an aggregate of pluripotent stem cells by rapidly gathering the pluripotent stem cells. When an aggregate of pluripotent stem cells is formed in such a manner, an epithelium-like structure can be formed with good reproducibility in the cells induced and differentiated from the formed aggregate. Examples of the experimental operation to form an aggregate include a method involving keeping cells in a small space by using a plate with small wells (e.g., plate with wells having a base area of about 0.1-2.0 $cm^2$ when calculated in terms of flat bottom), micropore and so on, a method involving aggregating cells by centrifugation for a short time using a small centrifugation tube. As a plate with small wells, for example, 24 well plate (area of about 1.88 cm² when calculated in terms of flat bottom), 48 well plate (area of about 1.0 cm² when calculated in terms of flat bottom), 96 well plate (area of about 0.35 cm² when calculated in terms of flat bottom, inner diameter about 6-8 mm), and 384 well plate can be mentioned. Preferred is 96 well plate. As a shape of the plate with small wells, the shape of the bottom surface when the well is seen from above is, for example, polygon, rectangle, ellipse, true circle, preferably true circle. As a shape of the plate with small wells when the well is seen from the side well, the shape of the bottom surface may be a flat bottom structure or a structure having high outer circumference and low inner concave. The shape of the bottom surface includes, for example, U-bottom, V-bottom, M-bottom, preferably M-bottom or V-bottom. As a plate with small wells, a cell culture dish (e.g., 60 mm-150 mm dish, culture flask) with a concave convex, or dent on the bottom surface may also be used. The bottom surface of a plate with small wells is preferably a non-cell-adhesive bottom surface, preferably the aforementioned non-cell-adhesive-coated bottom surface.

Formation of aggregates of pluripotent stem cells or a cell population containing pluripotent stem cells, and uniformity thereof can be determined based on the size of the aggregate mass and the number of cells therein, macroscopic morphology, microscopic morphology by tissue staining analysis and homogeneity thereof, and the like. In addition, formation of an epithelial-like structure in the aggregate, and uniformity thereof can be determined based on the macroscopic morphology of the aggregate, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

The "tissue" in the present invention refers to a structure of a cell population having a structure in which one kind of cells having a uniformed morphology or property, or plural types of cells having different morphologies and properties are sterically arranged in a given pattern.

In the present invention, the "neural tissue" refers to a tissue constituted of neural cells including cerebrum, midbrain, cerebellum, spinal cord, retina, peripheral nerve, forebrain, hindbrain, telencephalon, diencephalon and the like in the developing stage or adult stage. A neural tissue in a cell aggregate can be confirmed by microscopic observation with optical microscopes (e.g., bright field microscope, phase contrast microscope, differential interference contrast microscope, stereo microscope etc.) or using expression of neural tissue markers such as PSA-NCAM, N-cadherin or the like as an index.

A neural tissue can form a "neuroepithelial tissue" (epithelial structure with layer structure). The characteristics of the neuroepithelial tissue can be identified by indices such as the morphology of the cells contained in the tissue, the orientation of the cell body in the tissue, the transparency of the whole tissue, the macroscopic form and the like. The amount of neuroepithelial tissues in cell aggregates can be evaluated by bright field observation using an optical microscope.

In the present invention, the "neural cell" refers to a cell other than epidermal lineage cell in a tissue derived from ectoderm. That is, it includes cells such as neural precursor cell, neuron (neuronal cell), glia, neural stem cell, neuron precursor cell, glial precursor cell and the like. The neural cell can be identified by using Nestin, TuJ1, PSA-NCAM, N-cadherin and the like as a marker. Neuron (or neuronal cell) is a functional cell that forms a neural circuit and contributes to signal transmission, and can be identified by using the expression of immature neuronal markers such as TuJ1, Dcx, HuC/D and the like and/or mature neuronal cell markers such as Map2, NeuN and the like as an index.

Neural cell encompasses retinal cell described below.

In the present invention, the "retinal cell" means a cell constituting each retinal layer or a progenitor/precursor cell thereof in retina in vivo, and nonlimitatively include retinal progenitor cell, neural retinal progenitor cell, photoreceptor precursor cell, photoreceptor cell, rod photoreceptor cell, cone photoreceptor cell, horizontal cell, amacrine cell, interneuron, retinal ganglion cell (ganglion cell), bipolar cell, retinal pigment epithelial cell (RPE), ciliary marginal zone cell, progenitor/precursor cells of these and the like. In the present invention, the "retinal tissue" means a tissue in which one type or at least two or more types of the above-mentioned cells that constitute respective retinal layers in retina in vivo are sterically arranged in layers. The retinal layer which is constituted by each cell can be confirmed by a known method, for example, presence or absence of the expression of a cell marker or the level thereof, etc.

The "retinal layer" in the present invention means each layer constituting the retina. Specific examples thereof include retinal pigment epithelial layer, photoreceptor cell layer, external limiting membrane, outer nuclear layer, outer plexiform layer, inner nuclear layer, inner plexiform layer, ganglion cell layer, nerve fiber layer and inner limiting membrane.

The "retinal progenitor cell" in the present invention refers to a progenitor cell capable of differentiating into any mature retinal layer-specific neural cells including photoreceptor cell, rod photoreceptor cell, cone photoreceptor cell, horizontal cell, bipolar cell, amacrine cell, retinal ganglion cell, retinal pigment epithelial cell and the like.

In the present invention, the "neural retinal progenitor cell" refers to a progenitor cell capable of differentiating into any one of or plural mature retinal layer-specific neural cells including photoreceptor cell, horizontal cell, bipolar cell, amacrine cell, retinal ganglion cell, and the like. In general, a neural retinal progenitor cell does not differentiate into a retinal pigment epithelial cell.

The precursor cell of photoreceptor, precursor cell of horizontal cell, precursor cell of bipolar cell, precursor cell of amacrine cell, precursor cell of retinal ganglion cell, and precursor cell of retinal pigment epithelial progenitor cell respectively refers to precursor cell committed to differentiate into photoreceptor cell, horizontal cell, bipolar cell, amacrine cell, retinal ganglion cell, and retinal pigment epithelial cell.

In the present invention, the "retinal layer-specific neural cell" is a cell constituting a retina layer and is a neuronal cell specific to the retinal layer. Examples of the retinal layer-specific neural cell include bipolar cell, retinal ganglion cells, amacrine cell, horizontal cell, photoreceptor cell, retinal pigment epithelial cell, rod photoreceptor cell and cone photoreceptor cell.

Examples of the retinal cell marker include Rx (also referred to as Rax), PAX6 and Chx10 expressed in retinal progenitor cell, Nkx2.1 expressed in progenitor cell of hypothalamus neuron but not expressed in retinal progenitor cell, Sox1 expressed in hypothalamus neuroepithelium but not expressed in retina, Crx and Blimp1 expressed in progenitor cell of photoreceptor cell, and the like. Examples of the marker of the retinal layer-specific neural cell include Chx10, PKCα and L7 expressed in bipolar cell, TUJI and Brn3 expressed in retinal ganglion cells, Calretinin expressed in amacrine cell, Calbindin expressed in horizontal cell, Rhodopsin and Recoverin expressed in mature photoreceptor cell, Nrl and Rhodopsin expressed in rod photoreceptor cell, Rxr-gamma, S-Opsin and M/L-Opsin expressed in cone photoreceptor cell, RPE65 and Mitf expressed in retinal pigment epithelial cell, Rdh10 and SSEA1 expressed in ciliary marginal zone cell and the like.

2. Method for Producing Retinal Cells or Retinal Tissue

One embodiment of the present invention is a method for producing retinal cells or a retinal tissue, comprising the following steps (1)-(3):
(1) a first step of culturing pluripotent stem cells in the absence of feeder cells in a medium containing 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension in a medium containing a Wnt signal transduction pathway inhibiting substance to form a cell aggregate, and
(3) a third step of culturing the aggregate obtained in the second step in suspension in the presence or absence of a Wnt signal transduction pathway inhibiting substance in a medium containing a BMP signal transduction pathway activating substance to obtain an aggregate containing a retinal cell or a retinal tissue.

2-1. Step (1)

In step (1), pluripotent stem cells are cultured in the absence of feeder cells in a medium containing 1) a TGFβ family signal transduction pathway inhibiting substance and/or a Sonic hedgehog signal transduction pathway activating substance, and 2) a factor for maintaining undifferentiated state.

A preferable pluripotent stem cell in step (1) is an induced pluripotent stem cell or an embryonic stem cell (ES cell), more preferably a human induced pluripotent stem cell or a human embryonic stem cell (ES cell).

The production method of induced pluripotent stem cells is not particularly limited, and it can be produced by a method well known to those of ordinary skill in the art as mentioned above. It is also desirable to perform a step for preparing induced pluripotent stem cells (that is, a step of reprogramming somatic cells to establish pluripotent stem cells) under feeder-free condition.

While the production method of embryonic stem cells (ES cells) is not particularly limited, and can be produced by a method well known to those of ordinary skill in the art as mentioned above, it is also desirable to perform a step for preparing embryonic stem cells (ES cells) under feeder-free condition.

The maintenance culture or expansion culture of pluripotent stem cells to be used in step (1) can be performed by a method well known to those of ordinary skill in the art. While the maintenance culture and expansion culture of pluripotent stem cells can be performed by adhesion culture or suspension culture, it is preferably performed by adhesion culture. While the maintenance culture and expansion culture of pluripotent stem cells may be performed in the presence of feeders or under feeder-free condition, it is preferably performed under feeder-free condition. The absence of feeder cells (feeder-free) in maintenance culture and expansion culture of pluripotent stem cells means a condition substantially free of feeder cells (e.g., the ratio of number of feeder cells relative to the total number of cells is not more than 3%). Preferably, the maintenance culture and expansion culture of pluripotent stem cells is performed under conditions free of feeder cells.

The absence of feeder cells (feeder-free) in step (1) means a condition substantially free of feeder cells (e.g., the ratio of the number of feeder cells relative to the total number of cells is not more than 3%). Preferably, step (1) is performed under a condition free of feeder cells. The medium to be used in step (1) is not particularly limited as long as it is a medium enabling culture of pluripotent stem cells to maintain undifferentiated state under feeder-free conditions (feeder-free medium). To enable culture to maintain undifferentiated state, it contains a factor for maintaining undifferentiated state.

The factor for maintaining undifferentiated state is not particularly limited as long as it is a substance having an action to suppress differentiation of pluripotent stem cells. Examples of the factor for maintaining undifferentiated state widely used by those of ordinary skill in the art include an FGF signal transduction pathway activating substance, a TGFβ family signal transduction pathway activating substance, insulin and the like in the case of primed pluripotent stem cells (e.g., human ES cells, human iPS cells). As the FGF signal transduction pathway activating substance, fibroblast growth factors (e.g., bFGF, FGF4, FGF8) can be specifically mentioned. As the TGFβ family signal transduction pathway activating substance, a TGFβ signal transduction pathway activating substance, a Nodal/Activin signal transduction pathway activating substance can be mentioned. As the TGFβ signal transduction pathway activating substance, for example, TGFβ1, TGFβ2 can be mentioned. As the Nodal/Activin signal transduction pathway activating substance, for example, Nodal, Activin A, Activin B can be mentioned. The factor for maintaining undifferentiated state may contain one or more kinds of these. When human pluripotent stem cells (human ES cells, human iPS cells etc.) are cultured, the medium in step (1) preferably contains bFGF as a factor for maintaining undifferentiated state.

The factor for maintaining undifferentiated state to be used in the present invention is generally a factor for maintaining undifferentiated state of mammals. The mammals are, for example, those mentioned above. Since the factor for maintaining undifferentiated state may have cross-reactivity among mammal species, a factor for maintaining undifferentiated state of any mammal may also be used as long as the undifferentiated state of the pluripotent stem cells to be cultured can be maintained. Preferably, a factor for maintaining undifferentiated state of a mammal of the same species as the cells to be cultured is used. For example, for the culture of human pluripotent stem cells, human factor for maintaining undifferentiated states (e.g., bFGF, FGF4, FGF8, EGF, Nodal, Activin A, Activin B, TGFβ 1, TGFβ 2 etc.) are used. Here, the "human protein X" means that protein X has the amino acid sequence of protein X naturally expressed in human in vivo.

The factor for maintaining undifferentiated state to be used in the present invention is preferably isolated. Being "isolated" means that an operation to remove factors other than the intended component or cell has been performed, and the component or cell is no longer in a naturally occurring state. Therefore, "isolated protein X" does not include an endogenous protein X produced from the cells or tissues to be cultured, and contained in a cell or tissue or in the medium. The purity of the "isolated protein X" (percentage of the weight of protein X to the total protein weight) is generally not less than 70%, preferably not less than 80%, more preferably not less than 90%, further preferably not less than 99%, further preferably 100%. Therefore, in one embodiment, the present invention comprises a step of providing an isolated factor for maintaining undifferentiated state. In one embodiment, it includes a step of exogenously adding an isolated factor for maintaining undifferentiated state to a medium used in step (1). Alternatively, a factor for maintaining undifferentiated state may be added in advance to a medium to be used in step (1).

The concentration of the factor for maintaining undifferentiated state in the medium to be used in step (1) is a concentration capable of maintaining the undifferentiated state of the pluripotent stem cells to be cultured, and can be appropriately determined by those of ordinary skill in the art. For example, specifically, when bFGF is used as a factor for maintaining undifferentiated state in the absence of feeder cells, the concentration thereof is generally about 4 ng-500 ng/mL, preferably about 10 ng-200 ng/mL, more preferably about 30 ng-150 ng/mL.

As the feeder free medium (i.e., undifferentiation maintenance medium) to be used in step (1), many synthetic media have been developed and are commercially available. For example, Essential 8 (manufactured by Life Technologies) medium can be mentioned. Essential 8 medium is DMEM/F12 medium containing L-ascorbic acid-2-phosphate magnesium (64 mg/l), sodium selenite (14 µg/l), insulin (19.4 mg/l), NaHCO$_3$ (543 mg/l), transferrin (10.7 mg/l), bFGF (100 ng/mL), and a TGFβ family signal transduction pathway activating substance (TGFβ 1 (2 ng/mL) or Nodal (100 ng/mL)) as additives (Nature Methods, 8, 424-429 (2011)). Examples of other commercially available feeder-free medium (undifferentiation maintenance medium) include Essential 6 medium (manufactured by Life Technologies), Stabilized Essential 8 medium (manufactured by Life Technologies), S-medium (manufactured by DS Pharma Biomedical Co., Ltd.), StemPro (manufactured by manufactured by Life Technologies), hESF9 (Proc Natl Acad Sci USA. 2008 Sep. 9; 105(36):13409-14), TeSR medium (manufactured by STEMCELL Technologies), mTeSR1 (manufactured by STEMCELL Technologies), mTeSR2 (manufactured by STEMCELL Technologies), TeSR-E8 (manufactured by STEMCELL Technologies). In addition to these, StemFit (registered trade mark) (manufactured by Ajinomoto Co., Inc.) can be mentioned as the feeder-free medium. The present invention can be performed conveniently by using these in the above-mentioned step (1).

In step (1), the pluripotent stem cells may be cultured under any conditions of suspension culture and adhesion culture, preferably adhesion culture.

While a culture vessel used for adhesion culture is not particularly limited as long as "adhesion culture" can be performed, a cell-adhesive culture vessel is preferable. Cell-adhesive culture vessels include culture vessels whose surfaces have been artificially treated to improve adhesiveness to cells, and specifically, the above-mentioned culture vessel whose inside is coated with a coating agent can be mentioned. Examples of the coating agent include extracellular matrix such as laminin [including laminin α5β1γ1 (hereinafter laminin 511), laminin α1β1γ1 (hereinafter laminin 111) and the like and laminin fragment (laminin 511E8 etc.)], entactin, collagen, gelatin, vitronectin, Synthemax (Corning Incorporated), Matrigel and the like, or polymer such as polylysine, polyornithine and the like. It is also possible to use a culture container whose surface is processed by a positive electric charge treatment and the like.

Preferred is laminin and more preferred is laminin 511E-8. Laminin 511E-8 can be a commercially available product (e.g., iMatrix-511, Nippi).

The medium used in step (1) contains a TGFβ family signal transduction pathway inhibiting substance and/or a Sonic hedgehog signal transduction pathway activating substance. Specifically, for example, a TGFβ family signal transduction pathway inhibiting substance and/or a Sonic hedgehog signal transduction pathway activating substance can be added to the aforementioned undifferentiation maintenance medium. In the first step, pluripotent stem cells are treated with a TGFβ family signal transduction pathway inhibiting substance and/or a Sonic hedgehog signal transduction pathway activating substance and subjected to suspension culture in the second step, whereby the state of the cells changes, the quality of the aggregates is improved, and cell aggregates maintaining an undifferentiated state can be produced with high efficiency. The thus-obtained cell aggregates are expected to show characteristics of, for example, spherical cell aggregates with a smooth surface and dense inside.

The TGFβ family signal transduction pathway (i.e., TGFβ superfamily signal transduction pathway) is a signal transduction pathway intracellularly transduced by Smad family with TGFβ, Nodal/Activin or BMP as a ligand.

The TGFβ family signal transduction pathway inhibiting substance is a substance that inhibits TGFβ family signal transduction pathway, that is, a signal transduction pathway transduced by the Smad family. Specifically, a TGFβ signal transduction pathway inhibiting substance, a Nodal/Activin signal transduction pathway inhibiting substance and a BMP signal transduction pathway inhibiting substance can be mentioned.

The TGFβ signal transduction pathway inhibiting substance is not particularly limited as long as it is a substance inhibiting a signal transduction pathway caused by TGFβ, and may be any of nucleic acid, protein and low-molecular organic compound. As the substance, for example, a substance directly acting on TGFβ (e.g., protein, antibody, aptamer etc.), a substance suppressing expression of gene encoding TGFβ (e.g., antisense oligonucleotide, siRNA etc.), a substance that inhibits the binding of TGFβ receptor and TGFβ, and a substance that inhibits physiological activity caused by signal transduction by the TGFβ receptor (e.g., TGFβ receptor inhibitor, Smad inhibitor etc.) can be mentioned. As a protein known as a TGFβ signal transduction pathway inhibiting substance, Lefty and the like can be mentioned. As a TGFβ signal transduction pathway inhibiting substance, compounds well known to those of ordinary skill in the art can be used and, specifically, SB431542, LY-364947, SB-505124, A-83-01 and the like can be mentioned. SB431542 (4-(5-benzol[1,3]dioxol-5-yl-4-pyridin-2-yl-1H-imidazol-2-yl)-benzamide) and A-83-01 (3-(6-methyl-2-pyridinyl)-N-phenyl-4-(4-quinolinyl)-1H-pyrazole-1-carbothioamide) is a compound known as an inhibitor of TGFβ receptor (ALK5) and an Activin receptor (ALK4/7) (i.e., TGFβR inhibitor). One or more kinds of these may be contained as a TGFβ signal transduction pathway inhibiting substances. The TGFβ signal transduction pathway inhibiting substance is preferably SB431542 or A-83-01.

The Nodal/Activin signal transduction pathway inhibiting substance is not particularly limited as long as it is a substance inhibiting a signal transduction pathway caused by Nodal or Activin, and may be any of nucleic acid, protein and a low-molecule organic compound. Examples of the substance include a substance that directly acts on Nodal or Activin (e.g., antibody, aptamer etc.), a substance that suppresses expression of gene encoding Nodal or Activin (e.g., antisense oligonucleotide, siRNA etc.), a substance that suppresses binding of Nodal/Activin receptor and Nodal/Activin, and a substance that suppresses physiological activity caused by signal transduction by Nodal/Activin receptor. As the Nodal/Activin signal transduction pathway inhibiting substance, a compound well known to those of ordinary skill in the art can be used and, specifically, SB431542, A-83-01 and the like can be mentioned. In addition, a protein (Lefty, Cerberus etc.) known as a Nodal/Activin signal transduction pathway inhibiting substance may be used. One or more kinds of these may be contained as a Nodal/Activin signal transduction pathway inhibiting substance. The Nodal/Activin signal transduction pathway inhibiting substance is preferably SB431542, A-83-01 or Lefty.

The BMP signal transduction pathway inhibiting substance is not particularly limited as long as it a substance inhibiting a signal transduction pathway caused by BMP, and may be any of nucleic acid, protein and a low-molecule organic compound. As BMP here, BMP2, BMP4, BMP7 and GDF7 can be mentioned. Examples of the substance include a substance that directly acts on BMP (e.g., antibody, aptamer etc.), a substance that suppresses expression of gene encoding BMP (e.g., antisense oligonucleotide, siRNA etc.), a substance that suppresses binding of BMP receptor (BMPR) and BMP, and a substance that suppresses physiological activity caused by signal transduction by BMP receptor. As BMPR, ALK2 or ALK3 can be mentioned. As the BMP signal transduction pathway inhibiting substance, a compound well known to those of ordinary skill in the art can be used and, specifically, LDN193189, Dorsomorphin and the like can be mentioned. Here, LDN193189 (4-[6-(4-piperazin-1-ylphenyl)pyrazolo[1,5-a]pyrimidin-3-yl]quinoline) is a known BMPR (ALK2/3) inhibitor (hereinafter BMPR inhibitor) and is generally commercially available in the form of hydrochloride. In addition, a protein known as a BMP signal transduction pathway inhibiting substance (Chordin, Noggin etc.) may also be used. One or more kinds of these may be contained as a BMP signal transduction pathway inhibiting substance. The BMP signal transduction pathway inhibiting substance is preferably LDN193189.

The TGFβ family signal transduction pathway inhibiting substance is preferably Lefty, SB431542, A-83-01 or LDN193189.

Multiple kinds of TGFβ family signal transduction pathway inhibiting substances with different points of action may be used in combination. By combining them, it is expected that the improving effect on the quality of the aggregate will be enhanced. For example, a combination of a TGFβ signal transduction pathway inhibiting substance and a BMP signal transduction pathway inhibiting substance, a combination of a TGFβ signal transduction pathway inhibiting substance and Nodal/Activin signal transduction pathway inhibiting substance, and a combination of a BMP signal transduction pathway inhibiting substance and a Nodal/Activin signal transduction pathway inhibiting substance can be mentioned. Preferably, a TGFβ signal transduction pathway inhibiting substance and a BMP signal transduction pathway inhibiting substance are used in combination. A specific preferable combination is a combination of SB431542 and LDN193189.

The Sonic hedgehog (hereinafter sometimes to be indicated as Shh) signal transduction pathway activating substance is a substance capable of enhancing signal transduction mediated by Shh. Examples of the Shh signal transduction pathway activating substance include proteins belonging to the Hedgehog family (e.g., Shh and Ihh), Shh receptor, Shh receptor agonist, PMA (Purmorphamine; 9-cyclohexyl-N-[4-(4-morpholinyl)phenyl]-2-(1-naphthalenyloxy)-9H-purin-6-amine), SAG (Smoothened Agonist; N-methyl-N'-(3-pyridinylbenzyl)-N'-(3-chlorobenzo[b]thiophene-2-carbonyl)-1,4-diaminocyclohexane) and the like. The Shh signal transduction pathway activating substance may contain one or more kinds of these. A preferred Shh signal transduction pathway activating substances are Shh protein (Genbank accession numbers: NM 000193, NP 000184), SAG and PMA.

A TGFβ family signal transduction pathway inhibiting substance and a Shh signal transduction pathway activating substance may be used in combination. By combining them, it is expected that the improving effect on the quality of the aggregate will be enhanced. Examples of the specific combination include a combination of any TGFβ family signal transduction pathway inhibiting substance selected from the group consisting of Lefty, SB431542, A-83-01 and LDN193189, and any Shh signal transduction pathway activating substance selected from the group consisting of Shh protein, SAG and PMA. When a TGFβ family signal transduction pathway inhibiting substance and a Shh signal transduction pathway activating substance are used in combination, the cells may be cultured in a medium containing both a TGFβ family signal transduction pathway inhibiting substance and a Shh signal transduction pathway activating substance, or the cells may be treated with any one of a TGFβ family signal transduction pathway inhibiting substance and a Shh signal transduction pathway activating substance and then the cells may be continuously treated with either or both of them. Alternatively, the cells may be treated with both a TGFβ family signal transduction pathway inhibiting substance and a Shh signal transduction pathway activating substance, and then continuously treated with either of them.

The concentration of the TGFβ family signal transduction pathway inhibiting substance and Sonic hedgehog signal transduction pathway activating substance can be appropriately determined to fall within a range capable of achieving the aforementioned effects. For example, SB431542 is generally used at a concentration of 0.1-200 μM, preferably 2-50 μM. A-83-01 is generally used at a concentration of 0.05-50 μM, preferably 0.5-5 μM. LDN193189 is generally used at a concentration of 1-2000 nM, preferably 10-300 nM. Lefty is generally used at a concentration of 5-200 ng/ml, preferably 10-50 ng/ml. Shh protein is generally used at a concentration of 20-1000 ng/ml, preferably 50-300 ng/ml. SAG is generally used at a concentration of 1-2000 nM, preferably 10-700 nM, more preferably 30-600 nM. PMA is generally used at a concentration of 0.002-20 μM, preferably 0.02-2 μM. In one embodiment, a TGFβ family signal transduction pathway inhibiting substance can be appropriately used in an amount showing a TGFβ family signal transduction pathway inhibiting activity equivalent to that of SB43154 at the aforementioned concentration. In one embodiment, a Sonic hedgehog signal transduction pathway activating substance can be appropriately used in an amount showing a Shh signal transduction promoting activity equivalent to that of SAG at the aforementioned concentration.

The TGFβ family signal transduction pathway inhibiting activity of SB431542, LDN193189 and the like can be determined by detecting, for example, phosphorylation of Smad by a method well known to those of ordinary skill in the art such as a Western blotting method (Mol Cancer Ther. (2004) 3, 737-45.). Sonic hedgehog signal transduction promoting activity of SAG and the like can be determined by a method well known to those of ordinary skill in the art, for example, a reporter gene assay taking note of the expression of the Gli1 gene (Oncogene (2007) 26, 5163-5168).

While the medium used for step (1) may be a serum-containing medium or a serum-free medium, it is preferably a serum-free medium, to avoid contamination with chemically-undefined components.

To avoid contamination with a chemically-undefined component, a medium to be used for step (1) may be a medium whose components are chemically-defined.

For culturing pluripotent stem cells under feeder-free conditions in step (1), the aforementioned feeder-free medium (That is, undifferentiation maintenance medium) can be used as a medium. As a feeder-free medium (undifferentiation maintenance medium), Essential 8 medium, Essential 6 medium, Stabilized Essential 8 medium, S-medium, StemPro medium, hESF9 medium, TeSR medium, mTeSR medium (mTeSR1, mTeSR2 and the like), TeSR-E8, StemFit (registered trade mark) medium and the like can be mentioned, and Essential 8 medium or StemFit (registered trade mark) medium is preferably used.

For culturing pluripotent stem cells under feeder-free conditions in step (1), an appropriate matrix may be used as a scaffold to provide a scaffold in stead of the feeder cells to the pluripotent stem cell. The pluripotent stem cells are subjected to adhesion culture in a cell container whose surface is coated with a matrix as a scaffold.

As a matrix available as a scaffold, laminin (Nat Biotechnol 28, 611-615 (2010)), laminin fragment (Nat Commun 3, 1236 (2012)), basement membrane preparation (Nat Biotechnol 19, 971-974 (2001)), gelatin, collagen, heparan sulfate proteoglycan, entactin, vitronectin and the like can be mentioned.

"Laminin" is a heterotrimer molecule consisting of α, β, γ chains and an extracellular matrix protein containing isoforms having different subunit chain compositions. Specifically, laminin has about 15 species of isoforms based on the combinations of heterotrimers with 5 species of α chains, 4 species of β chains and 3 species of γ chains. The name of laminin is determined by combining respective numbers of α chain (α1-α5), β chain (β1-β4) and γ chain (γ1-γ3). For example, a laminin having a combination of α5 chain, β1 chain, γ1 chain is named laminin 511. In the present invention, laminin 511 is preferably used (Nat Biotechnol 28, 611-615 (2010)).

Laminin to be used in the present invention is generally a mammalian laminin. As the mammal, those mentioned above can be recited. To achieve xeno-free conditions, laminin of a mammal of the same species as the cell to be cultured is preferably used. For example, human laminin (preferably, human laminin 511) is used for culturing human pluripotent stem cells.

A laminin fragment to be used in the present invention is not particularly limited as long as it has adhesiveness to pluripotent stem cells and enables maintenance culture of pluripotent stem cell under feeder-free conditions, and is preferably E8 fragment. Laminin E8 fragment was identified as a fragment with strong cell adhesion activity among the fragments obtained by digestion of laminin 511 with elastase (EMBO J., 3:1463-1468, 1984, J. Cell Biol., 105:589-598, 1987). In the present invention, E8 fragment of laminin 511 is preferably used (Nat Commun 3, 1236 (2012), Scientific Reports 4, 3549 (2014)). The laminin E8 fragment to be used in the present invention is not required to be an elastase-digestion product of laminin and may be a recombinant. To avoid contamination of unidentified components, a recombinant laminin fragment is preferably used in the present invention. An E8 fragment of laminin 511 is commercially available and can be purchased from, for example, Nippi, Inc. and the like.

The laminin or laminin fragment to be used in the present invention is preferably isolated.

The "basement membrane preparation" in the present invention refers to one containing basement membrane-constituting components having a function to control cell morphology, differentiation, growth, motility, expression of function and so on which are similar to those of epithelial cell, when intended cells capable of forming a basement membrane are plated thereon and cultured. For example, retinal cells and retinal tissues produced by the present invention may be dispersed, and cultured in the presence of a basement membrane preparation when further adhesion culture is performed. Here, the "basement membrane constituting components" refers to extracellular matrix molecules in the form of a thin membrane present between epithelial cell layer and interstitial cell layer and so on in animal tissues. A basement membrane preparation can be produced by, for example, removing cells capable of forming a basement membrane, which adhere onto a support via a basement membrane, from a support with a solution capable of dissolving the lipid of the cells, an alkali solution and so on. Examples of the basement membrane preparation include products commercially available as basement membrane preparation (e.g., Matrigel™ (manufactured by Corning Incorporated: hereinafter sometimes referred to as Matrigel)), Geltrex™ (manufactured by Life Technologies), and extracellular matrix molecules known as basement membrane components (e.g., laminin, type IV collagen, heparan sulfate proteoglycan, entactin and so on).

Matrigel™ is a basement membrane preparation extracted from Engelbreth Holm Swarn (EHS) mouse sarcoma. The main component of Matrigel™ is type IV collagen, laminin, heparan sulfate proteoglycan, and entactin. In addition to these, TGF-β, FGF, tissue plasminogen activator, and a growth factor naturally produced by EHS tumor are contained. The "growth factor reduced product" of Matrigel™ has a lower growth factor concentration than common Matrigel™, and the standard concentration thereof is <0.5 ng/ml for EGF, <0.2 ng/ml for NGF, <5 pg/ml for PDGF, 5 ng/ml for IGF1, and 1.7 ng/ml for TGFβ.

To avoid contamination of unidentified components, an isolated laminin or laminin fragment is preferably used in the present invention.

Preferably, in the culture of pluripotent stem cells under feeder-free conditions in step (1), the human pluripotent stem cells are cultured in an adhered state in a cell container with surface coated with isolated laminin 511 or E8 fragment of laminin 511 (more preferably, E8 fragment of laminin 511).

While the period for the culture of pluripotent stem cells in step (1) is not particularly limited as long as the effect of improving the quality of the aggregate formed in step (2) can be achieved, it is generally 0.5-144 hr. The culture period of pluripotent stem cells in step (1) is preferably not less than 1 hr, not less than 2 hr, not less than 6 hr, not less than 12 hr, not less than 18 hr, not less than 20 hr or not less than 24 hr. The culture period of pluripotent stem cells in step (1) is preferably within 96 hr, within 72 hr, within 60 hr, within 48 hr or within 28 hr. In one embodiment, the range of the culture period of pluripotent stem cells in step (1) is preferably 2-96 hr, 6-72 hr, 6-60 hr, 12-60 hr, 18-60 hr, 18-48 hr or 18-28 hr (e.g., 24 hr). That is, the first step is started 0.5-144 hr (preferably, 12-60 hr, 18-48 hr or 18-28 hr) before the start of the suspension culture in step (2), and step (2) is continuously performed after completion of step (1). When the cells are treated with either of a TGFβ family signal transduction pathway inhibiting substance and a Shh signal transduction pathway activating substance and then continuously treated with the other, the treatment time of each can be set to independently fall within the range of the aforementioned culture period.

When the cells are treated with both of the TGFβ family signal transduction pathway inhibiting substance and the Shh signal transduction pathway activating substance and then continuously treated with one of them, and when the cells are treated with either of the TGFβ family signal transduction pathway inhibiting substance and the Shh signal transduction pathway activating substance and then continuously treated with the both, the treatment time of each can also be set to independently fall within the range of the aforementioned culture period.

In one embodiment, the cells can be cultured with either of the TGFβ family signal transduction pathway inhibiting substance (e.g., SB431542 or LDN193189) and the Shh signal transduction pathway activating substance (e.g., SAG) for 18-28 hr (e.g., 24 hr) and then further cultured with either of the TGFβ family signal transduction pathway inhibiting substance (e.g., SB431542 or LDN193189) and the Shh signal transduction pathway activating substance (e.g., SAG) for 18-28 hr (e.g., 24 hr). In this case, the concentration of the TGFβ family signal transduction pathway inhibiting substance is, for example, a concentration showing a TGFβ signal transduction pathway inhibiting activity equivalent to that of SB431542 at 3 µM-10 µM, or a concentration showing a BMP signal transduction pathway inhibiting activity equivalent to that of LDN193189 at 50 nM-200 nM, and a concentration of the Shh signal transduction pathway activating substance is, for example, a concentration showing a signal transduction promoting activity equivalent to that of SAG at 100 nM-500 nM.

In another embodiment, the cells can be cultured with both of the TGFβ family signal transduction pathway inhibiting substance (e.g., SB431542 or LDN193189) and the Shh signal transduction pathway activating substance (e.g., SAG) for 18-28 hr (e.g., 24 hr) and then further cultured with either of the TGFβ family signal transduction pathway inhibiting substance (e.g., SB431542 or LDN193189) and the Shh signal transduction pathway activating substance (e.g., SAG) for 18-28 hr (e.g., 24 hr). In this case, the concentration of the TGFβ family signal transduction pathway inhibiting substance is, for example, a concentration showing a TGFβ signal transduction pathway inhibiting activity equivalent to that of SB431542 at 3 µM-10 µM, or a concentration showing a BMP signal transduction pathway inhibiting activity equivalent to that of LDN193189 at 50 nM-200 nM, and a concentration of the Shh signal transduction pathway activating substance is, for example, a concentration showing a signal transduction promoting activity equivalent to that of SAG at 100 nM-500 nM.

In another embodiment, the cells can be cultured with either of the TGFβ family signal transduction pathway inhibiting substance (e.g., SB431542 or LDN193189) and the Shh signal transduction pathway activating substance (e.g., SAG) for 18-28 hr (e.g., 24 hr) and then further cultured with both of the TGFβ family signal transduction pathway inhibiting substance (e.g., SB431542 or LDN193189) and the Shh signal transduction pathway activating substance (e.g., SAG) for 18-28 hr (e.g., 24 hr). In this case, the concentration of the TGFβ family signal transduction pathway inhibiting substance is, for example, a concentration showing a TGFβ signal transduction pathway inhibiting activity equivalent to that of SB431542 at 3 µM-10 µM, or a concentration showing a BMP signal transduction pathway inhibiting activity equivalent to that of LDN193189 at 50 nM-200 nM, and a concentration of the Shh signal transduction pathway activating substance is, for example, a concentration showing a signal transduction promoting activity equivalent to that of SAG at 100 nM-500 nM.

The culture conditions such as culture temperature, and $CO_2$ concentration in step (1) can be appropriately determined. While the culture temperature is, for example, about 30° C. to about 40° C., preferably about 37° C. The $CO_2$ concentration is, for example, about 1% to about 10%, preferably about 5%.

In one preferable embodiment, human pluripotent stem cells (e.g., human iPS cells) are cultured in an adhered state in the absence of feeder cells and in a serum-free medium (undifferentiation maintenance medium) containing bFGF. The adhesion culture is preferably performed in a cell container with surface coated with laminin 511, E8 fragment of laminin 511 or vitronectin. The adhesion culture is preferably performed using Essential 8, TeSR medium, mTeSR medium, mTeSR-E8 medium, or StemFit (registered trade mark) medium, more preferably Essential 8 or StemFit (registered trade mark) medium, as a feeder-free medium (undifferentiation maintenance medium).

In one embodiment, human pluripotent stem cells (e.g., human iPS cells) are cultured in suspension in the absence of feeder cells and in a serum-free medium containing bFGF. In the suspension culture, human pluripotent stem cells may form an aggregate of human pluripotent stem cells.

In a preferable embodiment, the cell obtained in step (1) is a cell maintaining pluripotent-like properties (pluripotent-like state) and the pluripotent-like properties are maintained throughout step (1). The pluripotent-like properties mean that at least a part of the characteristics unique to and common to the pluripotent stem cells including pluripotency is maintained. The pluripotent-like properties do not require strict pluripotency. Specifically, a state expressing all or some of the markers to be the index of pluripotent properties (pluripotent state) is included in the "pluripotent-like properties". As a marker of the pluripotent-like properties, Oct3/4 positive, alkaline phosphatase positive and the like can be mentioned. In one embodiment, a cell maintaining the pluripotent-like properties is Oct3/4 positive. Even if the expression level of Nanog is lower than that of ES cell or iPS cell, it is included in "cell showing pluripotent-like properties".

In one embodiment, the cells obtained in step (1) are stem cells having an ability to differentiate into at least a retinal cell or retinal tissue (preferably, retinal tissue, retinal progenitor cell, or retinal layer-specific neural cell). In one embodiment, the cells obtained in step (1) are Oct3/4 positive stem cells having an ability to differentiate into at least a retinal cell or retinal tissue (preferably, retinal tissue, retinal progenitor cell or retinal layer-specific neural cell). In one embodiment, the cells obtained in step (1) contain not less than 60%, for example, not less than 90%, of Oct3/4 positive stem cells.

In a preferable embodiment, in step (1), human pluripotent stem cells (e.g., iPS cell, ES cell) are subjected to adhesion culture in the absence of feeder cells in a serum-free medium containing a TGFβ family signal transduction pathway inhibiting substance and/or a Sonic hedgehog signal transduction pathway activating substance, and bFGF.

The above-mentioned adhesion culture in step (1) is preferably performed in a cell container with a surface coated with laminin 511 or E8 fragment of laminin 511. The TGFβ family signal transduction pathway inhibiting substance is preferably a TGFβ signal transduction pathway inhibiting substance (e.g., SB431542, A-83-01, Lefty), a Nodal/Activin signal transduction pathway inhibiting substance (e.g., Lefty, SB431542, A-83-01), a BMP signal transduction pathway inhibiting substance (e.g., LDN193189, Chordin, Noggin), or a combination of these (e.g., SB431542 and LDN193189). The TGFβ family signal transduction pathway inhibiting substance is further preferably Lefty, SB431542, A-83-01, or LDN193189, or a combination of these (e.g., SB431542 and LDN193189). The Sonic hedgehog signal transduction pathway activating substance is preferably Shh protein, SAG or Purmorphamine (PMA), more preferably SAG. The TGFβ family signal transduction pathway inhibiting substance (e.g., Lefty, SB431542, A-83-01, LDN193189) and the Sonic hedgehog signal transduction pathway activating substance (e.g., Shh protein, SAG, PMA) may be used in combination. The culture period is 0.5-144 hr (preferably 2-96 hr, 6-72 hr, 6-60 hr, 12-60 hr, 18-60 hr, 18-48 hr or 18-28 hr (e.g., 24 hr)). In the course of the culture, the TGFβ family signal transduction pathway inhibiting substance (e.g., Lefty, SB431542, A-83-01, LDN193189), the Shh signal transduction pathway activating substance (e.g., Shh protein, SAG, PMA) or the combination thereof may be changed. In one embodiment, the cells can be cultured with both of a TGFβ family signal transduction pathway inhibiting substance (e.g., SB431542, LDN193189) and a Shh signal transduction pathway activating substance (e.g., SAG) for 18-28 hr (e.g., 24 hr) and then further cultured with either of a TGFβ family signal transduction pathway inhibiting substance (e.g., SB431542, LDN193189) and a Shh signal transduction pathway activating substance (e.g., SAG) for 18-28 hr (e.g., 24 hr). In another embodiment, the cells can be cultured with either of a TGFβ family signal transduction pathway inhibiting substance (e.g., SB431542, LDN193189) and a Shh signal transduction pathway activating substance (e.g., SAG) for 18-28 hr (e.g., 24 hr) and then further cultured with both or either of a TGFβ family signal transduction pathway inhibiting substance (e.g., SB431542, LDN193189) and a Shh signal transduction pathway activating substance (e.g., SAG) for 18-28 hr (e.g., 24 hr).

For example, pluripotent stem cells are subjected to maintenance culture in the absence of feeder cells in a medium containing a factor for maintaining undifferentiated state before the start of step (1), a TGFβ family signal transduction pathway inhibiting substance and/or a Sonic hedgehog signal transduction pathway activating substance is/are added to the culture and culturing is continued to perform step (1). Specifically, for example, when step (1) is started after completion of maintenance culture, an undifferentiation maintenance medium added with a TGFβ family signal transduction pathway inhibiting substance and/or a Sonic hedgehog signal transduction pathway activating substance may be added or a part or all of the undifferentiation maintenance medium may be exchanged and culturing is continued.

For example, human pluripotent stem cells (e.g., human iPS cells) are subjected to a maintenance culture in the absence of feeder cells and in a serum-free medium containing bFGF. The maintenance culture is preferably performed in adhesion culture. The adhesion culture is preferably performed in a cell container with a surface coated with vitronectin, laminin 511 or E8 fragment of laminin 511. The period of maintenance culture is not particularly limited. A pluripotent stem cell is a cell capable of proliferation (preferably autonomously replicating) maintaining differentiation potency, and maintenance culture is a culture method capable of maintaining pluripotency. Thus, infinite maintenance culture is possible if properly operated. In some embodiments, during maintenance culture, pluripotent stem cells are frozen to produce a frozen cell stock, and the frozen cell stock is cultivated and maintenance culture can be continued. While the culture period after the cultivation is not particularly limited, it is, for example, about 1 day-1000 days, preferably about 7 days-150 days, more preferably about 10 days-90 days. In some embodiments, passage operation of the cells can be performed during maintenance culture.

In step (1), a TGFβ family signal transduction pathway inhibiting substance and/or a Sonic hedgehog signal transduction pathway activating substance are/is added to a medium containing human pluripotent stem cells subjected to a maintenance culture as mentioned above and culturing is continued. The TGFβ family signal transduction pathway inhibiting substance is preferably a TGFβ signal transduction pathway inhibiting substance (e.g., SB431542, A-83-01, Lefty), a Nodal/Activin signal transduction pathway inhibiting substance (e.g., SB431542, A-83-01, Lefty), a BMP signal transduction pathway inhibiting substance (e.g., LDN193189), or a combination thereof (e.g., SB431542 and LDN193189). The TGFβ family signal transduction pathway inhibiting substance is further preferably Lefty, SB431542, A-83-01, LDN193189, or a combination thereof (e.g., SB431542 and LDN193189). The Sonic hedgehog signal transduction pathway activating substance is preferably Shh protein, SAG or PMA. The TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) may be used in combination. After addition, culturing is continued for 0.5-144 hr (preferably, 2-96 hr, 6-72 hr, 6-60 hr, 12-60 hr, 18-60 hr, 18-48 hr, or 18-28 hr (e.g., 24 hr)). The TGFβ family signal transduction pathway inhibiting substance (e.g., Lefty, SB431542, A-83-01, LDN193189), the Shh signal transduction pathway activating substance (e.g., Shh protein, SAG, PMA) or a combination thereof may be changed during the culture. In one embodiment, cells can be cultured using both the TGFβ family signal transduction pathway inhibiting substance (e.g., SB431542, LDN193189) and the Shh signal transduction pathway activating substance (e.g., SAG) for 18-28 hr (e.g., 24 hr) and further cultured using either of the TGFβ family signal transduction pathway inhibiting substance (e.g., SB431542, LDN193189) and the Shh signal transduction pathway activating substance (e.g., SAG) for 18-28 hr (e.g., 24 hr). In another embodiment, cells can be cultured using either of the TGFβ family signal transduction pathway inhibiting substance (e.g., SB431542, LDN193189) and the Shh signal transduction pathway activating substance (e.g., SAG) for 18-28 hr (e.g., 24 hr) and further cultured using either or both of the TGFβ family signal transduction pathway inhibiting substance (e.g., SB431542, LDN193189) and the Shh signal transduction pathway activating substance (e.g., SAG) for 18-28 hr (e.g., 24 hr).

2-2. Step (2)

The step (2) for culturing the cells obtained in step (1) in suspension in a medium containing a Wnt signal transduction pathway inhibiting substance to form a cell aggregate is explained.

The time point when the suspension culture is started in step (2) of the present invention is the time point when the following operation is performed.

operation: operation including medium exchange of undifferentiation maintenance medium (that is, medium containing 1) a TGFβ family signal transduction pathway inhibiting substance and/or a Sonic hedgehog signal transduction pathway activating substance, and 2) a factor for maintaining undifferentiated state) used in step (1) and proceeding to suspension culture.

The medium exchange in the above-mentioned operation is exchange with a medium other than the undifferentiation maintenance medium and is not particularly limited as long as the medium is capable of inducing differentiation into the retinal cell and/or the retinal tissue of the present invention, or an intermediate thereof. For example, a medium not containing an "undifferentiation maintenance factor" such as a basal medium to be described later and the like can be mentioned. It may or may not contain a Wnt signal transduction pathway inhibiting substance at the time point of the start of step (2), that is, at the time point of medium exchange, and a Wnt signal transduction pathway inhibiting substance may be added after medium exchange as described later.

The medium (basal medium) to be used in step (2) is not particularly limited and the basal medium described in the above-mentioned section of definition can be appropriately selected. The medium to be used in step (2) may be a serum-containing medium or serum-free medium. To avoid contamination of chemically-undefined components, a serum-free medium is preferably used in the present invention. To avoid complicated preparation, for example, a serum-free medium supplemented with an appropriate amount of a commercially available serum alternative such as KSR and so on (e.g., medium of 1:1 mixture of IMDM and F-12, which is supplemented with 10% KSR, 450 µM 1-monothioglycerol and 1× Chemically Defined Lipid Concentrate, or GMEM medium supplemented with 5%-20% KSR, NEAR, pyruvic acid, 2-mercaptoethanol) is preferably used. The amount of KSR to be added to a serum-free medium in the case of human pluripotent stem cell is generally about 1% to about 30%, preferably about 2% to about 20% (e.g., about 5%, about 10%).

The medium used in step (2) contains a Wnt signal transduction pathway inhibiting substance. In step (1), pluripotent stem cells are treated with a TGFβ family signal transduction pathway inhibiting substance and/or a Sonic hedgehog signal transduction pathway activating substance, and, in step (2), the cells obtained in step (1) are subjected to suspension culture in a medium (preferably serum-free medium) containing a Wnt signal transduction pathway inhibiting substance to form a cell aggregate, whereby the quality of the aggregates is further improved, and cell aggregates maintaining an undifferentiated state and aggregates suitable for differentiation into retinal cells can be formed with high efficiency. The thus-obtained cell aggregates are expected to show characteristics of, for example, being spherical and having a smooth surface, an uncollapsed shape and dense inside.

The Wnt signal transduction pathway inhibiting substance to be used in step (2) is not particularly limited as long as it can suppress signal transduction mediated by Wnt and may be any of protein, nucleic acid, low-molecular-weight compound and the like. The signal mediated by Wnt is transduced via Wnt receptors that exist as heterodimers of Frizzled (Fz) and LRP5/6 (low-density lipoprotein receptor-related protein 5/6). Examples of the Wnt signal transduction pathway inhibiting substance include, but are not limited to, a substance that directly acts on Wnt or Wnt receptor (anti-Wnt neutralizing antibody, anti-Wnt receptor neutralizing antibody etc.), a substance that suppresses expression of gene encoding Wnt or Wnt receptor (e.g., antisense oligonucleotide, siRNA etc.), a substance that suppresses binding of Wnt receptor and Wnt (soluble Wnt receptor, dominant negative Wnt receptor etc., Wnt antagonist, Dkk1, Cerberus protein etc.), and a substance that suppresses physiological activity caused by signal transduction by Wnt receptor [low-molecular-weight compounds such as CKI-7 (N-(2-aminoethyl)-5-chloroisoquinoline-8-sulfonamide), D4476 (4-[4-(2,3-dihydro-1,4-benzodioxin-6-yl)-5-(2-pyridinyl)-1H-imidazol-2-yl]benzamide), IWR-1-endo (IWR1e) (4-[(3aR,4S,7R,7aS)-1,3,3a,4,7,7a-hexahydro-1,3-dioxo-4,7-methano-2H-isoindol-2-yl]-N-8-quinolinyl-benzamide), and IWP-2 (N-(6-methyl-2-benzothiazolyl)-2-[(3,4,6,7-tetrahydro-4-oxo-3-phenylthieno[3,2-d]pyrimidin-2-yl) thio]acetamide) and the like] and the like. One or more kinds of these may be contained as a Wnt signal transduction pathway inhibiting substance. CKI-7, D4476, IWR-1-endo (IWR1e), IWP-2 and the like are known Wnt signal transduction pathway inhibiting substances, and commercially available products and the like are appropriately available. IWR1e is preferably used as a Wnt signal transduction pathway inhibiting substance.

The concentration of the Wnt signal transduction pathway inhibiting substance only needs to be a concentration capable of inducing formation of a good cell aggregate. For example, IWR-1-endo is added to a medium such that the concentration is about 0.1 µM to about 100 µM, preferably about 0.3 µM to about 30 µM, more preferably about 1 µM to about 10 µM, further preferably about 3 µM. When a Wnt signal transduction pathway inhibiting substance other than IWR-1-endo is used, it is desirably used at a concentration exhibiting a Wnt signal transduction pathway inhibiting activity equivalent to that of IWR-1-endo at the above-mentioned concentration.

The timing of addition of a Wnt signal transduction pathway inhibiting substance to the medium is not particularly limited as long as the above-mentioned effects can be afforded, but a higher effect can be obtained when it is added earlier. A Wnt signal transduction pathway inhibiting substance is added to the medium generally within 6 days, preferably within 3 days, more preferably within 1 day, more preferably within 12 hours, from the start of the suspension culture in step (2), and further preferably at the time of the start of the suspension culture in step (2). Specifically, for example, it is possible to add a basal medium to which a Wnt signal transduction pathway inhibiting substance is added, or exchange a part or the whole of the medium into the basic medium. While the period during which the cells obtained in step (1) are treated with the Wnt signal transduction pathway inhibiting substance in step (2) is not particularly limited as long as the above-mentioned effect can be achieved, preferably, the substance is added to the medium when the suspension culture is started in step (2) and acted until the end of step (2) (immediately before addition of the BMP signal transduction pathway activating substance). Further preferably, as mentioned later, the cells are continuously exposed to the Wnt signal transduction pathway inhibiting substance even after completion of step (2) (that is, during the period of step (3)). In one embodiment, as described later, the Wnt signal transduction pathway inhibiting substance may be allowed to continuously act even after completion of step (2) (that is, during the period of step (3)) until a neuroepithelial tissue and/or a neural tissue are/is formed. Formation of a neuroepithelial tissue and/or a neural tissue can be confirmed by the above-described method.

For formation of an aggregate, a dispersing operation of the cells obtained in step (1) is first performed to give dispersed cells. The "dispersed cells" obtained by the dispersing operation refers to a state where, for example, not less than 70% of cells are single cells and not more than 30% of cells are clumps of 2-50 cells. Preferably, as the dispersed cells, a state where not less than 80% of cells are single cells, and not more than 20% of cells are clumps of 2-50 cells can be mentioned. The dispersed cells refer to a state almost free of mutual adhesion of cells (e.g., plane attachment). In some embodiments, dispersed cells refer to a state almost free of cell-cell junction (e.g., adhesive bond).

A dispersion operation of the cells obtained in step (1) may contain the above-mentioned mechanical dispersion treatment, cell dispersion solution treatment, and cell protecting agent treatment. These treatments may be performed in combination. Preferably, a cell dispersion solution treatment is performed simultaneously with a cell protecting agent treatment and then a mechanical dispersion treatment is performed.

As a cell protecting agent to be used for the cell protecting agent treatment, an FGF signal transduction pathway activating substance, serum, and serum alternative can be mentioned. Also, as a cell protecting agent to suppress cell death of pluripotent stem cells (particularly, cell death of human pluripotent stem cells) induced by dispersion, a Rho-associated coiled-coil kinase (ROCK) inhibitor or a Myosin inhibitor may be added. To suppress cell death of pluripotent stem cells (particularly, human pluripotent stem cells) induced by dispersion, and protect the cells, a Rho-associated coiled-coil kinase (ROCK) inhibitor or a Myosin inhibitor may be added from the start of the second step culture. As a ROCK inhibitor, Y-27632, Fasudil (HA1077), H-1152 and the like can be mentioned. As a Myosin inhibitor, Blebbistatin can be mentioned.

As a cell dispersion solution to be used for the cell dispersion solution treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

As a method of mechanical dispersion treatment, a pipetting treatment or scraping by a scraper can be mentioned.

The dispersed cells are suspended in the above-mentioned medium. For example, the dispersed cells are suspended in a serum-free medium containing a Wnt signal transduction pathway inhibiting substance (and a cell protecting agent such as a ROCK inhibitor and the like as necessary), whereby a treatment with a Wnt signal transduction pathway inhibiting substance is possible from the start of the suspension culture in step (2).

Then, a suspension of the dispersed cells is seeded in the above-mentioned culture vessel, and the dispersed cells are cultured under a condition non-adhesive to the culture vessel, whereby plural cells are gathered to form an aggregate.

In this case, plural cell aggregates may be simultaneously formed in one culture vessel by seeding the dispersed cells in a comparatively large culture vessel such as a 10 cm dish. However, the size of the aggregates varies in this case. Thus, for example, a given number of dispersed cells are placed in each well of a multiwell plate (U-bottom, V-bottom, M-bottom) such as a 96-well microplate, and static culture is performed, whereby the cells are rapidly aggregated to form one aggregate in each well. The aggregates are recovered from plural wells, whereby a population of uniformed aggregates can be obtained.

The concentration of the cells in step (2) can be appropriately set so that cell aggregates can be more uniformly and efficiently formed. For example, when human cells (e.g., cells obtained from human iPS in step (1)) are cultured in suspension using a 96-well microwell plate, a liquid prepared to achieve about $1\times10^3$ cells to about $1\times10^5$ cells, preferably about $3\times10^3$ cells to about $5\times10^4$ cells, more preferably about $4\times10^3$ cells to about $2\times10^4$ cells, further preferably about $4\times10^3$ cells to about $1.6\times10^4$ cells, further more preferably about $8\times10^3$ cells to about $1.2\times10^4$ cells, per well is added to the wells, and the plate is stood to form aggregates.

The culture conditions such as culture temperature, $CO_2$ concentration and so on in step (2) can be appropriately determined. The culture temperature is, for example, about 30° C. to about 40° C., preferably about 37° C. The $CO_2$ concentration is, for example, about 1% to about 10%, preferably about 5%.

In step (2), when a medium exchange operation is performed, for example, an operation to add a fresh medium without discarding the existing medium (medium addition operation), an operation to discard about a half amount of the existing medium (about 30-90%, for example, 40-60% of the volume of the existing medium) and add about a half amount of a fresh medium (30-90%, for example, about 40-60% of the volume of the existing medium) (half-medium exchange operation), and an operation to discard about the whole amount of the existing medium (not less than 90% of the amount of the existing medium) and add about the whole amount of a fresh medium (not less than 90% of the amount of the existing medium) (full-medium exchange operation) can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration, specifically 1.5 times-3.0 times the final concentration, for example, about 2 times the final concentration (half-medium exchange operation, half-medium exchange) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium exchange operation may be performed plural times per day, preferably plural times (e.g., 2-3 times) within 1 hr. Also, when the concentration of a component contained in the existing medium is to be decreased by dilution at a certain time point, the cells or aggregates may be transferred to another culture container.

While the tool used for the medium exchange operation is not particularly limited, for example, pipetter, micropipette, multichannel micropipette, continuous dispenser, and the like can be mentioned. For example, when a 96 well plate is used as a culture vessel, a multichannel micropipette may be used.

The period for suspension culture necessary for forming a cell aggregate can be determined as appropriate according to the cell to be used, so that the cells can be aggregated uniformly. To form uniformed cell aggregates, it is desirably as short as possible. The steps for the dispersed cells to form cell aggregates can be divided into a step for gathering cells, and a step for forming cell aggregates from the gathered cells. In a step of seeding the dispersed cells (i.e., at the time of the start of suspension culture) to gather the cells in case of human pluripotent stem cells (e.g., stem cells obtained from human iPS in step (1)), for example, the gathered cells are formed preferably within about 24 hr, more preferably within about 12 hr. The period from the time point of seeding the dispersed cells (i.e., at the time of the start of suspension culture) to that of forming an aggregate in the case of human pluripotent stem cells (e.g., human iPS cells), the aggregate is formed, for example, preferably within about 72 hr, more preferably within about 48 hr. The period for cell aggregate formation can be appropriately adjusted by controlling the tools for aggregating the cells, centrifugation conditions and so on.

Formation of cell aggregates and uniformity thereof can be determined based on the size and cell number of the aggregates, macroscopic morphology, microscopic morphology and uniformity thereof by tissue staining analysis, expression of markers for differentiation and undifferentiated state and uniformity thereof, control of expression of differentiation marker and synchronism thereof, reproducibility of differentiation efficiency between the aggregates, and so on.

After aggregate formation, the aggregate may be continuously cultured as it is. The period for suspension culture in step (2) is generally 24 hr-6 days, preferably 24 hr-3 days, further preferably about 24 hr-48 hr.

In one embodiment, the medium used in step (2) may further contain a Sonic hedgehog signal transduction pathway activating substance. In step (1), pluripotent stem cells are treated with a TGFβ family signal transduction pathway inhibiting substance and/or a Sonic hedgehog signal transduction pathway activating substance and, in step (2), the cells obtained in step (1) are subjected to suspension culture in a medium (preferably serum-free medium) containing a Wnt signal transduction pathway inhibiting substance and a Sonic hedgehog signal transduction pathway activating substance to form a cell aggregate, whereby it is expected that the quality of the aggregate is further improved, and cell aggregates maintaining an undifferentiated state (e.g., a spherical, smooth surfaced, uncollapsed, and dense inside aggregate of cells maintaining undifferentiated properties) can be formed with high efficiency.

As the Sonic hedgehog signal transduction pathway activating substance, those mentioned above can be used. Preferably, the Sonic hedgehog signal transduction pathway activating substance is SAG, Purmorphamine (PMA) or Shh protein. In one embodiment, a Sonic hedgehog signal transduction pathway activating substance of the same kind as that used in step (1) can be used in step (2). The concentration of the Sonic hedgehog signal transduction pathway activating substance in the medium can be appropriately determined to fall within a range capable of achieving the aforementioned effects. SAG is used at a concentration of generally 1-2000 nM, preferably 10 nM-1000 nM, more preferably 10 nM-700 nM, further preferably 50 nM-700 nM, further preferably 100 nM-600 nM, further preferably 100 nM-500 nM, in step (2). In another embodiment, SAG is used at a concentration of generally 1-2000 nM, preferably 3 nM-100 nM, more preferably 5 nM-50 nM, further preferably 10 nM-30 nM, in step (2). PMA is used at a concentration of generally 0.002-20 µM, preferably 0.02-2 µM, in step (2). Shh protein is used at a concentration of generally 20-1000 ng/ml, preferably 50-300 ng/ml, in step (2). When a Sonic hedgehog signal transduction pathway activating substance other than SAG, PMA, Shh protein is used, it is desirably used at a concentration showing a Sonic hedgehog signal transduction promoting activity equivalent to that of SAG at the above-mentioned concentration (e.g., 5 nM-50 nM).

The timing of addition of a Sonic hedgehog signal transduction pathway activating substance to the medium is not particularly limited as long as the above-mentioned effects can be afforded, but a higher effect can be obtained when it is added earlier. A Sonic hedgehog signal transduction pathway activating substance is added to the medium generally within 6 days, preferably within 3 days, more preferably within 1 day, more preferably within 12 hr, from the start of suspension culture in step (2), and further preferably at the time of the start of suspension culture in step (2). The Sonic hedgehog signal transduction pathway activating substance may be contained in the medium for any period (e.g., about 24 hr, about 48 hr, until the end of step (2)) up to the completion of step (2) (immediately before addition of a BMP signal transduction pathway activating substance). In one embodiment, a Sonic hedgehog signal transduction pathway activating substance is added simultaneously with a Wnt signal transduction pathway inhibiting substance and contained in the medium for the same period in step (2) (e.g., until the end of step (2)).

In one embodiment, the medium used in step (2) may further contain a TGFβ signal transduction pathway inhibiting substance. In step (1), pluripotent stem cells are treated with a TGFβ family signal transduction pathway inhibiting substance and/or a Sonic hedgehog signal transduction pathway activating substance and, in the second step, the cells obtained in the first step are subjected to suspension culture in a medium (preferably serum-free medium) containing a Wnt signal transduction pathway inhibiting substance and a TGFβ family signal transduction pathway inhibiting substance or a medium (preferably serum-free medium) containing a Wnt signal transduction pathway inhibiting substance, a Sonic hedgehog signal transduction pathway activating substance and a TGFβ family signal transduction pathway inhibiting substance to form a cell aggregate, whereby it is expected that the quality of the aggregate is further improved, and cell aggregates maintaining an undifferentiated state (e.g., a spherical, smooth surfaced, uncollapsed, and dense inside aggregate of cells maintaining undifferentiated properties) can be formed with high efficiency.

As the TGFβ signal transduction pathway inhibiting substance, those mentioned above can be used. Preferably, the TGFβ signal transduction pathway inhibiting substance is SB431542 or A83-01. In one embodiment, a TGFβ signal transduction pathway inhibiting substance of the same kind as that used in step (1) can be used in step (2). The concentration of the TGFβ signal transduction pathway inhibiting substance in the medium can be appropriately determined to fall within the range capable of achieving the aforementioned effect. SB431542 is used at a concentration of generally 0.1-200 µM, preferably 2-50 µM, more preferably 3-10 µM. A-83-01 is used at a concentration of generally 0.05-50 µM, preferably 0.5-5 µM. When a TGFβ signal transduction pathway inhibiting substance other than SB431542 or A-83-01 is used, it is desirably used at a concentration showing a TGFβ signal transduction pathway inhibiting activity equivalent to that of SB431542 at the above-mentioned concentration.

The timing of addition of a TGFβ signal transduction pathway inhibiting substance to the medium is not particularly limited as long as the above-mentioned effects can be afforded, but a higher effect can be obtained when it is added earlier. A TGFβ signal transduction pathway inhibiting substance is added to the medium generally within 6 days, preferably within 3 days, more preferably within 1 day, more preferably within 12 hours, from the start of the suspension culture in step (2), and further preferably at the time of the start of the suspension culture in step (2). In step (2), the TGFβ signal transduction pathway inhibiting substance is contained in the medium for any period (e.g., about 24 hr, about 48 hr, until the end of step (2)) up to the completion of step (2) (immediately before addition of the BMP signal transduction pathway activating substance). In one embodiment, a TGFβ signal transduction pathway inhibiting substance is added simultaneously with a Wnt signal transduction pathway inhibiting substance and contained in the medium for the same period (e.g., until the end of step (2)).

The medium used in step (2) may be substantially free of a TGFβ signal transduction pathway inhibiting substance. In the present specification, when the medium used in step (1) contains a TGFβ signal transduction pathway inhibiting substance, and when the concentration of the TGFβ signal transduction pathway inhibiting substance carried over from step (1) to step (2) during medium exchange (e.g., medium exchange of about total amount) is suppressed to a level at which the biological activity (namely, TGFβ signal transduction pathway inhibiting activity) thereof is not expressed (e.g., not more than 5 nM for SB431542), it can be regarded as a medium substantially free of a TGFβ signal transduction pathway inhibiting substance. In the present specification, substances other than the TGFβ signal transduction pathway inhibiting substance are also interpreted similarly. For example, by a medium exchange operation of a medium free of a TGFβ signal transduction pathway inhibiting substance, carrying over of the TGFβ signal transduction pathway inhibiting substance (e.g., SB431542) from step (1) is suppressed to not more than 3%, preferably not more than 1%, not more than 0.3%, not more than 0.1%, not more than 0.03%, or not more than 0.01% of the concentration of the TGFβ signal transduction pathway inhibiting substance (e.g., SB431542) in the medium used in step (1) and the concentration of a TGFβ signal transduction pathway inhibiting substance in the medium is suppressed to a level at which the biological activity (i.e., TGFβ signal transduction pathway inhibiting activity) thereof is not expressed (e.g., not more than 5 nM for SB431542), whereby a medium substantially free of a TGFβ signal transduction pathway inhibiting substance can be obtained. Carrying over of the component in the medium to a fresh medium can be suppressed to the minimum by, during medium exchange (e.g., medium exchange of about total amount), removing the old medium and pre-washing the cells and the culture container with a fresh medium one or plural times.

The medium used in step (2) may be substantially free of a Sonic hedgehog signal transduction pathway activating substance. In the present specification, when the medium used in step (1) contains a Sonic hedgehog signal transduction pathway activating substance, and when the concentration of the Sonic hedgehog signal transduction pathway activating substance carried over from step (1) to step (2) during medium exchange (e.g., medium exchange of about total amount) is suppressed to a level at which the biological activity (namely, Sonic hedgehog signal transduction pathway activation) thereof is not expressed (e.g., not more than 0.03 nM for SAG), it can be regarded as a medium substantially free of a Sonic hedgehog signal transduction pathway activating substance. For example, by a medium exchange operation of a medium free of a Sonic hedgehog signal transduction pathway activating substance, carrying over of the Sonic hedgehog signal transduction pathway activating substance (e.g., SAG) from step (1) is suppressed to not more than 3%, preferably not more than 1%, not more than 0.3%, not more than 0.1%, not more than 0.03%, or not more than 0.01% of the concentration of the Sonic hedgehog signal transduction pathway activating substance (e.g., SAG) in the medium used in step (1) and the concentration of a Sonic hedgehog signal transduction pathway activating substance in the medium is suppressed to a level at which the biological activity (i.e., Sonic hedgehog signal transduction pathway activation) thereof is not expressed (e.g., not more than 0.03 nM for SAG), whereby a medium substantially free of a Sonic hedgehog signal transduction pathway activating substance can be obtained. Carrying over of the component in the medium to a fresh medium can be suppressed to the minimum by, during medium exchange (e.g., medium exchange of about total amount), removing the old medium and pre-washing the cells and the culture container with a fresh medium one or plural times.

In a preferable embodiment, in step (2), the human cells obtained in step (1) (e.g., cells obtained from human iPS cells in step (1)) are subjected to suspension culture in a serum-free medium containing a Wnt signal transduction pathway inhibiting substance (e.g., CKI-7, D4476, IWR-1-endo (IWR1e), IWP-2) to form an aggregate. The medium may further contain a Sonic hedgehog signal transduction pathway activating substance (e.g., SAG, PMA, Shh protein) and/or a TGFβ signal transduction pathway inhibiting substance (e.g., Lefty, SB431542, A-83-01). The time of addition of the Wnt signal transduction pathway inhibiting substance and that of the Sonic hedgehog signal transduction pathway activating substance and/or the TGFβ signal transduction pathway inhibiting substance may be the same or different. Preferably, a Wnt signal transduction pathway inhibiting substance, a Sonic hedgehog signal transduction pathway activating substance and/or a TGFβ signal transduction pathway inhibiting substance are both preferably contained in the medium from the time of the start of suspension culture. A ROCK inhibitor (e.g., Y-27632) may also be added to the medium. The period for the culture in step (2) is 24 hr-6 days, preferably 24 hr-48 hr. The aggregates formed are preferably uniformed aggregates.

For example, the human cells obtained in step (1) (e.g., cells obtained from human iPS cells in step (1)) are recovered, dispersed to single cells or a state close thereto in a serum-free medium containing a Wnt signal transduction pathway inhibiting substance (e.g., CKI-7, D4476, IWR-1-endo (IWR1e), IWP-2), and a Sonic hedgehog signal transduction pathway activating substance (e.g., SAG, PMA, Shh protein) and/or a TGFβ signal transduction pathway inhibiting substance (e.g., Lefty, SB431542, A-83-01) and subjected to suspension culture. The serum-free medium may contain a ROCK inhibitor (e.g., Y-27632). A suspension of human pluripotent stem cells (e.g., human iPS cells) is seeded in the above-mentioned culture vessel and the dispersed pluripotent stem cells are cultured under conditions where they are non-adhesive to the culture vessel, whereby plural pluripotent stem cells are assembled to form an aggregate. The period for the culturing in step (2) is 24 hr-6 days, preferably 24 hr-48 hr. The aggregates formed are preferably uniformed aggregates.

In one preferable embodiment, in step (1), pluripotent stem cells are cultured (preferably, adhesion culture) in a medium containing a TGFβ signal transduction pathway inhibiting substance and containing or not containing a Sonic hedgehog signal transduction pathway activating substance (e.g., SAG, PMA, Shh protein) and, in step (2), the cells obtained in step (1) are subjected to suspension culture in a medium containing a Wnt signal transduction pathway inhibiting substance (e.g., CKI-7, D4476, IWR-1-endo (IWR1e), IWP-2) and containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01). Preferably, SB431542 can be used as a TGFβ signal transduction pathway inhibiting substance in step (1). The period for the culturing in step (2) is 24 hr-6 days, preferably 24 hr-48 hr. The aggregates formed are preferably uniformed aggregates.

In one preferable embodiment, in step (1), pluripotent stem cells are cultured (preferably, adhesion culture) in a medium containing a BMP signal transduction pathway inhibiting substance and containing or not containing a Sonic hedgehog signal transduction pathway activating substance (e.g., SAG, PMA, Shh protein) and, in step (2), the cells obtained in step (1) are subjected to suspension culture in a medium containing a Wnt signal transduction pathway inhibiting substance (e.g., CKI-7, D4476, IWR-1-endo (IWR1e), IWP-2) and containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01). Preferably, LDN193189 or Dorsomorphin, more preferably LDN193189, can be used as a BMP signal transduction pathway inhibiting substance in step (1). The period for the culturing in step (2) is 24 hr-6 days, preferably 24 hr-48 hr. The aggregates formed are preferably uniformed aggregates.

In one preferable embodiment, in step (1), pluripotent stem cells are cultured (preferably, adhesion culture) in a medium containing a Sonic hedgehog signal transduction pathway activating substance and containing or not containing a TGFβ signal transduction pathway inhibiting substance and/or a BMP signal transduction pathway inhibiting substance and, in step (2), the cells obtained in step (1) are subjected to suspension culture in a medium containing a Wnt signal transduction pathway inhibiting substance (e.g., CKI-7, D4476, IWR-1-endo (IWR1e), IWP-2) and containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01). Preferably, SAG can be used as a Sonic hedgehog signal transduction pathway activating substance in step (1). The period for the culturing in step (2) is 24 hr-6 days, preferably 24 hr-48 hr. The aggregates formed are preferably uniformed aggregates.

In one preferable embodiment, in step (1), pluripotent stem cells (e.g., human pluripotent stem cell) are cultured (preferably, adhesion culture) in a medium containing a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination thereof (e.g., SB431542 and LDN193189) etc.); a Sonic hedgehog signal transduction pathway activating substance (e.g., Shh protein, SAG, PMA); or a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) and, in step (2), the cells obtained in step (1) are subjected to suspension culture in a medium containing a Wnt signal transduction pathway inhibiting substance (e.g., CKI-7, D4476, IWR-1-endo (IWR1e), IWP-2) and a Sonic hedgehog signal transduction pathway activating substance (e.g., SAG, PMA, Shh protein) (in one embodiment, not containing a TGFβ signal transduction pathway inhibiting substance (e.g., SB431542, A-83-01, Lefty)), or a Wnt signal transduction pathway inhibiting substance (e.g., CKI-7, D4476, IWR-1-endo (IWR1e), IWP-2), a Sonic hedgehog signal transduction pathway activating substance (e.g., SAG, PMA, Shh protein) and a TGFβ signal transduction pathway inhibiting substance (e.g., SB431542, A-83-01, Lefty). The period for the culturing in step (2) is 24 hr-6 days, preferably 24 hr-48 hr. The aggregates formed are preferably uniformed aggregates.

In another embodiment, in step (1), pluripotent stem cells (e.g., human pluripotent stem cell) are cultured (preferably, adhesion culture) in a medium containing a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination thereof (e.g., SB431542 and LDN193189) etc.); a Sonic hedgehog signal transduction pathway activating substance (e.g., Shh protein, SAG, PMA); or a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) and, in step (2), the cells obtained in step (1) are subjected to suspension culture in a medium not containing a Sonic hedgehog signal transduction pathway activating substance (e.g., SAG, PMA, Shh protein) but containing a Wnt signal transduction pathway inhibiting substance (e.g., CKI-7, D4476, IWR-1-endo (IWR1e), IWP-2); a medium not containing a Sonic hedgehog signal transduction pathway activating substance (e.g., SAG, PMA, Shh protein) or a TGFβ signal transduction pathway inhibiting substance (e.g., SB431542, A-83-01, Lefty) but containing a Wnt signal transduction pathway inhibiting substance (e.g., CKI-7, D4476, IWR-1-endo (IWR1e), IWP-2): or a medium not containing a Sonic hedgehog signal transduction pathway activating substance (e.g., SAG, PMA, Shh protein) but containing a Wnt signal transduction pathway inhibiting substance (e.g., CKI-7, D4476, IWR-1-endo (IWR1e), IWP-2) and a TGFβ signal transduction pathway inhibiting substance (e.g., SB431542, A-83-01, Lefty). The period for the culturing in step (2) is 24 hr-6 days, preferably 24 hr-48 hr. The aggregates formed are preferably uniformed aggregates.

In another embodiment, in step (1), pluripotent stem cells (e.g., human pluripotent stem cell) are cultured (preferably, adhesion culture) in a medium containing a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) for 18 hr-30 hr (e.g., about 24 hr), after which further cultured (preferably, adhesion culture) in a medium containing a Sonic hedgehog signal transduction pathway activating substance (e.g., Shh protein, SAG, PMA) for 18 hr-30 hr (e.g., about 24 hr) and, in step (2), the cells obtained in step (1) are subjected to suspension culture in a medium not containing a Sonic hedgehog signal transduction pathway activating substance (e.g., SAG, PMA, Shh protein) but containing a Wnt signal transduction pathway inhibiting substance (e.g., CKI-7, D4476, IWR-1-endo (IWR1e), IWP-2); a medium not containing a Sonic hedgehog signal transduction pathway activating substance (e.g., SAG, PMA, Shh protein) or a TGFβ signal transduction pathway inhibiting substance (e.g., SB431542, A-83-01, Lefty) but containing a Wnt signal transduction pathway inhibiting substance (e.g., CKI-7, D4476, IWR-1-endo (IWR1e), IWP-2): or a medium not containing a Sonic hedgehog signal transduction pathway activating substance (e.g., SAG, PMA, Shh protein) but containing a Wnt signal transduction pathway inhibiting substance (e.g., CKI-7, D4476, IWR-1-endo (IWR1e), IWP-2) and a TGFβ signal transduction pathway inhibiting substance (e.g., SB431542, A-83-01, Lefty). The period for the culturing in step (2) is 24 hr-6 days, preferably 24 hr-48 hr. The aggregates formed are preferably uniformed aggregates.

In another embodiment, in step (1), pluripotent stem cells (e.g., human pluripotent stem cell) are cultured (preferably, adhesion culture) in a medium containing a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) for 18 hr-30 hr (e.g., about 24 hr), after which further cultured (preferably, adhesion culture) in a medium containing a Sonic hedgehog signal transduction pathway activating substance (e.g., Shh protein, SAG, PMA) for 18 hr-30 hr (e.g., about 24 hr) and, in step (2), the cells obtained in step (1) are subjected to suspension culture in a medium containing a Wnt signal transduction pathway inhibiting substance (e.g., CKI-7, D4476, IWR-1-endo (IWR1e), IWP-2) and containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01). The period for the culturing in step (2) is 24 hr-6 days, preferably 24 hr-48 hr. The aggregates formed are preferably uniformed aggregates.

In any embodiment, the medium in step (2) preferably contains a ROCK inhibiting substance (e.g., Y-27632).

By performing step (2) in this manner, an aggregate of the cells obtained in step (1), or the cells derived therefrom are formed. The present invention also provides a method for producing such aggregate. The aggregate obtained in step (2) has higher quality than the one formed when a treatment with a TGFβ family signal transduction pathway inhibiting substance and/or a Sonic hedgehog signal transduction pathway activating substance is not performed in step (1). To be specific, for example, a population of aggregates having a high ratio of spherical cell aggregates having a smooth surface, a dense inside, and uncollapsed shape can be obtained. In one embodiment, when aggregates (e.g., not less than 100 aggregates) are randomly selected on day 6 from the start of the second step, the sum of the ratios of uncollapsed aggregates and/or non-cystic aggregates is, for example, not less than 70%, preferably not less than 80%.

The aggregate obtained in step (2) has a potency to differentiate into a retinal cell or retinal tissue (e.g., retinal tissue, retinal progenitor cell, or retinal layer-specific neural cell).

In one embodiment, by using the stem cells obtained in step (1) and having a potency to differentiate into at least a retinal cell or a retinal tissue (e.g., retinal tissue, retinal progenitor cell, or retinal layer-specific neural cell) (e.g., Oct3/4 positive stem cells having a potency to differentiate into at least a retinal cell or a retinal tissue (e.g., retinal tissue, retinal progenitor cell, or retinal layer-specific neural cell)) in step (2), an aggregate containing stem cells (preferably Oct3/4 positive stem cells) having a potency to differentiate into at least a retinal cell or a retinal tissue (e.g., retinal tissue, retinal progenitor cell, or retinal layer-specific neural cell) can be obtained. Retinal cells and retinal tissues can be induced with high efficiency by culturing the aggregate obtained in step (2) under appropriate differentiation conditions.

In one embodiment, the aggregate obtained in step (2) contains cells corresponding to the cells in an intermediate stage between cells maintaining pluripotent-like properties (specifically, expressing Oct3/4) obtained on completion of step (1), and retinal cells or retinal tissues. These cells express any of (i) pluripotent property marker Oct3/4, and (ii) the aforementioned retinal cell marker (Rx, PAX6, Chx10, Crx, Blimp1) and/or the aforementioned retina layer-specific neural cell marker. That is, in one embodiment, the aggregate obtained in step (2) contains a mixture of cells expressing any of (i) pluripotent property marker Oct3/4, and (ii) the aforementioned retinal cell marker (Rx, PAX6, Chx10, Crx, Blimp1) and/or the aforementioned retinal layer-specific neural cell marker. That is, the aggregate obtained in step (2) contains stem cells having a potency to differentiate into at least a retinal cell or retinal tissue, and/or progenitor cells of retinal cells or retinal tissues. The progenitor cells are characterized in that they show an ability (competence) to express the aforementioned retinal cell or retina layer-specific neural cell markers when they are cultured under known appropriate culture conditions. Therefore, in one embodiment, the aggregate obtained in step (2) contains Oct3/4 positive stem cells having a potency to differentiate into at least a retinal cell or retinal tissue, and/or progenitor cells of a retinal cell or retinal tissue. A part of the cells contained in the aggregate obtained in step (2) may express the aforementioned retina layer-specific cell marker. In one embodiment, the aggregate obtained in step (2) may contain Oct3/4 positive cells at a proportion of not less than 50%, for example, not less than 70%, of the total cells.

2-3. Step (3)

Step (3) where an aggregate containing retinal cells or a retinal tissue are induced from the aggregate obtained in step (2) is explained.

The medium (basal medium) to be used in step (3) is not particularly limited, and the basal medium described in the above-mentioned definitions can be appropriately selected. The medium to be used in step (3) is, for example, a serum-free medium or a serum-containing medium (preferably serum-free medium) supplemented with a BMP signal transduction pathway activating substance.

A serum-free medium or serum-containing medium to be used for such medium is not particularly limited as long as it is as mentioned above. To avoid complicated preparation, for example, a serum-free medium supplemented with an appropriate amount of a commercially available serum alternative such as KSR and so on (e.g., medium of 1:1 mixture of IMDM and F-12 supplemented with 10% KSR, 450 μM 1-monothioglycerol and 1× Chemically Defined Lipid Concentrate) is preferably used. The amount of KSR to be added to a serum-free medium in the case of human pluripotent stem cell (e.g., iPS cell) is generally about 1% to about 20%, preferably about 2% to about 20%.

As the medium (preferably serum-free medium) to be used in step (3), the medium (preferably serum-free medium) used in step (2) may be directly used, or may be replaced with a fresh medium (preferably serum-free medium). When the serum-free medium free of a BMP signal transduction pathway substance used in step (2) is directly used for step (3), a BMP signal transduction pathway activating substance may be added to the medium.

Examples of the BMP signal transduction pathway activating substance to be used in step (3) include BMP proteins such as BMP2, BMP4, BMP7 etc., GDF proteins such as GDF7 etc., anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd. The BMP signal transduction pathway activating substance is preferably BMP4.

The concentration of the BMP signal transduction pathway activating substance may be a concentration at which differentiation of the cells forming an aggregate of pluripotent stem cells into retinal cells can be induced. For example, in the case of human BMP4, it is added to the medium to a concentration of about 0.01 nM to about 1 µM, preferably about 0.1 nM to about 100 nM, more preferably about 1 nM to about 10 nM, further preferably about 1.5 nM (55 ng/mL). When a BMP signal transduction pathway activating substance other than BMP4 is used, it is desirably used at a concentration at which a BMP signal transduction promoting activity equivalent to that of BMP4 at the above-mentioned concentration is exerted.

The concentration of the BMP signal transduction pathway activating substance in the medium may be varied during the period of step (3). For example, the BMP signal transduction pathway activating substance is provided to fall within the above-mentioned range at the time of the start of step (3), and the concentration may be gradually or stepwisely decreased at a ratio of 40-60% per 2-4 days. In one embodiment, the cells are cultured with a given concentration (e.g., about 1.5 nM) of a BMP signal transduction pathway activating substance for a given period (e.g., 4-10 days) from the start of step (3), and the concentration may be gradually or stepwisely decreased at a ratio of 40-60% per 2-4 days.

A BMP signal transduction pathway activating substance only needs to be added after about 24 hr or later from the start of the suspension culture in step (2), and may also be added to the medium within several days (e.g., within 15 days) from the start of the suspension culture. Preferably, a BMP signal transduction pathway activating substance is added to the medium at any time point between day 1 and day 15, more preferably between day 1 and day 9, day 1 and day 8, day 1 and day 7, day 1 and day 6, day 1 and day 5 or day 1 and day 4, more preferably day 1 and day 3, from the start of the suspension culture in step (2). In the present specification, "N days from the start of suspension culture in step (2)" means a period of from N days after the start of the suspension culture in step (2) (N×24 hr later) to immediately before progress of N+1 days ((N+1)×24 hr). For example, 2 days from the start of suspension culture in step (2) means 48 hr from the start of suspension culture in step (2) as the standard to immediately before progress of 72 hr.

In a specific embodiment, the medium may be partly or entirely exchanged with a medium containing BMP4 on, for example, day 1-9, preferably day 1-3, after the start of suspension culture in step (2) to adjust the final concentration of BMP4 to about 1-10 nM, and the cells may be cultured in the presence of BMP4 for, for example, about 1-12 days, preferably 2-9 days, more preferably 2-5 days. To maintain the concentration of BMP4 at the same level, the medium may be partly or entirely exchanged one or two times with a medium containing BMP4. Alternatively, as mentioned above, the concentration of BMP4 may also be stepwisely reduced.

After the addition of a BMP signal transduction pathway activating substance to the medium and the start of the differentiation induction of cells forming an aggregate into retinal cells, addition of the BMP signal transduction pathway activating substance to the medium is not necessary, and the medium may be exchanged with a serum-free medium or serum-containing medium each free of a BMP signal transduction pathway activating substance. In one embodiment, after the start of the differentiation induction into retinal cells, the concentration of the BMP signal transduction pathway activating substance in the medium is gradually or stepwisely decreased at a ratio of 40-60% per 2-4 days by exchanging the medium with a serum-free medium or a serum-containing medium, each free of a BMP signal transduction pathway activating substance. The cells in which induction of differentiation into retinal cells has been started can be confirmed by, for example, detecting the expression of retinal progenitor cell marker gene (e.g., Rx gene (alias Rax), Pax6 gene, Chx10 gene) in the cells. The aggregate formed in step (2) by using pluripotent stem cells in which a fluorescent reporter protein gene such as GFP and so on is knocked-in into the Rx gene locus is cultured in suspension in the presence of a BMP signal transduction pathway activating substance at a concentration necessary for differentiation induction into retinal cell, and fluorescence emitted from the expressed fluorescence reporter protein is detected, whereby the time point when differentiation induction into retinal cell was started can be also confirmed. As one embodiment of step (3), a step of culturing the aggregate formed in step (2) in suspension in a serum-free medium or serum-containing medium containing a BMP signal transduction pathway activating substance at a concentration necessary for differentiation induction into retinal cell, until a cell expressing retinal progenitor cell marker gene (e.g., Rx gene, Pax6 gene, Chx10 gene) begins appearing, thereby obtaining an aggregate comprising retinal progenitor cells can be mentioned.

In step (3), when a medium exchange operation is performed, for example, an operation to add a fresh medium without discarding the existing medium (medium addition operation), an operation to discard about a half amount of the existing medium (about 40-80% of the volume of the existing medium) and add about a half amount of a fresh medium (40-80% of the volume of the existing medium) (half-medium exchange operation), and an operation to discard about the whole amount of the existing medium (not less than 90% of the amount of the existing medium) and add about the whole amount of a fresh medium (not less than 90% of the amount of the existing medium) (full-medium exchange operation) can be mentioned.

When a particular component (e.g., BMP4) is added at a certain time point, for example, an operation to calculate the final concentration, to discard about a half amount of the existing medium, and to add about a half amount of a fresh medium containing a particular component at a concentration higher than the final concentration (specifically 1.5-3.0 times the final concentration, for example, about 2 times the final concentration) (half-medium exchange operation, half-medium exchange) may be performed.

When the concentration of a particular component contained in the existing medium is to be maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium exchange operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture container.

While the tool used for the medium exchange operation is not particularly limited, for example, pipetter, micropipette, multichannel micropipette, continuous dispenser, and the like can be mentioned. For example, when a 96 well plate is used as a culture vessel, a multichannel micropipette may be used.

In one embodiment, when the concentration of the Shh signal transduction pathway activating substance added to the medium in step (2) is comparatively low (e.g., not more than 300 nM, preferably not more than 30 nM, further preferably not more than 3 nM, for SAG, and a concentration conferring Shh signal transduction promoting activity equivalent to or lower than that of SAG at the above-mentioned concentration, for other Shh signal transduction pathway activating substances), medium exchange is not necessary, and a BMP signal transduction action substance (e.g., BMP4) may be added to the medium used in step (2). On the other hand, when the concentration of the Shh signal transduction pathway activating substance is comparatively high (e.g., exceeding 700 nM or not less than 1000 nM for SAG, and a concentration conferring a Shh signal transduction promoting activity equivalent to that of SAG at the above-mentioned concentration, for other Shh signal transduction pathway activating substances), it is desirable to exchange the medium to a fresh medium containing a BMP signal transduction action substance (e.g., BMP4) and free of a Shh signal transduction pathway activating substance to suppress an influence of the Shh signal transduction pathway activating substance remaining when a BMP signal transduction action substance is added.

In a preferable embodiment, the concentration of a Shh signal transduction pathway activating substance in the medium to be used in step (3) is a concentration not imparting an adverse influence on selective differentiation into a retinal progenitor cell or a retinal tissue. Concretely, it is, when calculated in terms of Shh signal transduction promoting activity of SAG, not more than 700 nM, preferably not more than 300 nM, more preferably not more than 10 nM, further preferably not more than 0.1 nM, further preferably substantially free of a Shh signal transduction pathway activating substance. The medium "substantially free of a Shh signal transduction pathway activating substance" means a medium in which the concentration of the Shh signal transduction pathway activating substance in the medium is suppressed to a level at which the biological activity thereof (i.e., Sonic hedgehog signal transduction pathway activation) is not expressed (e.g., not more than 0.03 nM for SAG). The medium "free of a Shh signal transduction pathway activating substance" also includes a medium substantially not supplemented with a Shh signal transduction pathway activating substance, for example, a medium not supplemented with a Shh signal transduction pathway activating substance at a concentration at which the biological activity thereof (i.e., Sonic hedgehog signal transduction pathway activation) is expressed, that is, a concentration imparting an adverse influence on selective differentiation into a retinal progenitor cell or a retinal tissue.

In step (3), the aggregates obtained in step (2) are cultured in the presence or absence of a Wnt signal transduction pathway inhibiting substance in a medium (preferably serum-free medium) containing a BMP signal transduction pathway activating substance (e.g., BMP4). That is, the medium used in step (3) may or may not contain, in addition to the BMP signal transduction pathway activating substance (e.g., BMP4), a Wnt signal transduction pathway inhibiting substance. In a preferable embodiment, the aggregates obtained in step (2) are cultured in the presence of a Wnt signal transduction pathway inhibiting substance in a medium (preferably serum-free medium) containing a BMP signal transduction pathway activating substance (e.g., BMP4). That is, in this embodiment, the medium (preferably serum-free medium) used in step (3) contains a BMP signal transduction pathway activating substance (e.g., BMP4), and a Wnt signal transduction pathway inhibiting substance.

As the Wnt signal transduction pathway inhibiting substance, any of the aforementioned Wnt signal transduction pathway inhibiting substances can be used. Preferably, the same kind of Wnt signal transduction pathway inhibiting substance as in step (2) is used in step (3).

The concentration of the Wnt signal transduction pathway inhibiting substance only needs to be a concentration capable of inducing a retinal progenitor cell and retinal tissue. For example, IWR-1-endo is added to a medium such that the concentration is about 0.1 μM to about 100 μM, preferably about 0.3 μM to about 30 μM, more preferably about 1 μM to about 10 μM, further preferably about 3 μM. When a Wnt signal transduction pathway inhibiting substance other than IWR-1-endo is used, it is desirably used at a concentration exhibiting a Wnt signal transduction pathway inhibiting activity equivalent to that of IWR-1-endo at the above-mentioned concentration. The concentration of the Wnt signal transduction pathway inhibiting substance in the medium of step (3) is preferably 50-150, more preferably 80-120, further preferably 90-110, when the concentration of the Wnt signal transduction pathway inhibiting substance in the medium of step (2) is 100, and more preferably equivalent to the concentration of the Wnt signal transduction pathway inhibiting substance in the medium of step (2).

The timing of addition of a Wnt signal transduction pathway inhibiting substance to the medium is not particularly limited as long as an aggregate containing a retinal cell or retinal tissue can be formed, but earlier addition is more preferable. Preferably, a Wnt signal transduction pathway inhibiting substance is added to the medium at the time of the start of step (3). More preferably, a Wnt signal transduction pathway inhibiting substance is added in step (2) and continuously contained in the medium also in step (3) (i.e., from the time of the start of step (3)). Further preferably, a Wnt signal transduction pathway inhibiting substance is added at the time of the start of suspension culture in step (2) and continuously contained in the medium also in step (3). For example, a BMP signal transduction action substance (e.g., BMP4) is added to the culture obtained in step (2) (suspension of aggregate in the medium containing a Wnt signal transduction pathway inhibiting substance).

The period of action of the Wnt signal transduction pathway inhibiting substance is not particularly limited as long as the above-mentioned effects can be afforded. Preferably, when a Wnt signal transduction pathway inhibiting substance is added at the time of the start of suspension culture in step (2), the period is 2 days to 30 days, more preferably 6 days to 20 days, 8 days to 18 days, 10 days to 18 days, or 10 days to 17 days (e.g., 10 days), with the time of the start of suspension culture in step (2) as the starting point. In another embodiment, when the Wnt signal transduction pathway inhibiting substance is added at the time of the start of suspension culture in step (2), the period of action of the Wnt signal transduction pathway inhibiting substance is preferably 3 days to 15 days (e.g., 5 days, 6 days, 7 days), more preferably 6 days to 10 days (e.g., 6 days), with the time of the start of suspension culture in step (2) as the starting point.

In one embodiment, medium used in step (3) may further contain a TGFβ signal transduction pathway inhibiting substance. Particularly, when a medium containing a TGFβ signal transduction pathway inhibiting substance is used in the suspension culture of step (2), the medium containing a TGFβ signal transduction pathway inhibiting substance is preferably used continuously in step (3) as well.

As the TGFβ signal transduction pathway inhibiting substance, any of the aforementioned TGFβ signal transduction pathway inhibiting substances can be used. Preferably, those of the same kind as the TGFβ signal transduction pathway inhibiting substance used in step (2) are used in step (3).

The concentration of the TGFβ signal transduction pathway inhibiting substance only needs to be a concentration capable of inducing a retinal progenitor cell and a retinal tissue. For example, SB431542 is generally used at a concentration of 0.1-200 μM, preferably 2-50 μM, more preferably 3-10 μM. A-83-01 is generally used at a concentration of 0.05-50 μM, preferably 0.5-5 μM. When a TGFβ signal transduction pathway inhibiting substance other than SB431542 or A-83-01 is used, it is desirably used at a concentration exhibiting a TGFβ signal transduction pathway inhibiting substance equivalent to that of SB431542 at the above-mentioned concentration. The concentration of the TGFβ signal transduction pathway inhibiting substance in the medium of step (3) is preferably 50-150, more preferably 80-120, further preferably 90-110, when the concentration of the TGFβ signal transduction pathway inhibiting substance in the medium of step (2) is 100. It is more preferably equivalent to the concentration of the TGFβ signal transduction pathway inhibiting substance in the medium of step (2).

The addition time and action period of the TGFβ signal transduction pathway inhibiting substance in the medium is not particularly limited as long as formation of an aggregate containing a retinal cell or a retinal tissue can be achieved. When a TGFβ signal transduction pathway inhibiting substance is added at the time of the start of suspension culture in step (2), it is preferably 2 days to 30 days, more preferably 6 days to 20 days, 8 days to 18 days, 10 days to 18 days, or 10 days to 17 days (e.g., 10 days), with the time of the start of suspension culture in step (2) as the starting point. In a preferable embodiment, the addition time and exposure period of the TGFβ signal transduction pathway inhibiting substance in the medium is the same as the aforementioned addition time and action period of the Wnt signal transduction pathway inhibiting substance. That is, in the embodiment, a TGFβ signal transduction pathway inhibiting substance is added to the medium simultaneously with a Wnt signal transduction pathway inhibiting substance, and contained in the medium for the same period as the Wnt signal transduction pathway inhibiting substance.

For example, in step (1), pluripotent stem cells are treated with a TGFβ family signal transduction pathway inhibiting substance and/or a Sonic hedgehog signal transduction pathway activating substance; in step (2), the cells obtained in step (1) are subjected to suspension culture in a medium (preferably serum-free medium) containing a Wnt signal transduction pathway inhibiting substance and a TGFβ family signal transduction pathway inhibiting substance or a medium (preferably serum-free medium) containing a Wnt signal transduction pathway inhibiting substance, a Sonic hedgehog signal transduction pathway activating substance and a TGFβ family signal transduction pathway inhibiting substance to form a cell aggregate; and in step (3), the aggregates obtained in step (2) are cultured in the presence of a Wnt signal transduction pathway inhibiting substance and a TGFβ signal transduction pathway inhibiting substance in a medium (preferably serum-free medium) containing a BMP signal transduction pathway activating substance (e.g., BMP4). That is, in this embodiment, the medium (preferably serum-free medium) used in step (3) contains a BMP signal transduction pathway activating substance (e.g., BMP4), a TGFβ signal transduction pathway inhibiting substance and a Wnt signal transduction pathway inhibiting substance.

In one embodiment, after suspension culture of step (3), the medium of step (3) is exchanged with a medium substantially free of an exogenous BMP signal transduction action substance and containing a Sonic hedgehog signal transduction pathway activating substance and a serum and suspension culture can be continued. In step (1), pluripotent stem cells are treated with a TGFβ family signal transduction pathway inhibiting substance and/or a Sonic hedgehog signal transduction pathway activating substance, and in step (2), the cells obtained in step (1) are subjected to suspension culture in a medium (preferably serum-free medium and optionally further containing a TGFβ signal transduction pathway inhibiting substance and/or a Sonic hedgehog signal transduction pathway activating substance) containing or not containing a Wnt signal transduction pathway inhibiting substance to form an aggregate, the aggregates obtained in step (2) are cultured in a medium (preferably serum-free medium and optionally further containing a Wnt signal transduction pathway inhibiting substance and/or a TGFβ signal transduction pathway inhibiting substance) containing a BMP signal transduction pathway activating substance (e.g., BMP4) for a given period, the medium is exchanged to a medium substantially free of an exogenous BMP signal transduction action substance (e.g., BMP4) containing a Sonic hedgehog signal transduction pathway activating substance and a serum and culturing is continued. That is, in this embodiment, after culturing in step (3), the medium is exchanged from a medium (preferably serum-free medium and optionally further containing a Wnt signal transduction pathway inhibiting substance and/or a TGFβ signal transduction pathway inhibiting substance) containing a BMP signal transduction pathway activating substance (e.g., BMP4) to a medium substantially free of an exogenous BMP signal transduction action substance and containing a Sonic hedgehog signal transduction pathway activating substance and a serum.

As the serum, for example, serum of mammals such as bovine serum, calf serum, fetal calf serum, horse serum, foal serum, foal fetal serum, rabbit serum, leveret rabbit serum, rabbit fetal serum, human serum and the like can be used. The serum is added at a concentration of about 1-30%, preferably about 3-20%, more preferably about 10%. In this embodiment, an appropriate amount of a serum alternative such as commercially available KSR and the like may be used instead of the serum.

As the Sonic hedgehog signal transduction pathway activating substance, any of the aforementioned Sonic hedgehog signal transduction pathway activating substance can be used, preferably SAG. For example, in the case of SAG, it is generally added at a concentration of about 0.1 nM-10 µM, preferably about 10 nM-1 µM, more preferably about 100 nM.

When the concentration of a BMP signal transduction action substance (e.g., BMP4) to be carried over from step (3) is suppressed to a level at which the biological activity (namely, BMP signal transduction action) thereof is not expressed (e.g., concentration of less than 0.01 nM for BMP4), it can be regarded as a medium substantially free of a BMP signal transduction action substance. For example, by a medium exchange operation with a medium free of a BMP signal transduction action substance, carrying over of the BMP signal transduction action substance (e.g., BMP4) from step (3) is suppressed to not more than 3%, preferably not more than 1%, not more than 0.3%, not more than 0.1%, not more than 0.03% or not more than 0.01% of the concentration of the BMP signal transduction action substance (e.g., BMP4) in the medium used in step (3), and the concentration of a BMP signal transduction action substance in the medium is suppressed to a level at which the biological activity (i.e., BMP signal transduction action) thereof is not expressed (e.g., concentration of BMP4 is less than 0.01 nM), whereby a medium substantially free of a BMP signal transduction action substance can be obtained.

In one embodiment, exchange to a medium substantially free of an exogeneous BMP signal transduction action substance and containing a Sonic hedgehog signal transduction pathway activating substance and a serum is performed after 7 days, more preferably after 9 days (for example, 10 days), from the start of suspension culture (step (2)). Here, exchange to a medium containing a Sonic hedgehog signal transduction pathway activating substance and a serum may also be performed when the formation of the neuroepithelium is started. Formation of the neuroepithelium can be confirmed by observing the sequence. morphology of the cells by bright field image observation using a microscope. In one embodiment, the cells are cultured for 3 days to 20 days, preferably 5 days to 15 days, 7 days to 10 days, after exchange to a medium containing a Sonic hedgehog signal transduction pathway activating substance and a serum.

In the method of the present invention, suspension culture is preferably performed through step (2) and step (3) in the absence of a basement membrane preparation.

The culture conditions such as culture temperature, $CO_2$ concentration and so on in step (3) can be appropriately determined. The culture temperature is, for example, about 30° C. to about 40° C., preferably about 37° C. The $CO_2$ concentration is, for example, about 1% to about 10%, preferably about 5%.

By such culture, differentiation of the cells forming the aggregate obtained in step (2) into retinal progenitor cells is induced, whereby an aggregate containing the retinal progenitor cells can be obtained. The present invention also provides a method for producing such aggregate containing retinal progenitor cell. That an aggregate comprising retinal progenitor cells was obtained can be confirmed by, for example, detecting the presence of cells expressing Rax, PAX6 or Chx10, which is a retinal progenitor cell marker, in the aggregate. One embodiment of step (3) is a step of culturing the aggregate formed in step (2) in suspension in a serum-free medium or serum-containing medium containing a BMP signal transduction pathway activating substance at a concentration necessary for differentiation induction into retinal cell, until a cell expressing Rx gene begins appearing, whereby obtaining an aggregate comprising retinal progenitor cells. In one embodiment, the culturing of step (3) is performed until not less than 20% (preferably, not less than 30%, not less than 40%, not less than 50%, not less than 60%, not less than 70%, not less than 80%, not less than 90%) of the cells contained in the aggregate express Rx. In this embodiment, the Rx expressing cell preferably coexpresses Chx10.

In one embodiment, the aggregate obtained in step (3) contains a retinal tissue and is substantially free of non-neural head ectoderm. In an aggregate containing a retinal tissue and substantially free of non-neural head ectoderm, for example, an Rx-positive tissue is observed and an Rx-negative tissue is not observed on the outside thereof in the immunostaining images of the aforementioned aggregate cryosection.

In a preferable embodiment of producing a retinal cell and/or a retinal tissue, in step (1), human pluripotent stem cells (e.g., human iPS cell) are subjected to adhesion culture in the absence of feeder cells in a serum-free medium containing a TGFβ signal transduction pathway inhibiting substance (e.g., SB431542, A-83-01) and bFGF for preferably 2-96 hr, 6-72 hr, 6-60 hr, 12-60 hr, 18-60 hr, 18-48 hr or 18-28 hr (e.g., 24 hr), and in step (2), the cells obtained in step (1) are subjected to suspension culture in the presence of a Wnt signal transduction pathway inhibiting substance (e.g., CKI-7, D4476, IWR-1-endo (IWR1e), IWP-2) in a serum-free medium not containing or containing a Sonic hedgehog signal transduction pathway activating substance (e.g., SAG, PMA, Shh protein), and in step (3), the aggregates are subjected to suspension culture in a serum-free medium containing a Wnt signal transduction pathway inhibiting substance (e.g., CKI-7, D4476, IWR-1-endo (IWR1e), IWP-2) and a BMP signal transduction pathway activating substance (e.g., BMP4).

In a preferable embodiment of producing a retinal cell and/or a retinal tissue, in step (1), human pluripotent stem cells (e.g., human iPS cell) are subjected to adhesion culture in the absence of feeder cells in a serum-free medium containing a BMP signal transduction pathway inhibiting substance (e.g., LDN193189) and bFGF for preferably 2-96 hr, 6-72 hr, 6-60 hr, 12-60 hr, 18-60 hr, 18-48 hr or 18-28 hr (e.g., 24 hr), and in step (2), the cells obtained in step (1) are subjected to suspension culture in the presence of a Wnt signal transduction pathway inhibiting substance (e.g., CKI-7, D4476, IWR-1-endo (IWR1e), IWP-2) in a serum-free medium not containing or containing a Sonic hedgehog signal transduction pathway activating substance (e.g., SAG, PMA), and in step (3), the aggregates are subjected to suspension culture in a serum-free medium containing a Wnt signal transduction pathway inhibiting substance (e.g., CKI-7, D4476, IWR-1-endo (IWR1e), IWP-2) and a BMP signal transduction pathway activating substance (e.g., BMP4).

In a preferable embodiment in the production of retinal progenitor cells and/or retinal tissues, human pluripotent stem cells (e.g., human iPS cells) are subjected to adhesion culture in the absence of feeder cells in a serum-free medium containing a Sonic hedgehog signal transduction pathway activating substance (e.g., SAG, PMA) and bFGF for preferably 2-96 hr, 6-72 hr, 6-60 hr, 12-60 hr, 18-60 hr, 18-48 hr, or 18-28 hr (e.g., for 24 hr) in step (1) and in step (2), the cells obtained in step (1) are subjected to suspension culture in the presence of a Wnt signal transduction pathway inhibiting substance (e.g., CKI-7, D4476, IWR-1-endo (IWR1e), IWP-2) in a serum-free medium not containing or containing a Sonic hedgehog signal transduction pathway activating substance (e.g., SAG, PMA), and in step (3), the aggregates are subjected to suspension culture in a serum-free medium containing a Wnt signal transduction pathway inhibiting substance (e.g., CKI-7, D4476, IWR-1-endo (IWR1e), IWP-2) and a BMP signal transduction pathway activating substance (e.g., BMP4).

In a preferable embodiment in the production of retinal cells and/or retinal tissues, human pluripotent stem cells (e.g., human iPS cells) are subjected to adhesion culture in the absence of feeder cells in a serum-free medium containing a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination of these (e.g., SB431542 and LDN193189) etc.); a Sonic hedgehog signal transduction pathway activating substance (e.g., Shh protein, SAG, PMA); or a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) in combination; and bFGF in step (1), in step (2), the cells obtained in step (1) are subjected to suspension culture in a serum-free medium containing a Wnt signal transduction pathway inhibiting substance (e.g., CKI-7, D4476, IWR-1-endo (IWR1e), IWP-2) (containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01)) to form a cell aggregate, and in step (3), the aggregates are subjected to suspension culture in a serum-free medium containing a Wnt signal transduction pathway inhibiting substance (e.g., CKI-7, D4476, IWR-1-endo(IWR1e), IWP-2) and a BMP signal transduction pathway activating substance (e.g., BMP4) (containing or containing a TGFβ signal transduction pathway inhibiting substance (e.g., Lefty, SB431542, A-83-01)) to give an aggregate containing a retinal cell (e.g., retinal progenitor cell, retinal layer-specific neural cell) or retinal tissue.

The medium in step (2) preferably contains a ROCK inhibiting substance (e.g., Y-27632).

In a preferable embodiment in the production of retinal cells and/or retinal tissues, human pluripotent stem cells (e.g., human iPS cells) are subjected to adhesion culture in the absence of feeder cells in a serum-free medium containing a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) in combination; and bFGF for 18 hr-30 hr (e.g., about 24 hr) and thereafter adhesion culture in a serum-free medium containing a Sonic hedgehog signal transduction pathway activating substance (e.g., Shh protein, SAG, PMA) and bFGF for 18 hr-30 hr (e.g., about 24 hr), in step (2), the cells obtained in step (1) are subjected to suspension culture in a serum-free medium containing a Wnt signal transduction pathway inhibiting substance (e.g., CKI-7, D4476, IWR-1-endo (IWR1e), IWP-2) (containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01)) to form a cell aggregate, and in step (3), the aggregates are subjected to suspension culture in a serum-free medium containing a Wnt signal transduction pathway inhibiting substance (e.g., CKI-7, D4476, IWR-1-endo(IWR1e), IWP-2) and a BMP signal transduction pathway activating substance (e.g., BMP4) (containing or containing a TGFβ signal transduction pathway inhibiting substance (e.g., Lefty, SB431542, A-83-01)) to give an aggregate containing a retinal cell (e.g., retinal progenitor cell, retinal layer-specific neural cell) or retinal tissue.

The medium in step (2) preferably contains a ROCK inhibiting substance (e.g., Y-27632).

In a preferable embodiment in the production of retinal cells and/or retinal tissues, human pluripotent stem cells (e.g., human iPS cells) are subjected to adhesion culture in the absence of feeder cells in a serum-free medium containing a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination of these (e.g., SB431542 and LDN193189) etc.); a Sonic hedgehog signal transduction pathway activating substance (e.g., Shh protein, SAG, PMA); or a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) in combination; and bFGF in step (1), in step (2), the cells obtained in step (1) are subjected to suspension culture in a serum-free medium or a serum-free medium containing a Wnt signal transduction pathway inhibiting substance (e.g., CKI-7, D4476, IWR-1-endo (IWR1e), IWP-2) (containing or not containing a Sonic hedgehog signal transduction pathway activating substance (e.g., SAG, PMA, Shh protein) and/or a TGFβ signal transduction pathway inhibiting substance (e.g., Lefty, SB431542, A-83-01)) to form a cell aggregate, and in step (3), the aggregates are subjected to suspension culture in a serum-free medium containing a Wnt signal transduction pathway inhibiting substance (e.g., CKI-7, D4476, IWR-1-endo(IWR1e), IWP-2) and a BMP signal transduction pathway activating substance (e.g., BMP4) for 10 days, and the medium was exchanged to a medium not containing an exogeneous BMP signal transduction action substance (e.g., BMP4) and containing a Sonic hedgehog signal transduction pathway activating substance (e.g., SAG) and a serum and the suspension culture was continued to give an aggregate containing a retinal cell (e.g., retinal progenitor cell, retinal layer-specific neural cell) or retinal tissue.

The medium in step (2) preferably contains a ROCK inhibiting substance (e.g., Y-27632).

In a preferable embodiment in the production of retinal cells and/or retinal tissues, human pluripotent stem cells (e.g., human iPS cells) are subjected to adhesion culture in the absence of feeder cells in a serum-free medium containing a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination of these (e.g., SB431542 and LDN193189) etc.); a Sonic hedgehog signal transduction pathway activating substance (e.g., Shh protein, SAG, PMA); or a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) in combination; and bFGF in step (1), in step (2), the cells obtained in step (1) are subjected to suspension culture in the presence of a Wnt signal transduction pathway inhibiting substance (e.g., CKI-7, D4476, IWR-1-endo (IWR1e), IWP-2) in a serum-free medium containing a Sonic hedgehog signal transduction pathway activating substance (e.g., SAG, PMA, Shh protein) and/or a TGFβ signal transduction pathway inhibiting substance (e.g., SB431542, A-83-01, Lefty) to form a cell aggregate, and in step (3), the aggregates are subjected to suspension culture in the presence of a Wnt signal transduction pathway inhibiting substance (e.g., CKI-7, D4476, IWR-1-endo(IWR1e), IWP-2) and a BMP signal transduction pathway activating substance (e.g., BMP4) in a serum-free medium containing a TGFβ signal transduction pathway inhibiting substance (e.g., SB431542, A-83-01, Lefty) to give an aggregate containing a retinal cell (e.g., retinal progenitor cell, retinal layer-specific neural cell) or retinal tissue.

The medium in step (2) preferably contains a ROCK inhibiting substance (e.g., Y-27632).

The obtained aggregate containing retinal progenitor cells may be used as it is as a reagent for evaluating toxicity or efficacy. An aggregate containing retinal progenitor cells is subjected to a dispersion treatment (e.g., trypsin/EDTA treatment or papain treatment), and the obtained cells are subjected to a selection using FACS or MACS, whereby highly pure retinal progenitor cells can also be obtained.

Furthermore, the aggregate containing the retinal progenitor cell obtained by the aforementioned step (1)-step (3) may be continuously cultured in a serum-free medium or serum-containing medium to make the retinal progenitor cell further differentiate, whereby a neuroepithelial structure-like retinal tissue may be produced.

Such medium (basal medium) is not particularly limited, and the basal medium described in the above-mentioned definition can be appropriately selected. A serum-free medium or serum-containing medium to be used for such medium is not particularly limited as long as it is as mentioned above. For example, a serum-containing medium which is a DMEM-F12 medium supplemented with 10% fetal bovine serum, N2 supplement, 100 μM taurine, and 500 nM retinoic acid, or a serum-free medium supplemented with an appropriate amount of a commercially available serum alternative such as KSR and so on (e.g., medium of 1:1 mixture of IMDM and F-12 supplemented with 10% KSR, 450 μM 1-monothioglycerol and 1× Chemically Defined Lipid Concentrate) and the like can be mentioned.

While the period of the culture for inducing a retinal tissue from retinal progenitor cells varies depending on the intended retinal layer-specific neural cell, it is, for example, about 7 days to about 200 days.

The retinal tissue exists covering the surface of the aggregate. After completion of the suspension culture, the aggregate may be fixed with a fixative such as para-formaldehyde solution and so on, and a cryosection is prepared, then formation of a retinal tissue having a layer structure may be confirmed by immunostaining and the like. Since respective layers of a retinal tissue are composed of different retinal progenitor cell (photoreceptor cell, horizontal cell, bipolar cell, amacrine cell, retinal ganglion cell), formation of a layer structure can be confirmed using antibodies against the aforementioned markers expressed in these cells by the immunostaining. In one embodiment, the retinal tissue is an Rx- or Chx10-positive neuroepithelial structure.

The retinal tissue existing on the surface of the aggregate can be physically excised from the aggregate by using tweezers and the like. In this case, since a neural tissue other than the retinal tissue may be formed on the surface of each aggregate, a part of the neural tissue excised from the aggregate may be cut out and subjected to confirmation by the below-mentioned immunostaining and the like, whereby the tissue can be confirmed to be a retinal tissue.

In one embodiment, the aggregate obtained in step (3) contains a retinal tissue and is substantially free of non-neural head ectoderm. In an aggregate containing a retinal tissue and substantially free of non-neural head ectoderm, for example, an Rx-positive tissue is observed and an Rx-negative tissue is not observed on the outside thereof in the immunostaining images of the aforementioned aggregate cryosection.

One embodiment of step (3) is a step of culturing the aggregate formed in step (2) in suspension in a serum-free medium or serum-containing medium (as mentioned above, optionally containing a Wnt signal transduction pathway inhibiting substance and/or a TGFβ signal transduction pathway inhibiting substance) containing a BMP signal transduction pathway activating substance (e.g., BMP4) at a concentration necessary for differentiation induction into retinal cells, until a cell expressing Rx gene and/or Chx10 gene begins appearing to give an aggregate comprising retinal progenitor cells, and subsequently culturing the aggregate containing the retinal progenitor cells in suspension in a serum-free medium or serum-containing medium until a retinal tissue is formed, whereby obtaining an aggregate comprising a retinal tissue. When the aggregate containing the retinal progenitor cells is subsequently cultured in suspension in a serum-free medium or serum-containing medium until a retinal tissue is formed, the concentration of the BMP signal transduction pathway activating substance in the medium in order to induce retinal progenitor cells may be gradually or stepwisely decreased at a ratio of 40-60% per 2-4 days by exchanging the medium with a serum-free medium or a serum-containing medium, each free of a BMP signal transduction pathway activating substance (e.g., BMP4). In this case, the concentration of the Wnt signal transduction pathway inhibiting substance and/or the TGFβ signal transduction pathway inhibiting substance may be decreased at the same proportion as in the BMP signal transduction pathway activating substance, and preferably maintained at a constant level. In one embodiment, suspension culture of an aggregate containing retinal progenitor cells is performed until not less than 20% (preferably, not less than 30%, not less than 40%, not less than 50%, not less than 60%, not less than 70%, not less than 80%, not less than 90%) of the cells contained in the aggregate expresses Chx10.

In one embodiment of step (3), the aggregate obtained in step (2), or an aggregate obtained by culturing the aggregate obtained in step (2) in suspension by the above-mentioned method may be subjected to adhesion culture to form an adhered aggregate. The adhered aggregate is cultured in an adhered state in a serum-free medium or serum-containing medium containing a BMP signal transduction pathway activating substance at a concentration necessary for differentiation induction into a retinal cell (the medium optionally contains a Wnt signal transduction pathway inhibiting substance and/or a TGFβ signal transduction pathway inhibiting substance), until a cell expressing Rx gene and/or Chx10 gene begins appearing to give an adhered aggregate containing retinal progenitor cells. The aggregate containing the retinal progenitor cells is continuously cultured in an adhered state in a serum-free medium or serum-containing medium until a retinal tissue is formed, whereby an aggregate containing a retinal tissue is obtained. In one embodiment, adhesion culture of the aggregate containing retinal progenitor cells is performed until not less than 10% (preferably, not less than 20%, not less than 30%, not less than 40%, not less than 50%, not less than 60%, not less than 70%, not less than 80%, not less than 90%) of the cells express Chx10.

By the production method of the present invention, a retinal tissue can be obtained from pluripotent stem cells with high efficiency. Since the retinal tissue obtained by the production method of the present invention contains neurons (neuronal cell) specific to each of the retinal layers, it is also possible to obtain cells constituting a retinal tissue, such as photoreceptor cell, horizontal cell, bipolar cell, amacrine cell, retinal ganglion cell or a progenitor/precursor cell thereof and the like. Which cell was obtained from the obtained retinal tissue can be confirmed by a method known per se, for example, expression of a cell marker.

The obtained aggregate containing a retinal tissue may also be directly used as a reagent for evaluating toxicity or efficacy. An aggregate containing a retinal tissue is subjected to a dispersion treatment (e.g., trypsin/EDTA treatment), and the obtained cells are subjected to a selection using FACS or MACS, whereby highly pure retinal tissue-constituting cells, for example, highly pure photoreceptor cells, can also be obtained.

A retinal tissue containing a ciliary marginal zone-like structure can be produced from a cell aggregate containing the retinal tissue obtained by the production method of the present invention, namely, the aforementioned step (1)-step (3), by a known method (e.g., WO 15/087614), specifically, the following step (A) and step (B).

In one embodiment, a ciliary marginal zone-like structure can be produced by the following step (A) and step (B) from a cell aggregate containing the retinal tissue on days 6-30, days 10-20 (day 10, day 11, day 12, day 13, day 14, day 15, day 16, day 17, day 18, day 19 or day 20) from the start of suspension culture of step (2), which aggregate is a cell aggregate containing the retinal tissue obtained by steps (1)-(3).

The ciliary marginal zone-like structure in the present specification refers to a structure similar to a ciliary marginal zone. Examples of the "ciliary marginal zone (CMZ)" include a tissue present in the boundary region of a retinal tissue (specifically, neural retina) and retinal pigment epithelium in the retina in vivo, which is a region containing tissue stem cells of retina (retinal stem cells). Ciliary marginal zone is also called a ciliary margin or retinal margin, and the ciliary marginal zone, ciliary margin and retinal margin are equivalent tissues. It is known that the ciliary marginal zone plays an important role in the supply of retinal progenitor cells or differentiated cells to retinal tissues, maintenance of retinal tissue structure and so on. Examples of the marker gene of the ciliary marginal zone include Rdh10 gene (positive), Otx1 gene (positive), Zic1 (positive) and so on.

Step (A) comprises culturing a cell aggregate comprising a retinal tissue obtained by the production method of the present invention, i.e., step (1)-step (3), in which Chx10 positive cells are present in a proportion of 20% or more and 100% or less of the retinal tissue, in a serum-free medium or serum-containing medium each containing a Wnt signal pathway activating substance and/or an FGF signal pathway inhibiting substance for only a period before the appearance of a RPE65 gene-expressing cell.

As a preferable culture of step (A) here, suspension culture can be mentioned.

As a serum-free medium to be used in step (A), a serum-free medium which is a basal medium supplemented with N2 or KSR can be mentioned. More specifically, a serum-free medium which is a DMEM/F-12 medium supplemented with N2 supplement (Life Technologies) can be mentioned. As the serum-containing medium, a serum-containing medium which is a basal medium supplemented with fetal bovine serum can be mentioned.

The culture conditions of step (A) such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

In step (A), when the above-mentioned "cell aggregate comprising a retinal tissue" is cultured in the medium, the Wnt signal transduction pathway activating substance to be contained in a serum-free medium or serum-containing medium is not particularly limited as long as it can enhance signal transduction mediated by Wnt. Specific examples of the Wnt signal transduction pathway activating substance include a protein belonging to Wnt family (e.g., Wnt1, Wnt3a, Wnt7a), Wnt receptor, Wnt receptor agonist, GSK3β inhibitor (e.g., 6-Bromoindirubin-3'-oxime (BIO), CHIR99021, Kenpaullone) and so on.

The concentration of the Wnt signal transduction pathway activating substance to be contained in a serum-free medium or serum-containing medium in step (A) in the case of a common Wnt signal transduction pathway activating substance such as CHIR99021 is, for example, in the range of about 0.1 µM to about 100 µM, preferably, for example, in the range of about 1 µM to about 30 µM, more preferably, for example, around 3 µM.

The FGF signal transduction pathway inhibiting substance to be contained in a serum-free medium or serum-containing medium in step (A) when the above-mentioned "cell aggregate comprising a retinal tissue" is cultured in the medium is not particularly limited as long as it can inhibit signal transduction mediated by FGF. Examples of the FGF signal transduction pathway inhibiting substance include FGF receptor, FGF receptor inhibitor (e.g., SU-5402, AZD4547, BGJ398), MAP kinase cascade inhibiting substance (e.g., MEK inhibitor, MAPK inhibitor, ERK inhibitor), PI3 kinase inhibitor, Akt inhibitor and so on.

The concentration of the FGF signal transduction pathway inhibiting substance contained in a serum-free medium or serum-containing medium in step (A) only needs to be a concentration at which differentiation of an aggregate into ciliary marginal zone-like structure can be induced. For example, in the case of SU-5402, it is added to the medium to a concentration of about 0.1 µM to about 100 µM, preferably about 1 µM to about 30 µM, more preferably about 5 µM.

"Culturing for only a period before the appearance of a RPE65 gene-expressing cell" in step (A) means culturing only in the whole or a part of the period before the appearance of a RPE65 gene-expressing cell. That is, culturing only in the whole or a part of the period (any period) suffices, during which the aforementioned "cell aggregate comprising a retinal tissue" present in the culture system is constituted by cells that do not substantially express RPE65 gene. By employing such culturing, a cell aggregate in which a RPE65 gene-expressing cell does not appear can be obtained.

To determine such particular period, the aforementioned "cell aggregate comprising a retinal tissue" is used as a sample, and the presence or absence of expression of RPE65 gene contained in the sample or the level thereof may be measured by a general genetic engineering method or a biochemical method. Specifically, for example, the presence or absence of expression of RPE65 gene or the level thereof can be examined by subjecting a cryosection of the aforementioned "cell aggregate comprising a retinal tissue" to an immunostaining method using an antibody against RPE65 protein.

As a "period before the appearance of a RPE65 gene-expressing cell" in step (A), for example, a period during which the ratio of Chx10 positive cells present in the above-mentioned retinal tissue decreases than that at the time of start of the culture of the aforementioned cell aggregate in a serum-free medium or serum-containing medium each containing a Wnt signal transduction pathway activating substance and/or an FGF signal transduction pathway inhibiting substance, and falls within the range of 30% to 0% can be mentioned. As the "cell aggregate in which a RPE65 gene-expressing cell does not appear", a cell aggregate in which Chx10 positive cells are present in the above-mentioned retinal tissue in a proportion of within 30% to 0% of the tissue can be mentioned.

While the number of days of the "period before the appearance of a RPE65 gene-expressing cell" in step (A) varies depending on the kind of the Wnt signal transduction pathway activating substance and/or the FGF signal transduction pathway inhibiting substance, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days (e.g., within 10 days from about day 20, with the start of step (2) as the starting point), more preferably, for example, 3 days to 6 days. When a serum-containing medium (e.g., serum-containing medium which is a basal medium supplemented with fetal bovine serum) is used, the aforementioned period is preferably, for example, within 12 days (e.g., within 12 days from about day 20, with the start of step (2) as the starting point), more preferably, for example, 6 days to 9 days.

Then as step (B), the "cell aggregate in which a RPE65 gene-expressing cell does not appear" obtained by culturing as mentioned above is cultured in a serum-free medium or serum-containing medium each free of a Wnt signal transduction pathway activating substance.

As a preferable culture in step (B), suspension culture can be mentioned.

The serum-free medium of step (B) is preferably free of an FGF signal transduction pathway inhibiting substance.

As the serum-free medium in step (B), a medium which is a basal medium supplemented with N2 or KSR can be mentioned. As the serum-containing medium, a medium which is a basal medium supplemented with fetal bovine serum can be mentioned. More specifically, a serum-containing medium which is a DMEM/F-12 medium supplemented with fetal bovine serum can be mentioned.

The above serum-free medium or serum-containing medium in step (B) may contain a known growth factor, an additive and a chemical substance that promote the growth, and so on. Examples of the known growth factor include EGF, FGF, IGF, insulin and so on. Examples of the additive that promotes the growth include N2 supplement (Life Technologies), B27 supplement (Life Technologies), KSR (Life Technologies) and so on. Examples of the chemical substance that promotes the growth include retinoids (e.g., retinoic acid) and taurine.

A preferable period for the culturing in step (B) is, for example, a period for the culturing during which the ratio of Chx10 positive cells present in the above-mentioned retinal tissue increases than that at the time of start of the culturing of the aforementioned cell aggregate in a serum-free medium or serum-containing medium each free a Wnt signal transduction pathway activating substance, and reaches 30% or more. Specifically, for example, it is 3 days-60 days, preferably about 35 days, from day about 3, with the start of step (A) as the starting point.

The culture conditions such as culture temperature, $CO_2$ concentration and the like in step (B) can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

While the number of the above-mentioned culture days until "a cell aggregate comprising a ciliary marginal zone-like structure" is obtained in step (B) varies depending on the kind of the serum-free medium or serum-containing medium, other culture conditions and so on, it is, for example, within 100 days. The above number of culture days is preferably, for example, 20 days to 70 days, more preferably, for example, 30 days to 60 days.

In a "cell aggregate comprising a ciliary marginal zone-like structure" prepared by the aforementioned step (A), (B), a retinal pigment epithelium and a retinal tissue (specifically, neural retina) are present adjacent to the ciliary marginal zone-like structure in the same cell aggregate. The structure can be confirmed by microscopic observation and so on. Specifically, for example, the presence of a ciliary marginal zone-like structure as an epithelial structure having a thick retina side and a thin retinal pigment epithelium side, which is formed between a retinal tissue having high transparency and retinal pigment epithelium showing pigmentation, can be confirmed by microscopic observation. In addition, the presence of ciliary marginal zone-like structure can be confirmed by identifying Rdh10 positive, Otx1 positive, or Zic1 positive cells with immunostaining a cryosection of aggregate.

In a further embodiment, differentiation of a retinal tissue (neuroepithelium) contained in the aggregate by the aforementioned steps (A), (B) proceeds, and a mature retinal tissue and the aforementioned cells containing at least one, preferably plural, more preferably all, cells selected from the group consisting of photoreceptor precursor cell, photoreceptor cell, cone photoreceptor cell, rod photoreceptor cell, horizontal cell, interneuron (amacrine cell, ganglion cell etc.) can be produced.

A retinal tissue containing a retinal pigment epithelial cell can be produced by the following step (C) from a cell aggregate containing a retinal tissue obtained by the production method, i.e., the aforementioned step (1)-step (3), of the present invention and the like. A retinal pigment epithelial sheet can be produced by the following step (D) from a retinal pigment epithelial cell obtained by the following step (C).

The "retinal pigment epithelial cell" in the present invention means an epithelial cell present on the outside of the neural retinal tissue in retina in vivo. Whether it is a retinal pigment epithelial cell can be confirmed by those of ordinary skill in the art based on, for example, expression of a cell marker (RPE65 (matured retinal pigment epithelial cell), Mitf (juvenile or matured retinal pigment epithelial cell) and the like), the presence of melanin granule, characteristic cell morphology of polygon and the like.

First, in step (C), a cell aggregate containing a retinal tissue obtained by the production method of the present invention is cultured in suspension in a serum-free medium or serum-containing medium free of a BMP signal transduction pathway activating substance but containing a Wnt signal transduction pathway activating substance to give an aggregate containing retinal pigment epithelial cells.

As a serum-free medium to be used in step (C), a serum-free medium which is a basal medium supplemented with N2 or KSR can be mentioned. More specifically, a serum-free medium which is a DMEM/F-12 medium supplemented with N2 supplement (Life Technologies) can be mentioned. As the serum-containing medium, a serum-containing medium which is a basal medium supplemented with fetal bovine serum can be mentioned.

The serum-free medium to be used in step (C) may contain, in addition to the aforementioned Wnt signal transduction pathway activating substance, the aforementioned Nodal/Activin signal transduction pathway activating substance, and/or the aforementioned FGF signal transduction pathway inhibiting substance.

A preferable culture in step (C) is, for example, suspension culture.

Step (D) in which the aggregate obtained in step (C) of the present invention is dispersed and the obtained cells are cultured in an adhered state is explained.

Step (D) is performed within 60 days, preferably within 30 days, more preferably 3 days, after the start of step (C).

The medium (basal medium) in step (D) is not particularly limited, and the basal medium described in the above-mentioned definition can be appropriately selected. As a serum-free medium or serum-containing medium to be used for adhesion culture in step (D), the aforementioned medium can be mentioned. To avoid complicated preparation, a serum-free medium supplemented with an appropriate amount of a commercially available serum alternative such as KSR and the like (e.g., a medium of 1:1 mixture of DMEM/F-12 and Neurobasal supplemented with 1/2×N2 supplement, 1/2×B27 supplement and 100 μM 2-mercaptoethanol) is preferably used. The amount of KSR to be added to the serum-free medium is, for example, generally about 1% to about 20%, preferably about 2% to about 20%, in the case of a cell derived from human iPS cell.

In step (D), it is preferable to culture cells in the aforementioned serum-free medium or serum-containing medium containing a ROCK inhibiting substance.

In step (D), it is more preferable to culture cells in a serum-free medium or serum-containing medium further containing one or more substances selected from the group consisting of a Wnt signal transduction pathway activating substance, an FGF signal transduction pathway inhibiting substance, an Activin signal transduction pathway activating substance and a BMP signal transduction pathway activating substance.

The Activin signal transduction pathway activating substance is a substance capable of enhancing a signal mediated by Activin. Examples of the Activin signal transduction pathway activating substance include proteins belonging to the Activin family (e.g., Activin A, Activin B, Activin C, Activin AB and the like), Activin receptor, and Activin receptor agonist.

The concentration of the Activin signal transduction pathway activating substance to be used in step (D) may be any concentrations as long as a uniformed sheet of retinal pigment epithelial cells can be efficiently formed. For example, Recombinant Human/Mouse/Rat Activin A (R&D systems, #338-AC) is added to a concentration of about 1 ng/ml to about 10 μg/ml, preferably about 10 ng/ml to about 1 μg/ml, more preferably about 100 ng/ml. An Activin signal transduction pathway activating substance is added, for example, within 18 days, preferably on day 6, from the start of step (D).

In step (D), adhesion culture is preferably performed on a culture vessel whose surface is treated with a culture substrate. As a culture substrate to be used for treating culture vessel in step (D), a cell culture substrate enabling adhesion culture of aggregate-derived cells and formation of a retinal pigment epithelial sheet can be mentioned.

As mentioned above, the production method of a retinal cell or retinal tissue containing step (A) and step (B) or step (C) and step (D) in addition to the above-mentioned step (1)-step (3) is also within the scope of the present invention. Step (3) may include the above-mentioned step (A) and step (B) or step (C) and step (D) and the like.

4. Method for Evaluating Toxicity or Efficacy

Since a retinal tissue or retinal cells (e.g., retinal progenitor cell, retinal layer-specific neural cell) produced by the production method of the present invention is useful as a material for disease study or drug discovery in a screening for a medicament for treating a disease due to a disorder of a retinal tissue or retinal cells, or in toxicity evaluation, it can be used as a reagent for evaluating toxicity or efficacy of a test substance. For example, iPS cells are produced from a human patient with a disease due to a disorder of a retinal tissue, particularly a hereditary disease, and using the iPS cells, a retinal tissue or retinal cells (e.g., retinal progenitor cell, retinal layer-specific neural cell) is produced by the method of the present invention. The retinal tissue or retinal cells may reproduce the disorder of the retinal tissue causing the disease of the patient in vitro. Therefore, the present invention provides a method for evaluating toxicity or efficacy of a test substance, which comprises contacting the test substance with a retinal tissue or retinal cells (e.g., retinal progenitor cell, retinal layer-specific neural cell) produced by the production method of the present invention, and detecting an influence of the substance on the cells or tissues.

For example, a retinal tissue or retinal cells (e.g., retinal progenitor cell, retinal layer-specific neural cell) having a particular disorder (e.g., hereditary disorder), which is produced by the production method of the present invention, are cultured in the presence or absence (negative control) of a test substance. Then, the severity of disorder of the retinal tissue or retinal cells treated with the test substance is compared with that of the negative control. As a result, a test substance that reduced the severity of the disorder can be selected as a candidate substance for a medicament for treating the disease resulting from the disorder. For example, a test substance that improves the physiological activity (e.g., survival promotion or maturation) of retinal cells produced by the production method of the present invention can be explored as a candidate substance of a pharmaceutical product. Alternatively, according to the production method of the present invention, retinal cells are prepared by inducing differentiation of the induced pluripotent stem cells which are prepared from a somatic cell having a gene mutation that causes a particular disorder such as a retinal disease and the like. A candidate of a test substance effective as a medicament or prophylactic drug for the disorder can be explored based on whether the retinal cells added with a test substance show the aforementioned disorder, as an index.

For toxicity evaluation, a retinal tissue or retinal cells (e.g., retinal progenitor cell, retinal layer-specific neural cell) produced by the production method of the present invention are cultured in the presence or absence (negative control) of a test substance. Then, the severity of toxicity on the retinal tissue or retinal cells treated with the test substance is compared with that of the negative control. As a result, a test substance that exerted toxicity as compared to the negative control can be judged as a substance having toxicity to the retinal tissue or retinal cells (e.g., retinal progenitor cell, retinal layer-specific neural cell).

That is, the present invention encompasses a method for evaluating toxicity comprising the following steps:
(step 1) a step of culturing a retinal tissue or retinal cells produced by the production method of the present invention under viable culture conditions for a given time in the presence of a test substance, and measuring the severity of cell injury,
(step 2) a step of culturing a retinal tissue or retinal cells produced by the production method of the present invention under viable culture conditions for a given time in the absence of a test substance or in the presence of a positive control, and measuring the severity of cell injury,
(step 3) a step of evaluating the toxicity of the test substance in step 1, based on the difference in the results measured in (step 1) and (step 2).

As used herein, "in the absence of a test substance" encompasses adding only a medium or a solvent used to dissolve the test substance instead of adding a test substance. In addition, "positive control" means a known compound having toxicity. Examples of the method for measuring the severity of cell injury include a method for measuring the number of viable cells, for example, a method for measuring intracellular ATP amount, a method for measuring the number of viable cells by cell staining (e.g., nucleus staining) and morphology observation and the like.

In step 3, as a method for evaluating the toxicity of a test substance, the measurement value in step 1 and the measurement value of the negative control in step 2 are compared, and when the severity of cell injury in step 1 is high, the test substance can be judged to have toxicity. In addition, the measurement value in step 1 and the measurement value of the positive control in step 2 are compared, and when the severity of cell injury in step 1 is the same or above, the test substance can be judged to have toxicity.

5. Pharmaceutical Composition

The present invention provides a pharmaceutical composition containing an effective amount of a retinal tissue or retinal cells (e.g., retinal progenitor cell, retinal layer-specific neural cell) produced by the production method of the present invention.

The pharmaceutical composition contains an effective amount of a retinal tissue or retinal cells (e.g., retinal progenitor cell, retinal layer-specific neural cell) produced by the production method of the present invention, and a pharmaceutically acceptable carrier.

As a pharmaceutically acceptable carrier, a physiological aqueous solvent (saline, buffer, serum-free medium etc.) can be used. Where necessary, in a transplantation therapy, a medicament containing a tissue or cells to be transplanted may contain conventionally used preservative, stabilizer, reducing agent, isotonizing agent and the like.

The pharmaceutical composition of the present invention can be produced as a suspension by suspending retinal tissues or retinal cells produced by the production method in an appropriate physiological aqueous solvent. Where necessary, the composition may be added with a cryopreservative, cryopreserved, thawed when in use, washed with buffer, and used for a transplantation therapy.

A retinal tissue obtained by the production method of the present invention may also be cut in an appropriate size with tweezers and the like to give a sheet preparation.

Cells obtained by the production method of the present invention may also be subjected to adhesion culture in step (3) for differentiation induction to form a sheet-like cells to give a sheet preparation.

The pharmaceutical composition of the present invention is useful as a medicament for a disease due to a disorder of a retinal tissue or retinal cells (e.g., retinal progenitor cell, retinal layer-specific neural cell).

6. Therapeutic Drug (Medicament)

A retinal tissue or retinal cells (e.g., retinal progenitor cell, retinal layer-specific neural cell) produced by the production method of the present invention is useful for a transplantation therapy for a disease due to a disorder of a retinal tissue or retinal cells. Thus, the present invention provides a medicament for treating a disease due to a disorder of a retinal tissue or retinal cells, which contains a retinal tissue or retinal cells (e.g., retinal progenitor cell, retinal layer-specific neural cell) produced by the production method of the present invention. A retinal tissue or retinal cells (e.g., retinal progenitor cell, retinal layer-specific neural cell) produced by the production method of the present invention can be used as a medicament for treating the disease due to a disorder of a retinal tissue or retinal cells or to complement the corresponding damaged site in a damaged state of a retinal tissue. A disease due to a disorder of a retinal tissue or retinal cells, and a damaged state of a retinal tissue can be treated by transplanting a retinal tissue or retinal cells produced by the production method of the present invention to a patient with a disease due to a disorder of a retinal tissue or retinal cells, or a damaged state of a retinal tissue, who requires transplantation, to complement the retinal cells or disordered retinal tissue itself. Examples of the disease due to a disorder of a retinal tissue or retinal cell include macular degeneration, age-related macular degeneration, retinal pigment denaturation, cataract, glaucoma, cornea disease, retinopathy and the like which are ophthalmologic diseases.

In transplantation therapy, rejection due to the difference in histocompatibility antigens often poses a problem. However, the problem can be solved by using pluripotent stem cells (e.g., induced pluripotent stem cells) established from the somatic cells of the transplantation recipient. That is, in a preferable embodiment, pluripotent stem cells (e.g., induced pluripotent stem cells) established from the somatic cells of the recipient are used as pluripotent stem cells in the method of the present invention, and a retinal tissue or retinal cells, which is immunologically self for the recipient, are produced and transplanted to the recipient.

In addition, an allogenic retinal tissue or retinal cell may be produced from a pluripotent stem cell (e.g., induced pluripotent stem cell) established from a somatic cell of others who are immunologically compatible with the recipient (e.g., compatible in HLA type and MHC type), and transplanted to the recipient.

EXAMPLES

The present invention is explained in detail in the following by referring to Examples and Pharmacological Examples, Examples, which are not to be construed as limitative.

Example 1: Production Example of Retinal Tissue from Human iPS Cell Using Wnt Signal Transduction Pathway Inhibiting Substance in Step 2 and Step 3 after Step 1 (Also Called Precondition)

Human iPS cells (1231A3 strain, obtained from Kyoto University) were cultured under feeder free according to the method described in "Scientific Reports, 4, 3594 (2014)". As a feeder-free medium, StemFit (registered trade mark) medium (AK03N, manufactured by Ajinomoto Co., Inc.) was used, and as a feeder-free scaffold, Laminin 511-E8 (manufactured by Nippi, Inc.) was used.

As a specific maintenance culture operation, subconfluent human iPS cells (1231A3 strain) were first washed with PBS, and dispersed into single cells by using TrypLE Select (manufactured by Life Technologies). Thereafter, the aforementioned human iPS cells dispersed into single cells were seeded in a plastic culture dish coated with Laminin 511-E8, and cultured under feeder-free conditions in StemFit (registered trade mark) medium in the presence of Y27632 (ROCK inhibiting substance, 10 μM). When a 6-well plate (manufactured by Iwaki, for cell culture, culture area 9.4 cm$^2$) was used as the aforementioned plastic culture dish, the number of plated cells for the aforementioned human iPS cells dispersed into single cells was adjusted to 1.0×10$^4$. One day after seeding, the entire amount of the medium was changed with StemFit (registered trade mark) medium free of Y27632. Thereafter, once in 1-2 days, the entire amount of the medium was changed with StemFit (registered trade mark) medium free of Y27632. Thereafter, the cells were cultured until 6 days after seeding when they became subconfluent (60% of culture area is covered with cells).

As a specific example of step 1 (Precondition) of the present production method, the following operation was performed. Subconfluent human iPS cells (1231A3 strain) were first washed with PBS, and dispersed into single cells by using TrypLE Select (manufactured by Life Technologies). Thereafter, the aforementioned human iPS cells dispersed into single cells were seeded in a plastic culture dish (manufactured by Iwaki) coated with Laminin 511-E8, and cultured under feeder-free conditions in StemFit (registered trade mark) medium in the presence of Y27632 (ROCK inhibiting substance, 10 μM). When a 6-well plate (manufactured by Iwaki, culture area 9.4 cm$^2$) was used as the aforementioned plastic culture dish, the number of plated cells for the aforementioned human iPS cells dispersed into single cells was adjusted to 1.0×10$^4$. When a 60 mm dish (manufactured by Iwaki, for cell culture, culture area 21 cm$^2$) was used as the aforementioned plastic culture dish, the number of plated cells for the aforementioned human iPS cells dispersed into single cells was adjusted to 2.0×10$^4$. One day after seeding, the entire amount of the medium was changed with StemFit (registered trade mark) medium free of Y27632. Thereafter, once in 1-2 days, the entire amount of the medium was changed with StemFit (registered trade mark) medium free of Y27632. Thereafter, the cells were cultured until 5 days after seeding, i.e., one day before subconfluence (50% of culture area is covered with cells). Even when cultured for 6 days after seeding, similar results were obtained.

The aforementioned feeder-free cultured human iPS cells one day before subconfluence were feeder-free cultured for one day in the presence of SB431542 (TGFβ signal transduction pathway inhibiting substance (TGFβR-i), 5 μM) and SAG (Sonic hedgehog signal transduction pathway activating substance (Shh), 300 nM) (step 1: Precondition treatment, FIG. 1 "Precondition: TGFβR-i+Shh") or in the absence thereof (step 1: without Precondition treatment, FIG. 1 "Untreated control") in a Stem Fit (registered trade mark) medium (AK03N; manufactured by Ajinomoto Co., Inc.). The cultured cells were subjected to bright field observation using an inverted microscope (manufactured by KEYENCE CORPORATION, BIOREVO). As a result, it was found that a treatment with a TGFβ signal transduction pathway inhibiting substance (SB431542) and a Sonic hedgehog signal transduction pathway activating substance during the feeder-free culture did not exert a large influence on the morphology of human iPS cells.

The thus-prepared human iPS cells free of a Precondition treatment and Precondition-treated human iPS cells were treated with a cell dispersion solution by using TrypLE Select (manufactured by Life Technologies), and further dispersed into single cells by a pipetting operation. Thereafter, the above human iPS cells dispersed into single cells were suspended in 100 μl of a serum-free medium in a non-cell-adhesive 96 well culture plate (PrimeSurface 96V-bottom plate, SUMITOMO BAKELITE) at 1.0×10$^4$ cells per well, and subjected to suspension culture at 37° C., 5% $CO_2$. As a serum-free medium (gfCDM+KSR) therefor, a 1:1 mixture of F-12 medium and IMDM medium supplemented with 10% KSR, 450 μM 1-monothioglycerol, 1× chemically defined lipid concentrate was used.

At the start of the suspension culture (on day 0 after the start of suspension culture, step 2 start), Y27632 (final concentration 20 μM) was added to the aforementioned serum-free medium, and the cells were further cultured in a medium containing or not containing a Wnt signal transduction pathway inhibiting substance (IWR-1e, 3 μM). A cell aggregate was formed under conditions with or without Precondition by day 2 after the start of suspension culture (step 2 completed, and step 3 started).

On day 3 after the start of suspension culture, a medium not containing Y27632, containing human recombinant BMP4 (manufactured by R&D) and further containing or not containing IWR-1e was added by 50 μl such that a final concentration of exogenous human recombinant BMP4 would be 1.5 nM (55 ng/ml) and the concentration of exogenous IWR-1e would not change. Thereafter, a half-medium exchange operation using the aforementioned serum-free medium not containing Y27632, SAG and human recombinant BMP4 and further containing or not containing IWR-1e was performed once every 2-4 days to avoid change of the concentration of exogenous IWR-1e.

The thus-prepared cells on day 17 after the start of suspension culture were subjected to bright field observation using an inverted microscope (manufactured by Nikon Corporation, ECLIPSE Ti) (FIG. 1). As a result, under conditions without Precondition and without addition of a Wnt signal transduction pathway inhibiting substance, aggregate growth was poor and the shape thereof collapsed (FIG. 1A). In contrast, a cell aggregate not deformed and having a dense interior was obtained under conditions with addition of a Wnt signal transduction pathway inhibiting substance, and it was found that a neural tissue was formed (FIG. 1B). Furthermore, under conditions with Precondition and without addition of a Wnt signal transduction pathway inhibiting substance (FIG. 1C) or with addition of a Wnt signal transduction pathway inhibiting substance (FIG. 1D), an undeformed round cell aggregate with a smooth surface and dense inside of aggregate was obtained, and it was found that a neural tissue was formed.

Figure 2:
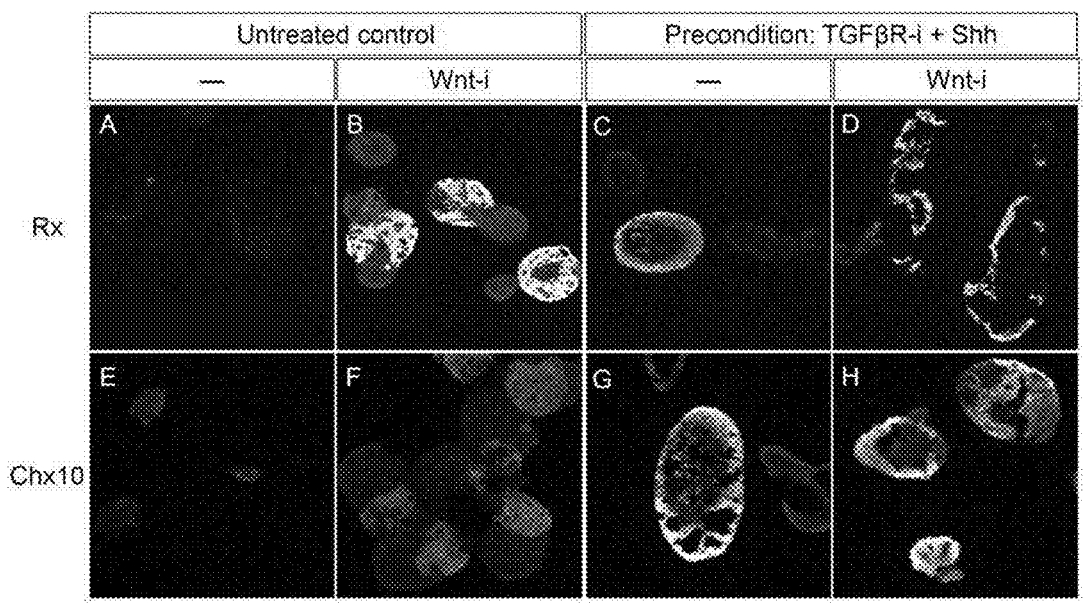
FIG. 2 shows the comparison results of expression of Rx (A-D) and Chx10 (E-H) in cell aggregates by immunohistostaining between the conditions of with (C, D, G, H) or without (A, B, E, F) Precondition.

The above cell aggregates on day 17 after the start of suspension culture were each fixed with 4% para-formaldehyde and cryosections were prepared. These cryosections were immunostained for Rx (anti-Rx antibody, Takara, Guinea Pig.), which is one of the retinal tissue markers, or Chx10 (anti-Chx10 antibody, manufactured by Exalpha, sheep), which is one of the retinal tissue markers. These immunostained sections were observed using an inverted fluorescence microscope (manufactured by KEYENCE CORPORATION, BIOREVO) (FIG. 2).

As a result, a cell aggregate produced under conditions without Precondition with SB431542 and SAG in step 1, and without addition of IWR-1e in step 2 and step 3, it was found that the proportion rate of Rx positive cells to the total cells was not more than about 3% (FIG. 2A).

In the cell aggregate produced under conditions not including Precondition with SB431542 and SAG in step 1 and including addition of IWR-1e in step 2 and step 3, the proportion of Rx positive cells in the total cells was about 40% (FIG. 2B). From the analysis of serial sections, weak Chx10 positiveness was observed in the cell aggregate produced under these conditions (FIG. 2F).

In the cell aggregate produced under conditions including Precondition with SB431542 and SAG in step 1 and no addition of IWR-1e in step 2 and step 3, it was found that the proportion of Rx positive cells in the total cells was about 40% (FIG. 2C). From the analysis of serial sections, cell aggregate produced under these conditions, about 40% of Chx10 positive (strong positive) cells was observed (FIG. 2G).

Furthermore, it was found that, in the cell aggregate produced under conditions including Precondition with SB431542 and SAG in step 1 and including addition of IWR-1e in step 2 and step 3, the proportion of Rx positive cells in the total cells was about 60% (FIG. 2D). From the analysis of serial sections, in a cell aggregate produced under these conditions, about 60% of Chx10 positive (strong positive) cells were observed (FIG. 2H).

From these results, it was found that a neural tissue was hardly formed under conditions not including Precondition and not including addition of a Wnt inhibitor in step 2 and step 3, whereas a neural tissue can be formed under any other conditions.

As compared to the conditions without Precondition and without addition of Wnt inhibitor in step 2 and step 3, it was found that retinal tissue formation is somewhat promoted under conditions without Precondition and with addition of a Wnt signal transduction pathway inhibiting substance in step 2 and step 3 (FIG. 1A, B, FIG. 2A, B, E, F). On the other hand, it was found that a retinal tissue can be highly efficiently formed with Precondition with a TGFβ family signal transduction pathway inhibiting substance and a Shh signal transduction pathway activating substance in step 1 and further addition of a Wnt signal transduction pathway inhibiting substance in step 2 and step 3 (FIG. 2B, D, F, H).

Example 2: Production Example of Retinal Tissue from Human iPS Cell Including Precondition with Sonic Hedgehog Signal Transduction Pathway Activating Substance in Step 1 and Addition of Wnt Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N; manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day in the presence of SAG (Sonic hedgehog signal transduction pathway activating substance (Shh), 300 nM) (step 1: Precondition treatment, FIG. 3 "Precondition: Shh") or in the absence thereof (step 1: Precondition-free conditions, FIG. 3 "Untreated control") in a Stem Fit (registered trade mark) medium (AK03N; manufactured by Ajinomoto Co., Inc.).

The thus-prepared Precondition-treated human iPS cells, and human iPS cells under Precondition-free conditions were each treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in the serum-free medium under the following five Conditions 1-5.

Condition 1

Conditions not including Precondition treatment in step 1 and not including addition of an exogenous Wnt signal transduction pathway inhibiting substance or an exogenous Sonic hedgehog signal transduction pathway activating substance to the aforementioned serum-free medium at the start of step 2 (FIG. 3A).

Condition 2

Condition including Precondition treatment in step 1 and not including addition of an exogenous Wnt signal transduction pathway inhibiting substance or an exogenous Sonic hedgehog signal transduction pathway activating substance to the aforementioned serum-free medium at the start of step 2 (FIG. 3B).

Condition 3

Condition including Precondition treatment in step 1, addition of IWR-1e (3 µM) as an Wnt signal transduction pathway inhibiting substance and no addition of an exogenous Sonic hedgehog signal transduction pathway activating substance to the aforementioned serum-free medium at the start of step 2 (FIG. 3C).

Condition 4

Condition including Precondition treatment in step 1, no addition of an exogenous Wnt signal transduction pathway inhibiting substance and addition of SAG (30 nM) as a Sonic hedgehog signal transduction pathway activating substance to the aforementioned serum-free medium at the start of step 2 (FIG. 3D).

Conditions 5

Condition including Precondition treatment in step 1, addition of IWR-1e (3 µM) as a Wnt signal transduction pathway inhibiting substance and addition of SAG (30 nM) as a Sonic hedgehog signal transduction pathway activating substance to the aforementioned serum-free medium at the start of step 2 (FIG. 3E).

By day 2 after the start of suspension culture, cell aggregates were formed under any of Condition 1-5 (step 2 completed, and step 3 started).

On day 3 after the start of suspension culture, a medium not containing Y27632 or SAG, containing human recombinant BMP4 (manufactured by R&D) and further containing or not containing IWR-1e was added by 50 μl such that a final concentration of exogenous human recombinant BMP4 would be 1.5 nM (55 ng/ml) and the concentration of exogenous IWR-1e would not change. Thereafter, a half-medium exchange operation using the aforementioned serum-free medium not containing Y27632, SAG and human recombinant BMP4 and further containing or not containing IWR-1e was performed once every 2-4 days to avoid change of the concentration of exogenous IWR-1e.

Figure 3:
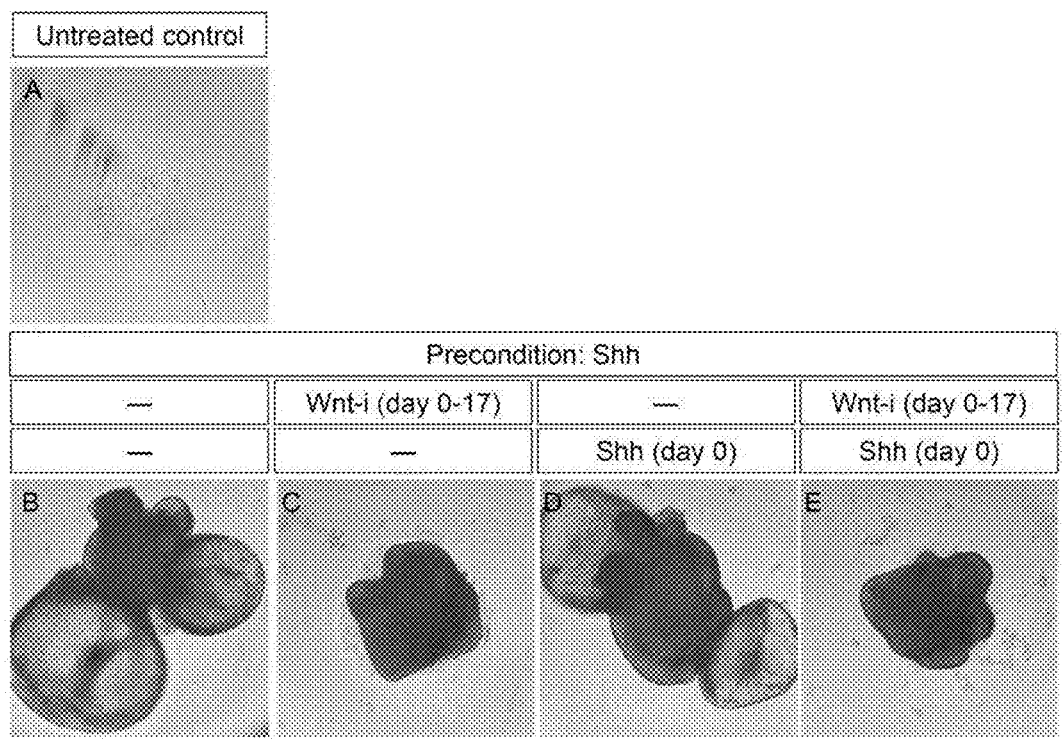
FIG. 3 shows the comparison results of morphology of cell aggregates formed from human iPS cells under various culture conditions by bright field observation.

The thus-prepared cells on day 17 after the start of suspension culture were subjected to bright field observation using an inverted microscope (manufactured by Nikon Corporation, ECLIPSE Ti) (FIG. 3). As a result, it was found that an aggregate was not grown and a neural tissue was not formed under Condition 1 without Precondition in step 1 (FIG. 3A), whereas aggregate was grown and a neural tissue could be formed under Conditions 2-5 with a Precondition treatment with a Sonic hedgehog signal transduction pathway activating substance in step 1 (FIG. 3B-E). Particularly, it was found that the formation efficiency of a neural tissue is good under Conditions 3 and 5 wherein a Wnt signal transduction pathway inhibiting substance was allowed to act in step 2 and step 3 (FIG. 3C, E), as compared to Conditions 2 and 4 wherein a Wnt signal transduction pathway inhibiting substance was not allowed to act (FIG. 3B, D).

Figure 4:
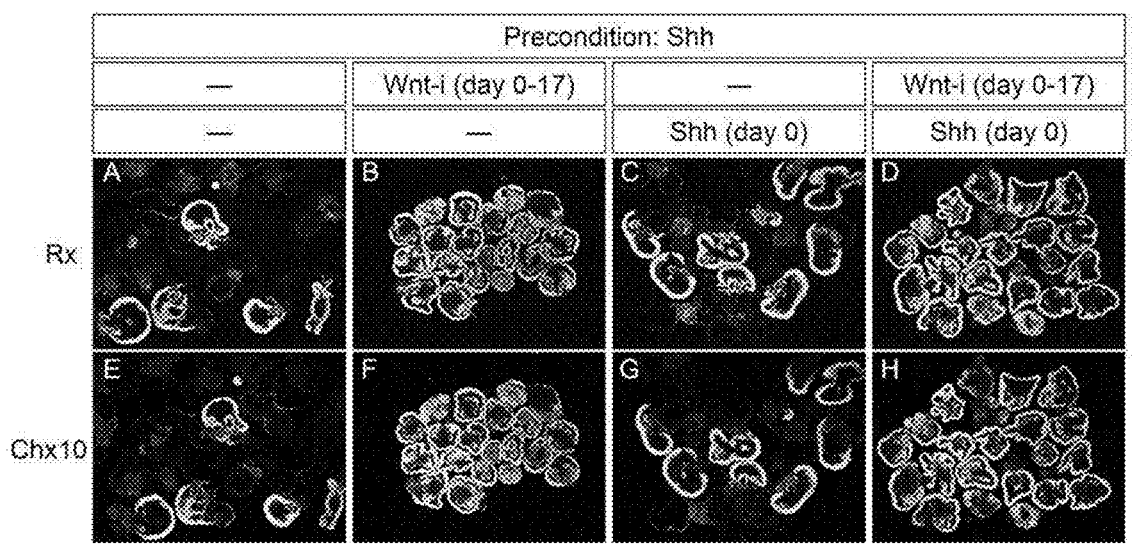
FIG. 4 shows the comparison results of expression of Rx (A-D) and Chx10 (E-H) in cell aggregates formed from human iPS cells under various culture conditions by immunohistostaining.

The above cell aggregates on day 17 after the start of suspension culture were each fixed with 4% para-formaldehyde to give cryosections. These cryosections were immunostained for Rx (anti-Rx antibody, Takara, Guinea Pig.), which is one of the retinal tissue markers, or Chx10 (anti-Chx10 antibody, manufactured by Exalpha, sheep), which is one of the retinal tissue markers. These immunostained sections were observed using an inverted fluorescence microscope (manufactured by KEYENCE CORPORATION, BIOREVO) (FIG. 4).

As a result, it was found that a neural tissue was not formed under Condition 1 without Precondition, whereas a neural tissue was formed under any of Conditions 2-5 with a Precondition treatment with SAG.

Of these, under Condition 2 with Precondition with SAG in step 1 and without addition of an exogenous Wnt signal transduction pathway inhibiting substance in step 2 and step 3, the proportion of Rx positive cells in the total cells was about 40% (FIG. 4A). From the analysis of serial sections, it was found that, in the retinal tissue of the cell aggregate produced under the aforementioned conditions, Rx positive cell was a Chx10 co-positive (FIG. 4E).

On the other hand, it was found that the proportion of Rx positive cells in the total cells is about 90% in a cell aggregate produced under Condition 3 with Precondition with SAG in step 1, and addition of IWR-1e in step 2 and step 3 (FIG. 4B). From the analysis of serial sections, it was found that, in the retinal tissue of the cell aggregate produced under the aforementioned conditions, the Rx positive cell is a Chx10 co-positive (FIG. 4F).

That is, from the comparison of Condition 2 and Condition 3, it was found that a retinal tissue can be formed with about 90% efficiency by Precondition in step 1 and a further treatment with an Wnt signal transduction pathway inhibiting substance in step 2 and step 3.

In the cell aggregate produced under Condition 4 including Precondition with SAG in step 1 and including Condition 4 with addition of SAG in step 2, the proportion of Rx positive cells in the total cells was about 60% (FIG. 4C). From the analysis of serial sections, it was found that, in the retinal tissue of the cell aggregate produced under the above-mentioned conditions, Rx positive cell is a Chx10 co-positive (FIG. 4G).

On the other hand, it was found that, in the cell aggregate produced under conditions including Precondition with SAG in step 1 and Condition 5 with addition of SAG in step 2 and addition of IWR-1e in step 2 and step 3, the proportion of Rx positive cells in the total cells was about 90% (FIG. 4D). From the analysis of serial sections, it was found that, in the retinal tissue of the cell aggregate produced under the aforementioned conditions, Rx positive cell is a Chx10 co-positive (FIG. 4H).

That is, from the comparison of Condition 4 and Condition 5, it was found that a retinal tissue can be formed with about 90% efficiency by Precondition in step 1, addition of a Sonic hedgehog signal transduction pathway activating substance in step 2, and a further treatment with a Wnt signal transduction pathway inhibiting substance in step 2 and step 3.

Example 3: Production Example of Retinal Tissue from Human iPS Cell Including Precondition with TGFβ Signal Transduction Pathway Inhibiting Substance in Step 1 and Addition of Wnt Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

Figure 5:
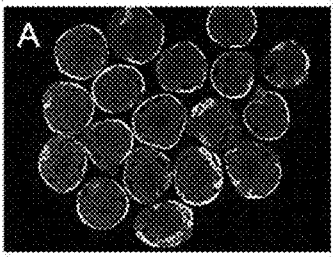
FIG. 5 shows the comparison results of expression of Chx10 in cell aggregates formed from human iPS cells under various culture conditions by immunohistostaining.

The feeder-free cultured human iPS cells one day before subconfluence were feeder-free cultured for one day under conditions of addition of SB431542 (TGFβ signal transduction pathway inhibiting substance (TGFβR-i), 5 μM) and no addition of an exogenous Sonic hedgehog signal transduction pathway activating substance (step 1: Precondition (TGFβR-i) treatment, FIG. 5 "Precondition: TGFβR-i"), or in the presence of SB431542 (TGFβ signal transduction pathway inhibiting substance (TGFβR-i), 5 μM) and SAG (Sonic hedgehog signal transduction pathway activating substance (Shh), 300 nM) (step 1: Precondition (TGFβR-i+Shh) treatment, FIG. 5 "Precondition: TGFβR-i+Shh"), in a Stem Fit (registered trade mark) medium (AK03N; manufactured by Ajinomoto Co., Inc.).

The thus-prepared Precondition (TGFβR-i)-treated human iPS cells, and Precondition (TGFβR-i+Shh)-treated human iPS cells were each treated with the cell dispersion solution by using TrypLE Select (Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in the serum-free medium under the following three Conditions 1-3.

Condition 1

Condition including Precondition (TGFβR-i) treatment in step 1 and addition of IWR-1e (3 µM) as a Wnt signal transduction pathway inhibiting substance and SAG (30 nM) as a Sonic hedgehog signal transduction pathway activating substance to the aforementioned serum-free medium at the start of step 2 (FIG. 5A).

Condition 2

Condition including Precondition (TGFβR-i+Shh) treatment in step 1, and addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 5B).

Condition 3

Condition including Precondition (TGFβR-i+Shh) treatment in step 1, and addition of IWR-1e (3 µM) as a Wnt signal transduction pathway inhibiting substance and SAG (30 nM) as a Sonic hedgehog signal transduction pathway activating substance to the aforementioned serum-free medium at the start of step 2 (FIG. 5C).

By day 2 after the start of suspension culture, cell aggregates were formed under any of the aforementioned Condition 1-5 (step 2 completed, and step 3 started).

On day 3 after the start of suspension culture, the aforementioned serum-free medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration of exogenous IWR-1e would not change. Thereafter, a half-medium exchange operation using the aforementioned serum-free medium not containing Y27632, SAG and human recombinant BMP4 and further containing IWR-1e was performed once every 2-4 days to avoid change of the concentration of exogenous IWR-1e.

The thus-prepared cells on day 17 after the start of suspension culture were subjected to bright field observation using an inverted microscope (manufactured by Nikon Corporation, ECLIPSE Ti). As a result, it was found that a neural tissue could be formed under any of Condition 1-3.

Cell aggregates on day 17 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These immunostained sections were observed with an inverted fluorescence microscope (manufactured by KEYENCE CORPORATION, BIOREVO). As a result, it was found that a neural tissue was formed and the proportion of Chx10 positive in the neural tissues is about 90% under any of Conditions 1-3 (FIG. 5A-C). From the analysis of serial sections, in the retinal tissues, these Chx10 positive cells could be confirmed to be Rx co-positive.

That is, it was found that a retinal tissue can be formed efficiently from human iPS cells under conditions including Precondition with a TGFβ signal transduction pathway inhibiting substance in step 1 and addition of a Wnt signal transduction pathway inhibiting substance in step 2 and step 3.

Example 4: Production Example of Retinal Tissue from Human iPS Cell Including Precondition with BMP Signal Transduction Pathway Inhibiting Substance in Step 1 and Addition of Wnt Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

Figure 6:
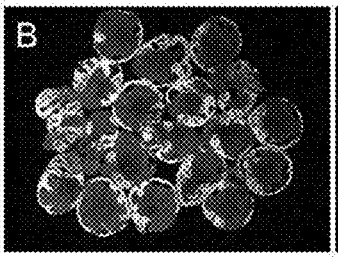
FIG. 6 shows the comparison results of expression of Chx10 in cell aggregates formed from human iPS cells under various culture conditions by immunohistostaining.

The feeder-free cultured human iPS cells one day before subconfluence were feeder-free cultured for one day under conditions of addition of LDN193189 (BMP signal transduction pathway inhibiting substance (BMPR-i), 100 nM) and no addition of an exogenous Sonic hedgehog signal transduction pathway activating substance (step 1: Precondition (BMPR-i) treatment, FIG. 6 "Precondition: BMPR-i"), or in the presence of LDN193189 (BMP signal transduction pathway inhibiting substance, 100 nM, BMPR-i) and SAG (Sonic hedgehog signal transduction pathway activating substance (Shh), 300 nM) (step 1: Precondition (BMPR-i+Shh) treatment, FIG. 6 "Precondition: BMPR-i+Shh"), in a Stem Fit (registered trade mark) medium (AK03N; manufactured by Ajinomoto Co., Inc.).

The thus-prepared Precondition (BMPR-i)-treated human iPS cells, and Precondition (BMPR-i+Shh)-treated human iPS cells were each treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in the serum-free medium under the following three Conditions 1-3.

Condition 1

Condition including Precondition (BMPR-i) treatment in step 1 and addition of IWR-1e (3 µM) as a Wnt signal transduction pathway inhibiting substance and SAG (30 nM) as a Sonic hedgehog signal transduction pathway activating substance to the aforementioned serum-free medium at the start of step 2 (FIG. 6A).

Condition 2

Condition including Precondition (BMPR-i+Shh) treatment in step 1, and addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 6B).

Condition 3

Condition including Precondition (BMPR-i+Shh) treatment in step 1, and addition of IWR-1e (3 µM) as a Wnt signal transduction pathway inhibiting substance and SAG (30 nM) as a Sonic hedgehog signal transduction pathway activating substance to the aforementioned serum-free medium at the start of step 2 (FIG. 6C).

By day 2 after the start of suspension culture, cell aggregates were formed under any of the aforementioned Condition 1-3 (step 2 completed, and step 3 started).

On day 3 after the start of suspension culture, the aforementioned serum-free medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration of exogenous IWR-1e would not change. Thereafter, a half-medium exchange operation using the aforementioned serum-free medium not containing Y27632, SAG and human recombinant BMP4 and further containing IWR-1e was performed once every 2-4 days to avoid change of the concentration of exogenous IWR-1e.

The thus-prepared cells on day 17 after the start of suspension culture were subjected to bright field observation using an inverted microscope (manufactured by Nikon Corporation, ECLIPSE Ti). As a result, it was found that a neural tissue could be formed under any of Condition 1-3.

Cell aggregates on day 17 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These immunostained sections were observed with an inverted fluorescence microscope (manufactured by KEYENCE CORPORATION, BIOREVO). As a result, it was found that a neural tissue was formed and the proportion of Chx10 positive in the neural tissues is about 90% under any of Conditions 1-3 (FIG. 6A-C). From the analysis of serial sections, in the retinal tissues, these Chx10 positive cells could be confirmed to be Rx co-positive.

That is, it was found that a retinal tissue can be formed efficiently from human iPS cells under conditions including Precondition with a BMP signal transduction pathway inhibiting substance in step 1 and addition of a Wnt signal transduction pathway inhibiting substance in step 2 and step 3.

Example 5: Production Example of Retinal Tissue from Human iPS Cell Including Precondition with TGFβ Signal Transduction Pathway Inhibiting Substance and/or a Sonic Hedgehog Signal Transduction Pathway Activating Substance in Step 1, Addition of Wnt Signal Transduction Pathway Inhibiting Substance in Step 2 and Step 3, Addition of BMP Signal Transduction Pathway Activating Substance in Step 3 and Use of Sonic Hedgehog Signal Transduction Pathway Activating Substance and Serum Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a m feeder-free medium and Laminin 511-E8 (manufactured by Nippi, Inc.) as a feeder-free scaffold.

Figure 7:
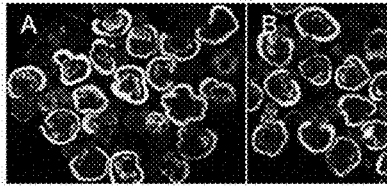
FIG. 7 shows the comparison results of expression of Chx10 in cell aggregates formed from human iPS cells under various culture conditions by immunohistostaining.

The feeder-free cultured human iPS cells one day before subconfluence were feeder-free cultured for one day under conditions including no addition of an exogenous TGFβ signal transduction pathway inhibiting substance and addition of SAG (Sonic hedgehog signal transduction pathway activating substance (Shh), 300 nM) (step 1: Precondition (Shh) treatment, FIG. 7 "Precondition: Shh"), and conditions including addition of SB431542 (TGFβ signal transduction pathway inhibiting substance (TGFβR-i), 5 μM) and SAG (Sonic hedgehog signal transduction pathway activating substance (Shh), 300 nM) (step 1: Precondition (TGFβR-i+Shh) treatment, FIG. 7 "Precondition: TGFβR-i+Shh") in a Stem Fit (registered trade mark) medium (AK03N; manufactured by Ajinomoto Co., Inc.).

The thus-prepared Precondition (Shh)-treated human iPS cells or Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium and the cells were cultured in the serum-free medium under the following four Conditions 1-4.

Condition 1

Condition including Precondition (Shh) treatment in step 1, and addition of IWR-1e (3 μM) as a Wnt signal transduction pathway inhibiting substance and no addition of an exogenous Sonic hedgehog signal transduction pathway activating substance to the aforementioned serum-free medium at the start of step 2 (FIG. 7A).

Condition 2

Condition including Precondition (Shh) treatment in step 1, and addition of IWR-1e (3 μM) as a Wnt signal transduction pathway inhibiting substance and addition of SAG (30 nM) as a Sonic hedgehog signal transduction pathway activating substance to the aforementioned serum-free medium at the start of step 2 (FIG. 7B).

Condition 3

Condition including Precondition (TGFβR-i+Shh) treatment in step 1, and addition of IWR-1e (3 μM) as a Wnt signal transduction pathway inhibiting substance and no addition of an exogenous Sonic hedgehog signal transduction pathway activating substance to the aforementioned serum-free medium at the start of step 2 (FIG. 7C).

Condition 4

Condition including Precondition (TGFβR-i+Shh) treatment in step 1, and addition of IWR-1e (3 μM) as a Wnt signal transduction pathway inhibiting substance and SAG (30 nM) as a Sonic hedgehog signal transduction pathway activating substance to the aforementioned serum-free medium at the start of step 2 (FIG. 7D).

By day 2 after the start of suspension culture, cell aggregates were formed under any of the aforementioned Condition 1-4 (step 2 completed, and step 3 started).

On day 3 after the start of suspension culture, the aforementioned serum-free medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration of exogenous IWR-1e would not change.

Thereafter, a half-medium exchange operation using the aforementioned serum-free medium not containing Y27632, SAG and human recombinant BMP4 and further containing IWR-1e was performed once every 2-4 days to avoid change of the concentration of exogenous IWR-1e.

Next, on day 10 after the start of suspension culture, using Shh serum-containing medium obtained by adding SAG (100 nM) as a Sonic hedgehog signal transduction pathway activating substance and fetal calf serum (10%) as a serum to the aforementioned serum-free medium (FIG. 7 "Shh+ serum"), an operation to exchange about 80% of the medium (80% exchange operation) was repeated 3 times, thereby changing the medium to the aforementioned Shh serum-containing medium not containing Y27632, human recombinant BMP4 or IWR1-e, and containing SAG and the serum. Thereafter, once every 2-4 days, a half-medium exchange operation with the aforementioned Shh serum-containing medium was performed.

The thus-prepared cells on day 17 after the start of suspension culture were subjected to bright field observation using an inverted microscope (manufactured by Nikon Corporation, ECLIPSE Ti). As a result, it was found that a neural tissue could be formed under any of Conditions 1-4.

Cell aggregates on day 17 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These immunostained sections were observed with an inverted fluorescence microscope (manufactured by KEYENCE CORPORATION, BIOREVO). As a result, it was found that a neural tissue was formed and the proportion of Chx10 positive in the neural tissues is about 80% under any of Conditions 1-4 (FIG. 7A-D). From the analysis of serial sections, in the retinal tissues, these Chx10 positive cells could be confirmed to be Rx co-positive.

That is, it was found that a retinal tissue can be formed efficiently from human iPS cells under conditions including Precondition in step 1, addition of a Wnt signal transduction pathway inhibiting substance in step 2 and a BMP signal transduction pathway inhibiting substance in step 3, followed by culturing in Shh serum-containing medium.

Example 6: Production Example of Retinal Tissue from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance and TGFβ Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) (step 1: Precondition (TGFβR-i+Shh) treatment, FIG. 8 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (Prime-Surface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in the serum-free medium under the following four Conditions 1-4.

Condition 1

Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 8A).

Condition 2

Condition including addition of IWR-1e (3 µM) as a Wnt signal transduction pathway inhibiting substance and addition of SAG (30 nM) as a Sonic hedgehog signal transduction pathway activating substance to the aforementioned serum-free medium at the start of step 2 (FIG. 8B).

Condition 3

Condition including addition of IWR-1e (3 µM) as a Wnt signal transduction pathway inhibiting substance and SB431542 (5 µM) as a TGFβ signal transduction pathway inhibiting substance and no addition of an exogenous Sonic hedgehog signal transduction pathway activating substance to the aforementioned serum-free medium at the start of step 2 (FIG. 8C).

Condition 4

Condition including addition of IWR-1e (3 µM) as a Wnt signal transduction pathway inhibiting substance and SB431542 (5 µM) as a TGFβ signal transduction pathway inhibiting substance and SAG (30 nM) as a Sonic hedgehog signal transduction pathway activating substance to the aforementioned serum-free medium at the start of step 2 (FIG. 8D).

By day 2 after the start of suspension culture, cell aggregates were formed under any of Conditions 1-4 (step 2 completed, and step 3 started).

On day 3 after the start of suspension culture, a medium not containing Y27632 or SAG, containing human recombinant BMP4 (manufactured by R&D) and further containing or not containing IWR-1e and SB431542 was added by 50 µl such that a final concentration of exogenous human recombinant BMP4 would be 1.5 nM (55 ng/ml) and the concentration of exogenous IWR-1e and SB431542 would not change. Thereafter, a half-medium exchange operation was performed once every 2-4 days with the aforementioned serum-free medium not containing Y27632, SAG, human recombinant BMP4 and further containing or not containing IWR-1e and SB431542 to avoid change of the concentration of exogenous IWR-1e and SB431542.

On day 10 after the start of suspension culture, a 80% medium exchange operation was performed 3 times using the aforementioned serum-free medium so that the concentration of exogenous IWR-1e and/or SB431542 would be 3% or less as compared to that before the medium exchange. Thereafter, once every 2-4 days, a half-medium exchange operation was performed using the aforementioned serum-free medium free of Y27632, SAG, human recombinant BMP4, IWR-1e and SB431542.

The thus-prepared cells on day 19 after the start of suspension culture were subjected to bright field observation using an inverted microscope (manufactured by Nikon Corporation, ECLIPSE Ti). As a result, it was found that a neural tissue could be formed under any of Conditions 1-4.

Figure 8:
FIG. 8 shows the comparison results of expression of Chx10 in cell aggregates formed from human iPS cells under various culture conditions by immunohistostaining. Counterstained with DAPI.

Cell aggregates on day 19 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. As counterstaining, nucleic acid was stained with DAPI. These stained sections were observed with an inverted fluorescence microscope (manufactured by KEYENCE CORPORATION, BIOREVO) (FIG. 8).

As a result, it was found that a neural tissue was formed under any of Conditions 1-4. In Condition 1, the proportion of the Chx10 positive retinal tissue was about 70%, in Condition 2, the proportion of the Chx10 positive retinal tissue was about 70%, in Condition 3, the proportion of the Chx10 positive retinal tissue was about 70%, and in Condition 4, the proportion of the Chx10 positive retinal tissue was about 80%. From the analysis of serial sections, these Chx10 positive cells could be confirmed to be Rx co-positive cells.

That is, it was found that efficient differentiation into a retinal tissue is also achieved under conditions including addition of, as in Condition 1 and Condition 2, a Wnt signal transduction pathway inhibiting substance in step 2 and step 3 and reduction of the concentration of the exogenous Wnt signal transduction pathway inhibiting substance to 3% or less in the course of step 3. Furthermore, it was found that efficient differentiation into a retinal tissue is also achieved under conditions including addition of, as in Conditions 3 and 4, a Wnt signal transduction pathway inhibiting substance and a TGFβ signal transduction pathway inhibiting substance in step 2 and step 3.

Example 7: Production Example of Retinal Tissue from Human iPS Cell Including Precondition with BMP Signal Transduction Pathway Inhibiting Substance and Sonic Hedgehog Signal Transduction Pathway Activating Substance in Step 1 and Use of Wnt Signal Transduction Pathway Inhibiting Substance and TGFβ Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of LDN193189 (BMP signal transduction pathway inhibiting substance (BMPR-i), 100 nM) and SAG (Sonic hedgehog signal transduction pathway activating substance (Shh), 300 nM) (step 1: Precondition (BMPR-i+Shh) treatment, FIG. 9 "Precondition: BMPR-i+Shh") in a Stem Fit (registered trade mark) medium (AK03N; manufactured by Ajinomoto Co., Inc.).

The thus-prepared Precondition (BMPR-i+Shh)-treated human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (Prime-Surface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium and the cells were cultured in the serum-free medium under the following two Conditions 1-2.

Condition 1

Condition including addition of IWR-1e (3 μM) as a Wnt signal transduction pathway inhibiting substance and no addition of an exogenous Sonic hedgehog signal transduction pathway activating substance to the aforementioned serum-free medium at the start of step 2 (FIG. 9A).

Condition 2

Condition including addition of IWR-1e (3 μM) as a Wnt signal transduction pathway inhibiting substance and SB431542 (5 μM) as a TGFβ signal transduction pathway inhibiting substance and no addition of an exogenous Sonic hedgehog signal transduction pathway activating substance to the aforementioned serum-free medium at the start of step 2 (FIG. 9B).

By day 2 after the start of suspension culture, cell aggregates were formed under Condition 1 and Condition 2 (step 2 completed, and step 3 started).

On day 3 after the start of suspension culture, a medium not containing Y27632 or SAG, containing human recombinant BMP4 (manufactured by R&D) and further containing or not containing IWR-1e and SB431542 was added by 50 μl such that a final concentration of exogenous human recombinant BMP4 would be 1.5 nM (55 ng/ml) and the concentration of exogenous IWR-1e would not change. Thereafter, a half-medium exchange operation was performed once every 2-4 days with the aforementioned serum-free medium not containing Y27632, SAG, human recombinant BMP4 and further containing or not containing IWR-1e and SB431542 to avoid change of the concentration of exogenous IWR-1e and SB431542.

On day 10 after the start of suspension culture, a 80% medium exchange operation was performed 3 times using the aforementioned serum-free medium so that the concentration of exogenous IWR-1e and/or SB431542 would be 3% or less as compared to that before the medium exchange. Thereafter, once every 2-4 days, a half-medium exchange operation was performed using the aforementioned serum-free medium free of Y27632, SAG, human recombinant BMP4, IWR-1e and S3431542.

The thus-prepared cells on day 19 after the start of suspension culture were subjected to bright field observation using an inverted microscope (manufactured by Nikon Corporation, ECLIPSE Ti). As a result, it was found that a neural tissue could be formed under Condition 1 and Condition 2.

Figure 9:
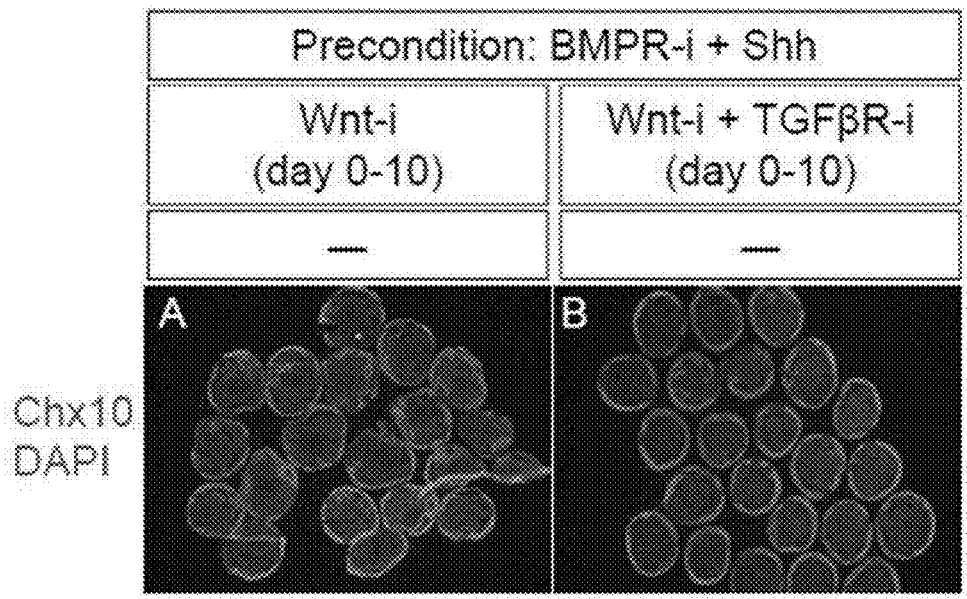
FIG. 9 shows the comparison results of expression of Chx10 in cell aggregates formed from human iPS cells under various culture conditions by immunohistostaining. Counterstained with DAPI.

Cell aggregates on day 19 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. As counterstaining, nucleic acid was stained with DAPI. These stained sections were observed with an inverted fluorescence microscope (manufactured by KEYENCE CORPORATION, BIOREVO) (FIG. 9).

As a result, it was found that a neural tissue could be formed in Condition 1 and Condition 2. In Condition 1, the proportion of the Chx10 positive retinal tissue was about 80%, and in Condition 2, the proportion of the Chx10 positive retinal tissue was about 90%. From the analysis of serial sections, it could be confirmed that these Chx10 positive cells are Rx co-positive cells.

That is, in Condition 1, it was found that efficient differentiation into a retinal tissue is also achieved under conditions including Precondition with a BMP signal transduction pathway inhibiting substance and a Sonic hedgehog signal transduction pathway activating substance in step 1, addition of a Wnt signal transduction pathway inhibiting substance in step 2 and step 3, and reduction of the concentration of the exogenous Wnt signal transduction pathway inhibiting substance to 3% or less in the course of step 3. Furthermore, in Condition 2, it was found that efficient differentiation into retinal cell is also achieved under conditions including Precondition with a BMPR inhibitor and a Sonic hedgehog signal transduction pathway activating substance in step 1, and addition of a Wnt signal transduction pathway inhibiting substance and a TGFβ signal transduction pathway inhibiting substance in step 2 and step 3.

In addition, it was found from Example 6 and Example 7 that efficient differentiation into retinal cell is also achieved by the addition of a Wnt signal transduction pathway inhibiting substance step 2 and step 3 when step 1 includes Precondition with a TGFβ signal transduction pathway inhibiting substance and a Sonic hedgehog signal transduction pathway activating substance or Precondition with a BMPR inhibitor and a Sonic hedgehog signal transduction pathway activating substance.

Example 8: Production Example of Retinal Tissue Using Human iPS Cell Established Using Sendaivirus Vector as Starting Material and Including Precondition in Step 1 and Use of Wnt Signal Transduction Pathway Inhibiting Substance in Step 2

Human iPS cells (TFH-R1-10-2 strain and TFH-R2-10-F8 strain, established by Sumitomo Dainippon Pharma Co., Ltd.) were established as follows. They were established according to the method described in the published protocol of Life Technologies (iPS 2.0 Sendai Reprogramming Kit, Publication Number MAN0009378, Revision 1.0) and the published protocol of Kyoto University (establish •maintenance culture of human iPS cells, CiRA_Ff-iPSC_protocol_JP_v140310, 4, www.cira.kyoto-u.ac.jp/j/research/protocol.html), and using peripheral blood mononuclear cells (PBMC) prepared by a well-known method as the starting material, commercially available Sendaivirus vector (4 factors of Oct3/4, Sox2, KLF4, L-Myc, CytoTune kit manufactured by DNAVEC Corporation (currently ID Pharma Co., Ltd.)), and StemFit (registered trade mark) medium (AK03N; manufactured by Ajinomoto Co., Inc.), Laminin511-E8 (manufactured by Nippi, Inc.).

Human iPS cells (TFH-R1-10-2 strain and TFH-R2-10-F8 strain) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) (step 1: Precondition (TGFβR-i+Shh) treatment, FIG. 8 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (Prime-Surface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium, IWR-1e (3 µM) was added as a Wnt signal transduction pathway inhibiting substance (FIG. 10 "Wnt-i (day 0-17)"), and SAG (30 nM) was added as a Sonic hedgehog signal transduction pathway activating substance (FIG. 10 "Shh day 0") and the cells were cultured. A cell aggregate was formed by day 2 after the start of suspension culture by using human iPS cells of any of TFH-R1-10-2 strain and TFH-R2-10-F8 strain as the starting material (step 2 completed, and step 3 started).

On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration of exogenous IWR-1e would not change. Thereafter, a half-medium exchange operation was performed once every 2-4 days with the aforementioned serum-free medium not containing Y27632, SAG, human recombinant BMP4 and further containing IWR-1e to avoid change of the concentration of IWR-1e.

The thus-prepared cells on day 17 after the start of suspension culture were subjected to bright field observation using an inverted microscope (manufactured by Nikon Corporation, ECLIPSE Ti). As a result, it was found that a neural tissue could be formed by using human iPS cells of any of TFH-R1-10-2 strain and TFH-R2-10-F8 strain as the starting material.

Figure 10:
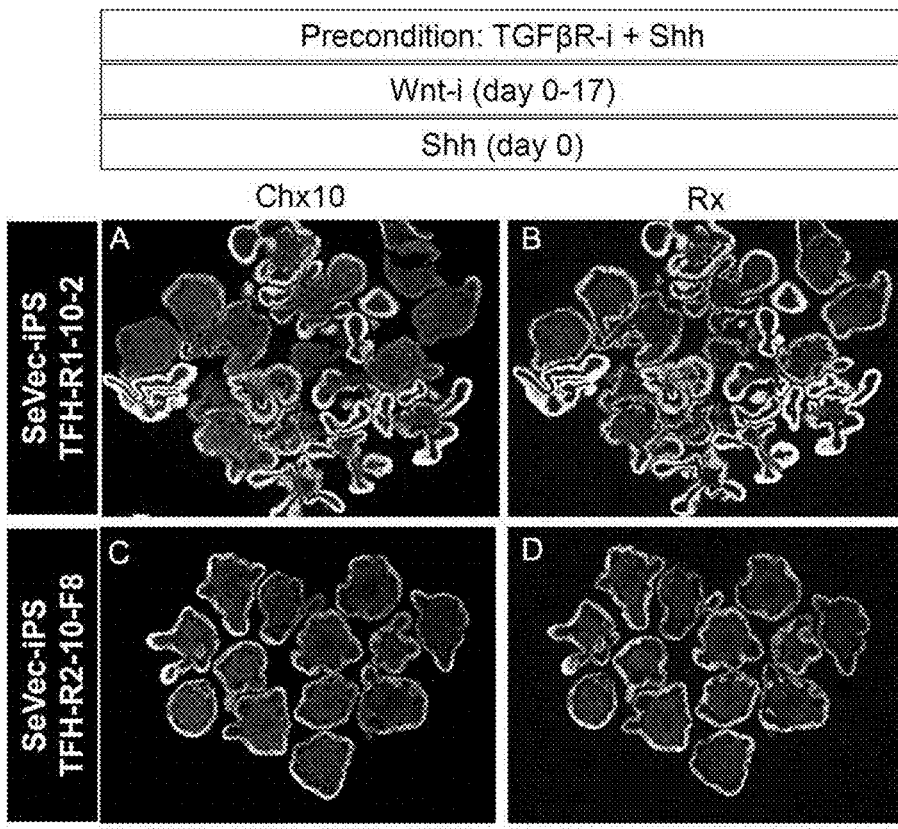
FIG. 10 shows the comparison results of expression of Chx10 (A, C) and Rx (B, D) in cell aggregates formed from human iPS cells (A, B: TFH-R1-10-2 strain, C, D: TFH-R2-10-F8 strain) under various culture conditions by immunohistostaining.

Cell aggregates on day 17 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These stained sections were observed with an inverted fluorescence microscope (manufactured by KEYENCE CORPORATION, BIOREVO) (FIG. 10).

As a result, it was found that a neural tissue could be formed by using human iPS cells of any of TFH-R1-10-2 strain and TFH-R2-10-F8 strain as the starting material. It was also found that the proportion of the Chx10 positive retinal tissue is about 70% when TFH-R1-10-2 strain is the starting material (FIG. 10A). From the analysis of serial sections, it could be confirmed that these Chx10 positive cells were Rx co-positive cells (FIG. 10B). It was found that the proportion of the Chx10 positive retinal tissue is about 90% when TFH-R2-10-F8 strain is the starting material (FIG. 10C). From the analysis of serial sections, it could be confirmed that these Chx10 positive cells were Rx co-positive cells (FIG. 10D).

From these results, it was found that human iPS cells established using Sendaivirus vector as the starting material also efficiently differentiate into a retinal tissue under conditions including a Precondition treatment in step 1 and addition of a Wnt signal transduction pathway inhibiting substance in step 2 and step 3.

Therefore, it was found that a retinal cell and/or a retinal tissue can be produced by the production method of the present application from iPS cells established using an episomal vector (e.g., 1231A3 strain) and human iPS cell established using a Sendaivirus vector (e.g., TFH-R1-10-2 strain and TFH-R2-10-F8 strain) irrespective of the establishing method of the iPS cells.

Example 9: Production Example of Retinal Cell Containing Photoreceptor Cell from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance and TGFβ Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) (step 1: Precondition (TGFβR-i+Shh) treatment) in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium, IWR-1e (3 µM) was added as a Wnt signal transduction pathway inhibiting substance, and SAG (30 nM) was added as a Sonic hedgehog signal transduction pathway activating substance, and the cells were cultured. A cell aggregate was formed by day 2 after the start of suspension culture.

On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration of exogenous IWR-1e would not change. Thereafter, a half-medium exchange operation was performed once every 2-4 days with the aforementioned serum-free medium not containing Y27632, SAG, human recombinant BMP4 and further containing IWR-1e to avoid change of the concentration of IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed.

A part of the cells on day 20 after the start of the aforementioned suspension culture was extracted, fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These stained sections were observed with an inverted fluorescence microscope (manufactured by KEYENCE CORPORATION, BIOREVO). As a result, it was found that the cells on day 20 after the start of the aforementioned suspension culture contained a neural tissue and the neural tissue was a Chx10 and Rx co-positive retinal tissue.

A part of the cells on day 20 after the start of the aforementioned suspension culture was extracted and subjected to a differentiation culture according to the method described in "Nature Communications 6, 6286 (2015)".

The cell aggregate on day 20 after the start of suspension culture were transferred to a 90 mm low adhesive culture dish (manufactured by SUMITOMO BAKELITE CO., LTD.) and cultured in a serum-free medium (DMEM/F12 medium added with 1% N2 supplement) containing a Wnt signal transduction pathway activating substance (CHIR99021, 3 µM) and an FGF signal transduction pathway inhibiting substance (SU5402, 5 µM) at 37° C., 5% $CO_2$ for 3 days, i.e., up to day 23 after the start of suspension culture. During this period, about 50 aggregates were cultured in suspension in a 10 ml serum-free medium containing the aforementioned CHIR99021 and SU5402 per one 90-mm low adhesive culture dish. On day 23 after the start of suspension culture, a thin neuroepithelium was formed, and a retinal pigment epithelial (RPE)-like tissue was formed.

The cell aggregate on day 23 after the start of suspension culture were cultured in suspension in a 90-mm low adhesive culture dish (manufactured by SUMITOMO BAKELITE CO., LTD.) in a serum-containing medium (DMEM/F12 medium added with 10% fetal calf serum, 1% N2 supplement, 0.5 µM retinoic acid, and 100 µM taurine) not containing a Wnt signal transduction pathway activating substance or an FGF signal transduction pathway inhibiting substance at 37° C., 5% $CO_2$, atmospheric oxygen concentration (about 20%) up to day 58 after the start of suspension culture (35 days). From day 20 after the start of suspension culture to the completion of the suspension culture, a half-medium exchange operation was performed once every 2-4 days with the aforementioned serum-containing medium. During this period, about 30 aggregates per one 90-mm low adhesive culture dish were cultured in suspension in 15 ml of the aforementioned serum-containing medium. A neural retina-like tissue was present from day 35 after the start of suspension culture.

The cell aggregates on day 58 after the start of suspension culture were subjected to bright field observation using an inverted microscope (manufactured by Nikon Corporation, ECLIPSE Ti). As a result, it was found that dye deposited retinal pigment epithelial cells could be formed in addition to the neural tissues (FIG. 11, A, shown with an arrowhead).

The thus-prepared cell aggregates on day 58 after the start of suspension culture were each fixed with 4% para-formaldehyde, and cryosections were prepared. These cryosections were immunostained for Rx (anti-Rax/Rx antibody, manufactured by Takara, Guinea Pig.), which is one of the retinal tissue markers, Chx10 (anti-Chx10 antibody, manufactured by Exalpha, sheep), which is one of the neural retinal progenitor cell markers, Crx (anti-Crx antibody, manufactured by Takara, rabbit), which is one of the photoreceptor precursor cell markers, and observed using an inverted fluorescence microscope (manufactured by KEYENCE CORPORATION, BIOREVO).

Figure 11:
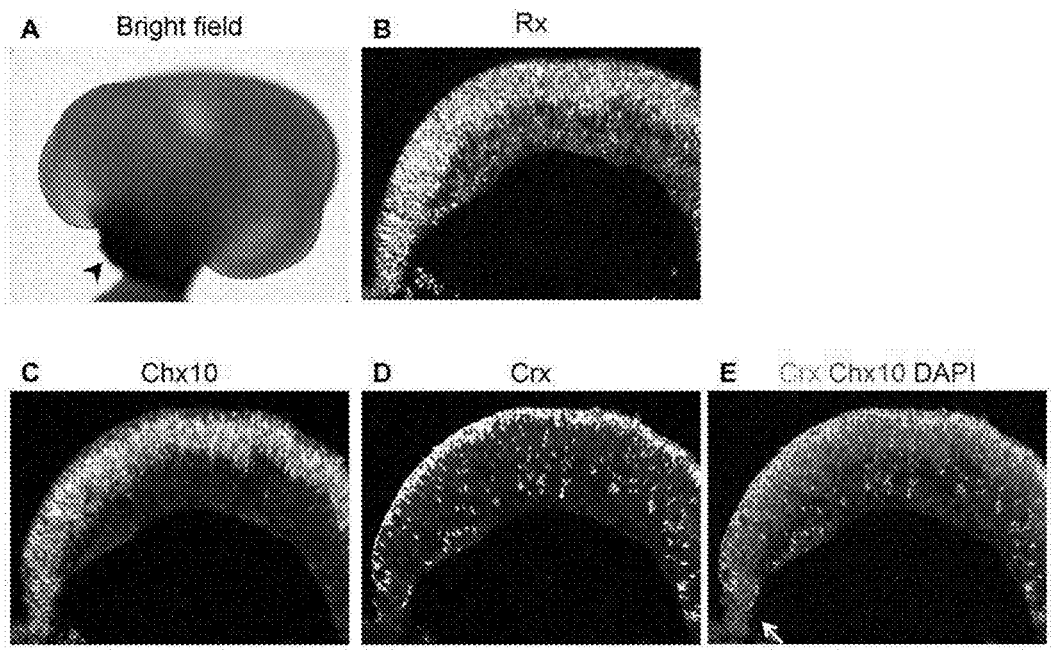
FIG. 11 shows bright field observation results of a photoreceptor cell-containing retinal tissue induced from human iPS cells (A). Observation results (B-E) of expression of Rx, Chx10 and Crx in the photoreceptor cell-containing retinal tissue by immunohistostaining are shown. Counterstained with DAPI (E).

As a result, it was found that about 90% of the Rx positive retinal tissues were formed in the cell aggregate on day 58 after the start of the aforementioned suspension culture (FIG. 11, B). It was further found that the Rx positive retinal tissues contain Chx10 positive neural retinal progenitor cells (FIG. 11, C). Also, it was found that the Rx positive retinal tissues contain Crx positive photoreceptor precursor cells (FIG. 11, D). From morphological observation, it was found that the Rx positive retinal tissues contain a ciliary marginal zone-like structure (FIG. 11, E, shown with an arrow). From morphological observation, it could be confirmed that Rx positive and Chx10 negative and Crx negative inner layer retina nerve cells (e.g., ganglion cell and amacrine cell) are contained in the inside of the retinal tissue (FIG. 11).

From these results, it was found that feeder-free cultured human iPS cells as the starting material efficiently differentiate into a retinal tissue under conditions including a Precondition treatment in step 1 and addition of a Wnt signal transduction pathway inhibiting substance in step 2 and step 3. It was further found that retinal cells (or retina layer specific nerve cells), for example, neural retinal progenitor cells, photoreceptor precursor cells, retinal pigment epithelial cells, inner layer retina nerve cells, ciliary marginal zone-like structure can be produced by continuing differentiation culture of the prepared retinal tissues. In addition, it was found that neural retinal progenitor cells, photoreceptor precursor cells, inner layer retina nerve cells form a continuous epithelial structure having a layer structure in the aforementioned retinal tissues.

That is, it was found that retinal tissues•retinal cells useful for regenerative medicine•cell transplantation treatment and evaluation study of effectiveness•safety can be produced from feeder-free cultured human pluripotent stem cells by the production method of the present application.

Example 10: Production Example of Retinal Tissue from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) (step 1: Precondition (TGFβR-i+Shh) treatment, FIG. 12 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium under three conditions of the following Conditions 1-3.

Condition 1

Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 12A-C, "Condition 1").

Condition 2

Condition including addition of IWR-1e (3 µM) as a Wnt signal transduction pathway inhibiting substance and addition of SAG (10 nM) as an exogenous Sonic hedgehog signal transduction pathway activating substance to the aforementioned serum-free medium at the start of step 2 (FIG. 12D-F "Condition 2").

Condition 3

Condition including addition of IWR-1e (3 µM) as a Wnt signal transduction pathway inhibiting substance and addition of SAG (30 nM) as an exogenous Sonic hedgehog signal transduction pathway activating substance to the aforementioned serum-free medium at the start of step 2 (FIG. 12G-I "Condition 3").

A cell aggregate was formed by day 2 after the start of suspension culture under Condition 1, Condition 2 and Condition 3 (step 2 completed, and step 3 started).

On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

On day 12 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition 1, Condition 2 and Condition 3.

Figure 12:
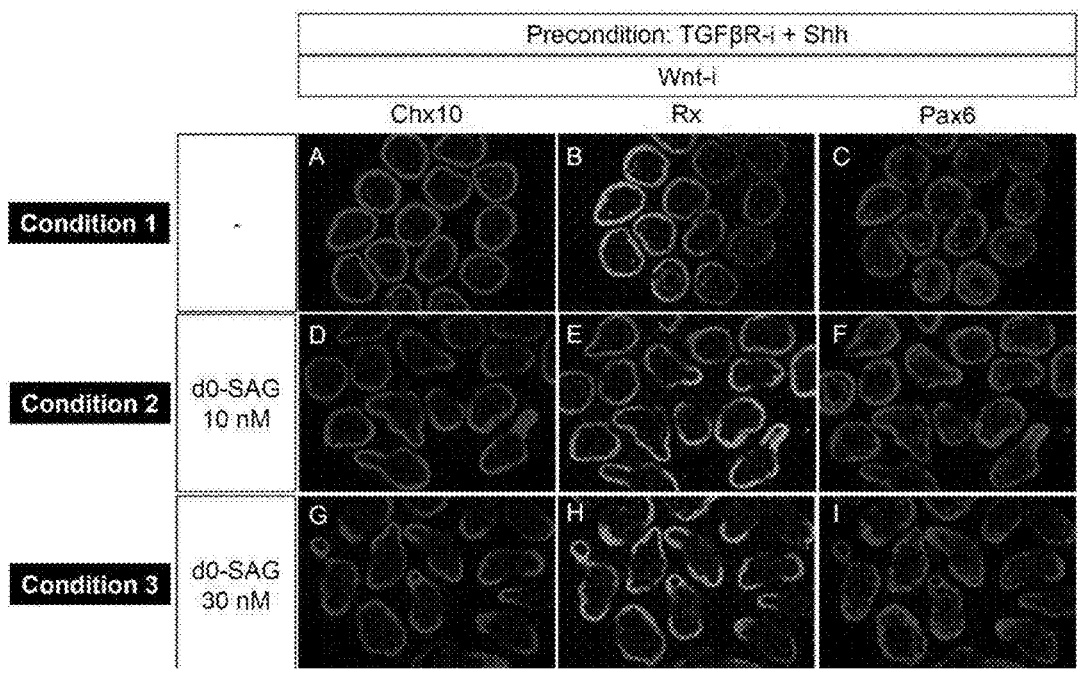
FIG. 12 shows the comparison results of expression of Chx10 (A, D, G), Rx (B, E, H) and Pax6 (C, F, I) in cell aggregates formed from human iPS cells under various culture conditions by immunohistostaining.

The aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers, or Pax6, which is one of the markers of neural tissues including a retinal tissue. These stained sections were observed with an inverted fluorescence microscope (manufactured by KEYENCE CORPORATION, BIOREVO) (FIG. 12).

As a result, it was found that a neural tissue could be formed in Condition 1, Condition 2 and Condition 3. In Condition 1, the proportion of the Chx10 positive retinal tissue was about 95% (FIG. 12A), in Condition 2, the proportion of the Chx10 positive retinal tissue was about 95% (FIG. 12D), and in Condition 3, the proportion of the Chx10 positive retinal tissue was about 85% (FIG. 12G). From the analysis of serial sections, it could be confirmed that these Chx10 positive cells are Rx and Pax6 co-positive cells.

That is, in Condition 1, it was found that efficient differentiation into a retinal tissue is also achieved under conditions including Precondition with a TGFβ signal transduction pathway inhibiting substance and a Sonic hedgehog signal transduction pathway activating substance in step 1, addition of a Wnt signal transduction pathway inhibiting substance in step 2 and step 3, and reduction of the concentration of the exogenous Wnt signal transduction pathway inhibiting substance to 3% or less in the course of step 3 (on day 12 after the start of suspension culture). Furthermore, in Condition 2 and Condition 3, it was found that efficient differentiation into retinal cell is also achieved under conditions including Precondition with a TGFβ signal transduction pathway inhibiting substance and a Sonic hedgehog signal transduction pathway activating substance in step 1, addition of a Sonic hedgehog signal transduction pathway activating substance in step 2, and addition of a Wnt signal transduction pathway inhibiting substance in step 2 and step 3.

Example 11: Production Example of Retinal Tissue from Human iPS Cell Including Precondition with Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for two days under conditions including addition of SAG (Sonic hedgehog signal transduction pathway activating substance (Shh), 300 nM) (step 1: Precondition (Shh) treatment, FIG. 13 "Precondition: Shh") in a Stem Fit (registered trade mark) medium (AK03N; manufactured by Ajinomoto Co., Inc.) (that is, a Sonic hedgehog signal transduction pathway activating substance was allowed to act for two days before start of differentiation).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium under three conditions of the following Conditions 1-3.

Condition 1

Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 13A-C, "Condition 1").

Condition 2

Condition including addition of IWR-1e (3 µM) as a Wnt signal transduction pathway inhibiting substance and addition of SAG (10 nM) as an exogenous Sonic hedgehog signal transduction pathway activating substance to the aforementioned serum-free medium at the start of step 2 (FIG. 13D-F "Condition 2").

Condition 3

Condition including addition of IWR-1e (3 µM) as a Wnt signal transduction pathway inhibiting substance and addition of SAG (30 nM) as an exogenous Sonic hedgehog signal transduction pathway activating substance to the aforementioned serum-free medium at the start of step 2 (FIG. 13G-I "Condition 3").

A cell aggregate was formed by day 2 after the start of suspension culture under Condition 1, Condition 2 and Condition 3 (step 2 completed, and step 3 started).

On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

On day 10 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition 1, Condition 2 and Condition 3.

Figure 13:
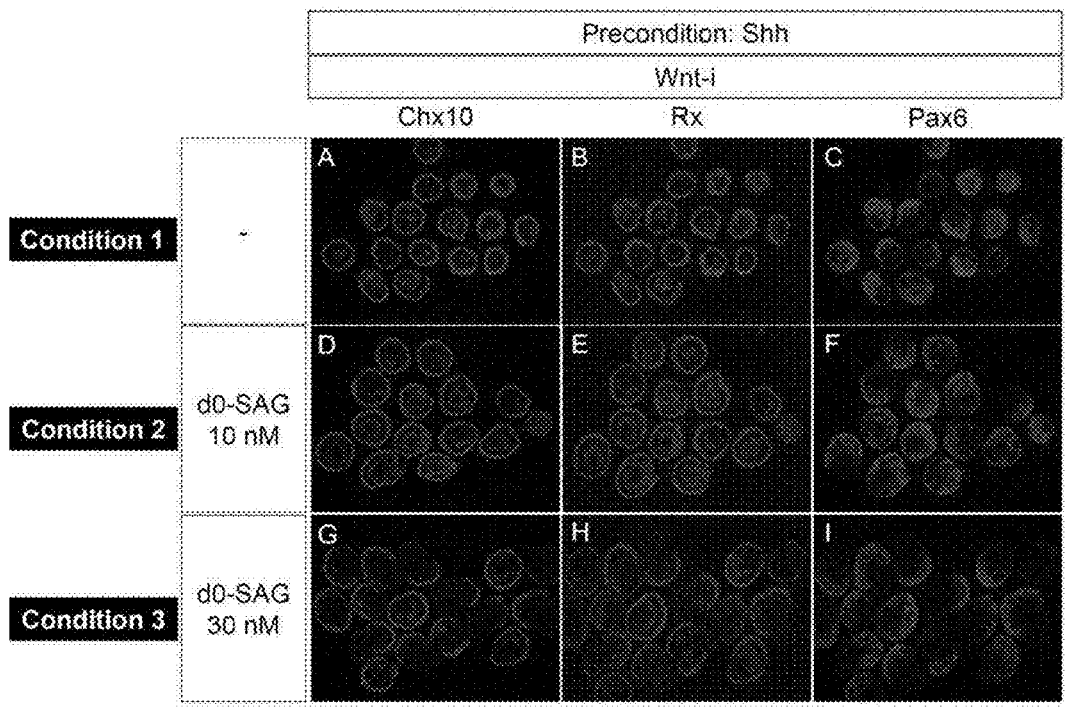
FIG. 13 shows the comparison results of expression of Chx10 (A, D, G), Rx (B, E, H) and Pax6 (C, F, I) in cell aggregates formed from human iPS cells under various culture conditions by immunohistostaining.

The cell aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers, or Pax6, which is one of the markers of neural tissues including a retinal tissue. These stained sections were observed with an inverted fluorescence microscope (manufactured by KEYENCE CORPORATION, BIOREVO) (FIG. 13).

As a result, it was found that a neural tissue was formed in Condition 1, Condition 2 and Condition 3. In Condition 1, the proportion of the Chx10 positive retinal tissue was about 95%, in Condition 2, the proportion of the Chx10 positive retinal tissue was about 90%, and in Condition 3, the proportion of the Chx10 positive retinal tissue was about 70%. From the analysis of serial sections, it could be confirmed that these Chx10 positive cells are Rx and Pax6 co-positive cells.

That is, in Condition 1, it was found that efficient differentiation into a retinal tissue is also achieved under conditions including Precondition with a Sonic hedgehog signal transduction pathway activating substance in step 1, addition of a Wnt signal transduction pathway inhibiting substance in step 2 and step 3, and reduction of the concentration of the exogenous Wnt signal transduction pathway inhibiting substance 15 to 3% or less in the course of step 3 (on day 10 after the start of suspension culture). Furthermore, in Condition 2 and Condition 3, it was found that efficient differentiation into retinal cell is also achieved under conditions including Precondition with a Sonic hedgehog signal transduction pathway activating substance in step 1, addition of a Sonic hedgehog signal transduction pathway activating substance in step 2, and addition of a Wnt signal transduction pathway inhibiting substance in step 2 and step 3.

Example 12: Production Example of Retinal Tissue Containing Photoreceptor Cell from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium of the following Condition 1.

Condition 1

Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2.

A cell aggregate was formed by day 2 after the start of suspension culture under Condition 1, Condition 2 and Condition 3 (step 2 completed, and step 3 started).

On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

On day 10 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed.

A part of the cells on day 20 after the start of the aforementioned suspension culture was extracted and subjected to a differentiation culture according to the method described in "Nature Communications 6, 6286 (2015)".

The cell aggregate on day 20 after the start of suspension culture were transferred to a 90 mm low adhesive culture dish (manufactured by SUMITOMO BAKELITE CO., LTD.) and cultured in a serum-free medium (DMEM/F12 medium added with 1% N2 supplement) containing a Wnt signal transduction pathway activating substance (CHIR99021, 3 µM) and an FGF signal transduction pathway inhibiting substance (SU5402, 5 µM) at 37° C., 5% $CO_2$ for 3 days, i.e., up to day 23 after the start of suspension culture. During this period, about 50 aggregates were cultured in suspension in a 10 ml serum-free medium containing the aforementioned CHIR99021 and SU5402 per one 90-mm low adhesive culture dish. On day 23 after the start of suspension culture, a thin neuroepithelium was formed, and a retinal pigment epithelial (RPE)-like tissue was formed.

The cell aggregate on day 23 after the start of suspension culture were cultured in suspension in a 90-mm low adhesive culture dish (manufactured by SUMITOMO BAKELITE CO., LTD.) in a serum-containing medium (DMEM/F12 medium added with 10% fetal calf serum, 1% N2 supplement, 0.5 µM retinoic acid, and 100 µM taurine) not containing a Wnt signal transduction pathway activating substance or an FGF signal transduction pathway inhibiting substance at 37° C., 5% $CO_2$, atmospheric oxygen concentration (about 20%) up to day 85 after the start of suspension culture (62 days). From day 23 after the start of suspension culture to the completion of the suspension culture, once every 2-4 days, a half-medium exchange operation was performed once every 2-4 days with the aforementioned serum-containing medium. During this period, about 30 aggregates per one 90-mm low adhesive culture dish were cultured in suspension in 15 ml of the aforementioned serum-containing medium. A neural retina-like tissue was present from day 35 after the start of suspension culture.

The cell aggregates on day 85 after the start of suspension culture were subjected to bright field observation using an inverted microscope (manufactured by Nikon Corporation, ECLIPSE Ti). As a result, it was found that a neural tissue having a continuous epithelial structure was formed (FIG. 14A).

The thus-prepared cell aggregates on day 85 after the start of suspension culture were each fixed with 4% para-formaldehyde, and cryosections were prepared. These cryosections were immunostained for Crx (anti-Crx antibody, manufactured by Takara, rabbit), which is one of the photoreceptor precursor cell markers, Chx10 (anti-Chx10 antibody, manufactured by Exalpha, sheep), which is one of the neural retinal progenitor cell markers, Rx (anti-Rax/Rx antibody, manufactured by Takara, Guinea Pig.), which is one of the retinal tissue markers, Recoverin (anti-Recoverin antibody, manufactured by Proteintech, rabbit), which is one of the photoreceptor cell markers, NRL (anti-NRL antibody, manufactured by R and D, goat), which is one of the rod photoreceptor precursor cell markers, RXR-gamma (anti-RXRG antibody, manufactured by R and D, goat), which is one of the corn photoreceptor precursor cell markers, N-cadherin (anti-N-cadherin antibody, manufactured by BD, mouse), which is one of the neural tissue markers, Aqp1 (anti-Aqp1 antibody, manufactured by Millipore, rabbit), which is one of the RPE and ciliary margin markers, and observed using an inverted fluorescence microscope (manufactured by KEYENCE CORPORATION, BIOREVO). As counterstaining, nucleic acid was stained with DAPI.

Figure 14:
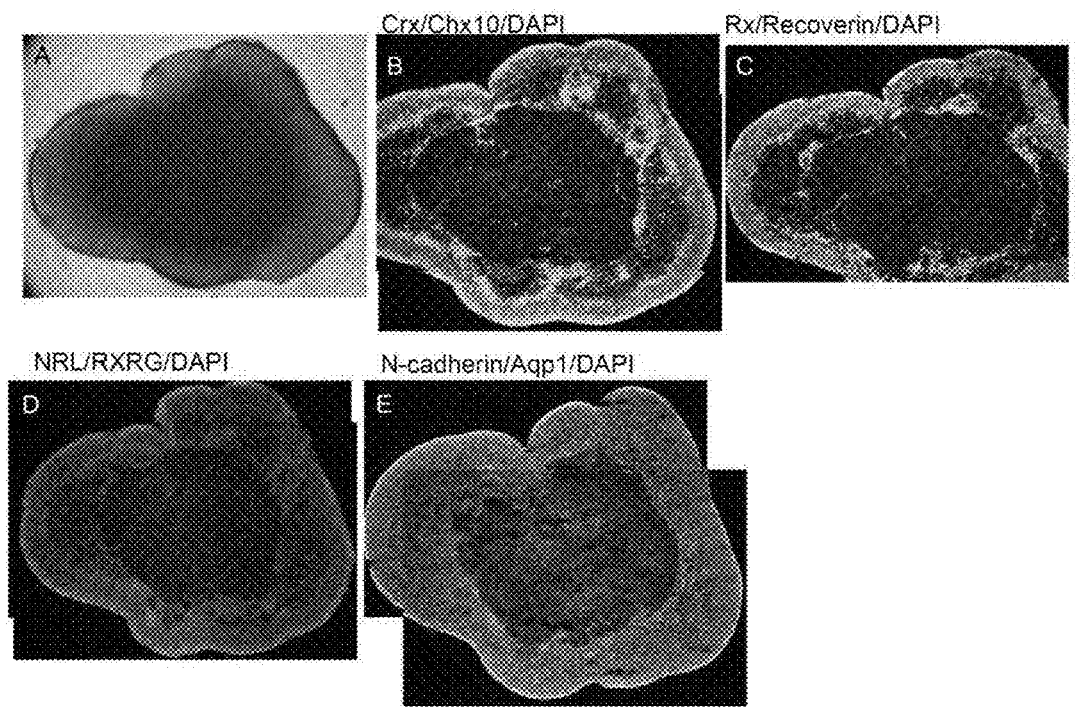
FIG. 14 shows bright field observation results of a photoreceptor cell-containing retinal tissue induced from human iPS cells (A). Observation results (B-E) of expression of Crx, Chx10, Rx, Recoverin, NRL, RXRG, N-cadherin and Aqp1 in the photoreceptor cell-containing retinal tissue by immunohistostaining are shown. Counterstained with DAPI (B-E).

As a result, it was found that about 90% of retinal tissues containing Chx10 positive neural retinal progenitor cells and Crx positive photoreceptor precursor cells were formed in the aforementioned cell aggregates on day 85 after the start of suspension culture (FIG. 14, B). From the analysis of serial sections, it was found that the retinal tissue was an Rx positive retinal tissue and contained Recoverin positive photoreceptor cell (FIG. 14, C). From the analysis of serial sections, it was found that the retinal tissue contained NRL positive rod photoreceptor precursor cells and RXR-gamma positive corn photoreceptor precursor cells (FIG. 14, D). Also, it was found that the retinal tissue was an N-cadherin positive neural tissue (FIG. 14E).

From these results, it was found that feeder-free cultured human iPS cells as the starting material efficiently differentiate into a retinal tissue under conditions including a Precondition treatment with a TGFβ signal transduction pathway inhibiting substance and a Sonic hedgehog signal transduction pathway activating substance in step 1 and addition of a Wnt signal transduction pathway inhibiting substance in step 2 and step 3. It was further found that retinal cells (or retina specific nerve cells), for example, neural retinal progenitor cell, photoreceptor precursor cell, photoreceptor cell, corn photoreceptor precursor cell, rod photoreceptor precursor cell can be produced by continuing differentiation culture of the prepared retinal tissues. In addition, it was found that neural retinal progenitor cells, photoreceptor precursor cells, photoreceptor cell form a continuous epithelial structure having a layer structure in the aforementioned retinal tissues.

Example 13: Production Example of Retinal Tissue Containing Photoreceptor Cell from Human iPS Cell Including Precondition with Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for two days under conditions including addition of SAG (Sonic hedgehog signal transduction pathway activating substance (Shh), 300 nM) (step 1: Precondition (Shh) treatment, FIG. 15) in a Stem Fit (registered trade mark) medium (AK03N; manufactured by Ajinomoto Co., Inc.) (that is, Sonic hedgehog signal transduction pathway activating substance was allowed to act for two days before start of differentiation).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium under three conditions of the following Conditions.

Condition 1

Condition including addition of IWR-1e (3 µM) as a Wnt signal transduction pathway inhibiting substance and addition of SAG (30 nM) as an exogenous Sonic hedgehog signal transduction pathway activating substance to the aforementioned serum-free medium at the start of step 2.

A cell aggregate was formed by day 2 after the start of suspension culture under Condition 1, Condition 2 and Condition 3 (step 2 completed, and step 3 started).

On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

On day 9 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 19 after the start of suspension culture were subjected to bright field observation using an inverted microscope (manufactured by Nikon Corporation, ECLIPSE Ti). As a result, it was found that a neural tissue was formed.

A part of the cells on day 19 after the start of the aforementioned suspension culture was extracted and subjected to a differentiation culture according to the method described in "Nature Communications 6, 6286 (2015)".

The cell aggregate on day 19 after the start of suspension culture were transferred to a 90 mm low adhesive culture dish (manufactured by SUMITOMO BAKELITE CO., LTD.) and cultured in a serum-free medium (DMEM/F12 medium added with 1% N2 supplement) containing a Wnt signal transduction pathway activating substance (CHIR99021, 3 µM) and an FGF signal transduction pathway inhibiting substance (SU5402, 5 µM) at 37° C., 5% $CO_2$ for 3 days, i.e., up to day 22 after the start of suspension culture. During this period, about 50 aggregates were cultured in suspension in 10 ml of a serum-free medium containing the aforementioned CHIR99021 and SU5402 per one 90-mm low adhesive culture dish. On day 22 after the start of suspension culture, a thin neuroepithelium was formed, and a retinal pigment epithelial (RPE)-like tissue was formed.

The cell aggregate on day 22 after the start of suspension culture were cultured in suspension in a 90-mm low adhesive culture dish (manufactured by SUMITOMO BAKELITE CO., LTD.) in a serum-containing medium (DMEM/F12 medium added with 10% fetal calf serum, 1% N2 supplement, 0.5 µM retinoic acid, and 100 µM taurine) not containing a Wnt signal transduction pathway activating substance or an FGF signal transduction pathway inhibiting substance at 37° C., 5% $CO_2$, atmospheric oxygen concentration (about 20%) up to day 92 after the start of suspension culture (70 days). From day 20 after the start of suspension culture to the completion of the suspension culture, once every 2-4 days, a half-medium exchange operation was performed once every 2-4 days with the aforementioned serum-containing medium. During this period, about 30 aggregates per one 90-mm low adhesive culture dish were cultured in suspension in 15 ml of the aforementioned serum-containing medium. A neural retina-like tissue was present from day 35 after the start of suspension culture.

The cell aggregates on day 92 after the start of suspension culture were subjected to bright field observation using an inverted microscope (manufactured by Nikon Corporation, ECLIPSE Ti). As a result, it was found that a neural tissue having a continuous epithelial structure was formed (FIG. 15A).

The thus-prepared cell aggregates on day 92 after the start of suspension culture were each fixed with 4% para-formaldehyde, and cryosections were prepared. These cryosections were immunostained for Crx (anti-Crx antibody, manufactured by Takara, rabbit), which is one of the photoreceptor precursor cell markers, Chx10 (anti-Chx10 antibody, manufactured by Exalpha, sheep), which is one of the neural retinal progenitor cell markers, Rx (anti-Rax/Rx antibody, manufactured by Takara, Guinea Pig.), which is one of the retinal tissue markers, Recoverin (anti-Recoverin antibody, manufactured by Proteintech, rabbit), which is one of the photoreceptor cell markers, NRL (anti-NRL antibody, manufactured by R and D, goat), which is one of the rod photoreceptor precursor cell markers, RXR-gamma (anti-RXRG antibody, manufactured by R and D, goat), which is one of the corn photoreceptor precursor cell markers, N-cadherin (anti-N-cadherin antibody, manufactured by BD, mouse), which is one of the neural tissue markers, Aqp1 (anti-Aqp1 antibody, manufactured by Millipore, rabbit), which is one of the RPE and ciliary margin markers, and observed using an inverted fluorescence microscope (manufactured by KEYENCE CORPORATION, BIOREVO). As counterstaining, nucleic acid was stained with DAPI.

As a result, it was found that about 80% of retinal tissues containing Chx10 positive neural retinal progenitor cells and Crx positive photoreceptor precursor cells were formed in the aforementioned cell aggregates on day 92 after the start of suspension culture (FIG. 15, B). From the analysis of serial sections, it was found that the retinal tissue was an Rx positive retinal tissue and contained Recoverin positive photoreceptor cell (FIG. 15, C). From the analysis of serial sections, it was found that the retinal tissue contained NRL positive rod photoreceptor precursor cells and RXR-gamma positive corn photoreceptor precursor cells (FIG. 15, D).

Also, from the analysis of serial sections, it was found that the retinal tissue was an N-cadherin positive neural tissue (FIG. 15, E). From the analysis of serial sections, it was found that the retinal tissue contained Aqp1 positive ciliary margin-like structure (FIG. 15, E).

From these results, it was found that feeder-free cultured human iPS cells as the starting material efficiently differentiate into a retinal tissue under conditions including a Precondition treatment with a Sonic hedgehog signal transduction pathway activating substance in step 1, addition of a Sonic hedgehog signal transduction pathway activating substance in step 2, and addition of a Wnt signal transduction pathway inhibiting substance in step 2 and step 3. It was further found that retinal cells (or retina specific nerve cells), for example, neural retinal progenitor cell, photoreceptor precursor cell, photoreceptor cell, corn photoreceptor precursor cell, rod photoreceptor precursor cell, ciliary margin-like structure can be produced by continuing differentiation culture of the prepared retinal tissues. In addition, it was found that neural retinal progenitor cells, photoreceptor precursor cells, photoreceptor cell form a continuous epithelial structure having a layer structure in the aforementioned retinal tissues.

Example 14: Production Example of Retinal Tissue from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) (step 1: Precondition (TGFβR-i+Shh) treatment, FIG. 16 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (Prime-Surface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 6% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium under the following Condition.

Condition. Condition including addition of IWR-1e (3 µM) as a Wnt signal transduction pathway inhibiting substance and addition of SAG (30 nM) as an exogenous Sonic hedgehog signal transduction pathway activating substance to the aforementioned serum-free medium at the start of step 2 (FIG. 16, A, B).

A cell aggregate was formed by day 2 after the start of suspension culture (step 2 completed, and step 3 started).

Furthermore, the cells were cultured in a serum-free medium under two conditions of the following Conditions A, B.

Condition A. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

Condition B. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration of exogenous IWR-1e would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e such that the concentration of exogenous human recombinant BMP4 and the concentration of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

After culturing under two conditions of the above-mentioned Conditions A, B, the cells were further cultured as follows.

On day 12 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 18 after the start of suspension culture were subjected to bright field observation using an inverted microscope (manufactured by Nikon Corporation, ECLIPSE Ti). As a result, it was found that a neural tissue was formed under Condition A and Condition B.

The aggregates on day 18 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 16A, B).

As a result, it was found that a neural tissue was formed under Condition A and Condition B. In Condition A, the proportion of the Chx10 positive retinal tissue was about 80%, and in Condition B, the proportion of the Chx10 positive retinal tissue was about 80%.

That is, it was found that efficient differentiation into a retinal tissue is also achieved, when the addition condition of exogenous BMP is any condition of Condition A and Condition B, under conditions including Precondition with a TGFβ signal transduction pathway inhibiting substance and a Sonic hedgehog signal transduction pathway activating substance in step 1, addition of a Sonic hedgehog signal transduction pathway activating substance in step 2, addition of a Wnt signal transduction pathway inhibiting substance in step 2 and step 3, reduction of the concentration of the exogenous Wnt signal transduction pathway inhibiting substance to 3% or less in the course of step 3 (On day 12 after the start of suspension culture), and the concentration of KSR contained in the aforementioned serum-free medium of 6%.

Example 15: Production Example of Retinal Tissue from Human iPS Cell Including Precondition with Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for two days under conditions including addition of SAG (Sonic hedgehog signal transduction pathway activating substance (Shh), 300 nM) (step 1: Precondition (+Shh) treatment, FIG. 16 "Precondition: Shh") in a Stem Fit (registered trade mark) medium (AK03N; manufactured by Ajinomoto Co., Inc.).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 6% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium and the cells were cultured in a serum-free medium under the following Condition.

Condition. Condition including addition of IWR-1e (3 μM) as a Wnt signal transduction pathway inhibiting substance and no addition of an exogenous Sonic hedgehog signal transduction pathway activating substance to the aforementioned serum-free medium at the start of step 2 (FIG. 16, C, D).

A cell aggregate was formed by day 2 after the start of suspension culture (step 2 completed, and step 3 started).

Furthermore, the cells were cultured in a serum-free medium under two conditions of the following Conditions C and D.

Condition C. On day 3 after the start of suspension culture, a medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration (3 μM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

Condition D. On day 3 after the start of suspension culture, a medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration of exogenous IWR-1e would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e such that the concentration of exogenous human recombinant BMP4 and the concentration of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

After culturing under two conditions of the above-mentioned Conditions C and D, the cells were cultured as follows.

On day 12 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 18 after the start of suspension culture were subjected to bright field observation using an inverted microscope (manufactured by Nikon Corporation, ECLIPSE Ti). As a result, it was found that a neural tissue was formed under Condition C and Condition D.

The aggregates on day 18 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 16C, D).

As a result, it was found that a neural tissue was formed under Condition C and Condition D. In Condition C, the proportion of the Chx10 positive retinal tissue was about 80%, and in Condition D, the proportion of the Chx10 positive retinal tissue was about 80%.

That is, it was found that efficient differentiation into a retinal tissue is also achieved, when the addition condition of exogenous BMP is any condition of Condition C and Condition D, under conditions including Precondition with a Sonic hedgehog signal transduction pathway activating substance in step 1, addition of a Wnt signal transduction pathway inhibiting substance in step 2 and step 3, reduction of the concentration of the exogenous Wnt signal transduction pathway inhibiting substance to 3% or less in the course of step 3 (On day 12 after the start of suspension culture), and the concentration of KSR contained in the aforementioned serum-free medium of 6%.

Example 16: Production Example of Retinal Tissue from Human iPS Cell Including Precondition with BMP Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of LDN193189 (BMP signal transduction pathway inhibiting substance (BMPR-i), 100 nM) and SAG (Sonic hedgehog signal transduction pathway activating substance (Shh), 300 nM) (step 1: Precondition (BMPR-i+Shh) treatment, FIG. 17 "Precondition: BMPR-i+Shh") in a Stem Fit (registered trade mark) medium (AK03N; manufactured by Ajinomoto Co., Inc.).

The thus-prepared Precondition (BMPR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium under the following Condition.

Condition 1

Figure 17:
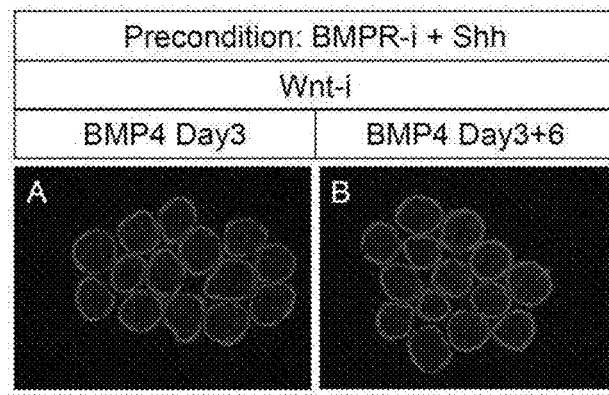
FIG. 17 shows the comparison results of expression of Chx10 in cell aggregates formed from human iPS cells under various culture conditions by immunohistostaining.

Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 17, A, B).

A cell aggregate was formed by day 2 after the start of suspension culture (step 2 completed, and step 3 started).

Furthermore, the cells were cultured in a serum-free medium under two conditions of the following Conditions A, B.

Condition A. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

Condition B. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e such that the concentration of exogenous human recombinant BMP4 and the concentration of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

After culturing under two conditions of the above-mentioned Conditions A, B, the cells were cultured as follows.

On day 10 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition A and Condition B.

The aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 17A, B).

As a result, it was found that a neural tissue was formed under Condition A and Condition B. In Condition A, the proportion of the Chx10 positive retinal tissue was about 90%, and in Condition B, the proportion of the Chx10 positive retinal tissue was about 90%.

That is, it was found that efficient differentiation into a retinal tissue is also achieved, when the addition condition of exogenous BMP is any condition of Condition A and Condition B, under conditions including Precondition with a BMP signal transduction pathway inhibiting substance and a Sonic hedgehog signal transduction pathway activating substance in step 1, addition of a Wnt signal transduction pathway inhibiting substance in step 2 and step 3, and reduction of the concentration of the exogenous Wnt signal transduction pathway inhibiting substance to 3% or less in the course of step 3 (On day 10 after the start of suspension culture).

Example 17: Production Example of Retinal Tissue from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for one day under conditions including addition of SAG (Sonic hedgehog signal transduction pathway activating substance (Shh), 300 nM) in a Stem Fit (registered trade mark) medium (AK03N; manufactured by Ajinomoto Co., Inc.), whereby human iPS cells one day before subconfluence were prepared. Furthermore, human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) in a Stem Fit (registered trade mark) medium (AK03N; manufactured by Ajinomoto Co., Inc.) (step 1: Precondition (TGFβR-i 24h+Shh 48h) treatment, FIG. 18).

The thus-prepared Precondition (TGFβR-i 24h+Shh 48h)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in a serum-free medium under the following Condition.

Figure 18:
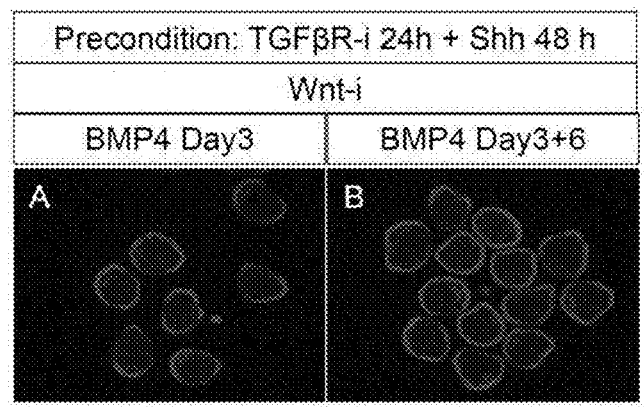
FIG. 18 shows the comparison results of expression of Chx10 in cell aggregates formed from human iPS cells under various culture conditions by immunohistostaining.

Condition. Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 18, A, B).

A cell aggregate was formed by day 2 after the start of suspension culture (step 2 completed, and step 3 started).

Furthermore, the cells were cultured in a serum-free medium under two conditions of the following Conditions A, B.

Condition A. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

Condition B. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e such that the concentration of exogenous human recombinant BMP4 and the concentration of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

After culturing under two conditions of the above-mentioned Conditions A, B, the cells were further cultured as follows.

On day 10 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition A and Condition B.

The aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 18A, B).

As a result, it was found that a neural tissue was formed under Condition A and Condition B. In Condition A, the proportion of the Chx10 positive retinal tissue was about 80%, and in Condition B, the proportion of the Chx10 positive retinal tissue was about 80%.

That is, it was found that efficient differentiation into a retinal tissue is also achieved, when the addition condition of exogenous BMP is any condition of Condition A and Condition B, under conditions including Precondition with a TGFβ signal transduction pathway inhibiting substance and a Sonic hedgehog signal transduction pathway activating substance in step 1, addition of a Wnt signal transduction pathway inhibiting substance in step 2 and step 3, and reduction of the concentration of the exogenous Wnt signal transduction pathway inhibiting substance to 3% or less in the course of step 3 (On day 10 after the start of suspension culture).

Example 18: Production Example of Retinal Tissue from Human iPS Cell Including Precondition with BMP Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for one day under conditions including addition of SAG (Sonic hedgehog signal transduction pathway activating substance (Shh), 300 nM) in a Stem Fit (registered trade mark) medium (AK03N; manufactured by Ajinomoto Co., Inc.), whereby human iPS cells one day before subconfluence were prepared. Furthermore, human iPS cells one day before subconfluence were feeder-free cultured for one day under conditions including addition of LDN193189 (BMP signal transduction pathway inhibiting substance (BMPR-i), 100 nM) and SAG (Sonic hedgehog signal transduction pathway activating substance (Shh), 300 nM) in a Stem Fit (registered trade mark) medium (AK03N; manufactured by Ajinomoto Co., Inc.) (step 1: Precondition (BMPR-i 24h+Shh 48h) treatment, FIG. 19).

The thus-prepared Precondition (BMPR-i 24h+Shh 48h)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (Prime-Surface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium and the cells were cultured in the serum-free medium under the following Condition.

Figure 19:
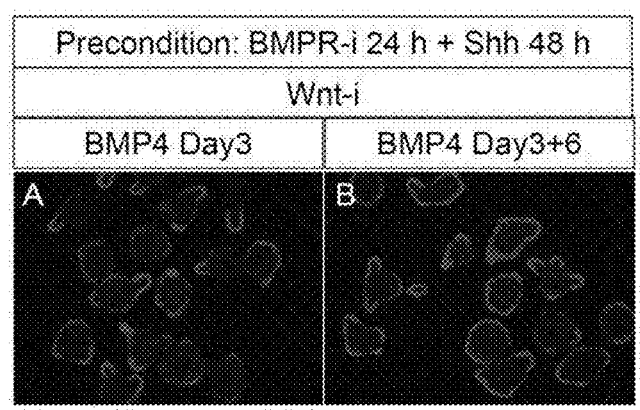
FIG. 19 shows the comparison results of expression of Chx10 in cell aggregates formed from human iPS cells under various culture conditions by immunohistostaining.

Condition. Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 19, A, B).

A cell aggregate was formed by day 2 after the start of suspension culture (step 2 completed, and step 3 started).

Furthermore, the cells were cultured in a serum-free medium under two conditions of the following Conditions A, B.

Condition A. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

Condition B. On day 3 after the start of suspension culture, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e such that the concentration of exogenous human recombinant BMP4 and the concentration of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

The cells were cultured as follows under two conditions of the above-mentioned Conditions A, B.

On day 10 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition A and Condition B.

The aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 19A, B).

As a result, it was found that a neural tissue was formed under Condition A and Condition B. In Condition A, the proportion of the Chx10 positive retinal tissue was about 50%, and in Condition B, the proportion of the Chx10 positive retinal tissue was about 70%.

That is, it was found that differentiation into a retinal tissue is also achieved, when the addition condition of exogenous BMP is any condition of Condition A and Condition B, under conditions including Precondition with a BMP signal transduction pathway inhibiting substance and a Sonic hedgehog signal transduction pathway activating substance in step 1, addition of a Wnt signal transduction pathway inhibiting substance in step 2 and step 3, and reduction of the concentration of the exogenous Wnt signal transduction pathway inhibiting substance to 3% or less in the course of step 3 (On day 10 after the start of suspension culture).

Example 19: Production Example of Retinal Tissue from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance and TGFβ Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 µM) and SAG (Sonic hedgehog signal transduction pathway activating substance (Shh), 300 nM) (step 1: Precondition (TGFβR-i+Shh) treatment, FIG. 20 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium, and the cells were cultured in the serum-free medium under following Condition.

Figure 20:
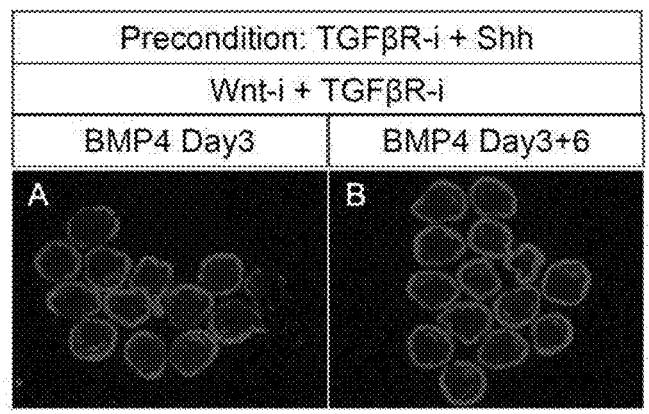
FIG. 20 shows the comparison results of expression of Chx10 in cell aggregates formed from human iPS cells under various culture conditions by immunohistostaining.

Condition. Condition including addition of IWR-1e (3 µM) as a Wnt signal transduction pathway inhibiting substance and SB431542 (5 µM) as TGFβ signal transduction pathway inhibiting substance, and no addition of an exogenous Sonic hedgehog signal transduction pathway activating substance to the aforementioned serum-free medium at the start of step 2 (FIG. 20, A, B).

A cell aggregate was formed by day 2 after the start of suspension culture (step 2 completed, and step 3 started).

Furthermore, the cells were cultured in a serum-free medium under two conditions of the following Conditions A, B.

Condition A. On day 3 after the start of suspension culture, a medium not containing Y27632 or SAG, containing human recombinant BMP4 (manufactured by R&D) and further containing IWR-1e and SB431542 was added by 50 µl such that a final concentration of exogenous human recombinant BMP4 would be 1.5 nM (55 ng/ml) and the concentrations of exogenous IWR-1e (3 µM) and SB431542 (5 µM) would not change. Thereafter, a half-medium exchange operation was performed once every 2-4 days with the serum-free medium not containing Y27632, SAG, human recombinant BMP4 and further containing IWR-1e and SB431542 to avoid change of the concentration of exogenous IWR-1e and SB431542.

Condition B. On day 3 after the start of suspension culture, a medium not containing Y27632 or SAG, containing human recombinant BMP4 (manufactured by R&D) and further containing IWR-1e and SB431542 was added by 50 µl such that a final concentration of exogenous human recombinant BMP4 would be 1.5 nM (55 ng/ml) and the concentrations of exogenous IWR-1e (3 µM) and SB431542 (5 µM) would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e and SB431542 such that the concentration of exogenous human recombinant BMP4 and the concentration of exogenous IWR-1e and SB431542 would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e and SB431542.

The cells were further cultured as follows after culturing under two conditions of the above-mentioned Conditions A, B.

On day 10 after the start of suspension culture, a 80% medium exchange operation was performed 3 times by using the aforementioned serum-free medium so that the concentration of exogenous IWR-1e and SB431542 would be 3% or less as compared to that before medium exchange. Thereafter, a half-medium exchange operation was performed once every 2-4 days with the aforementioned serum-free medium not containing Y27632, SAG, human recombinant BMP4, IWR-1e and SB431542.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition A and Condition B.

The aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 20A, B).

As a result, it was found that a neural tissue was formed under Condition A and Condition B. In Condition A, the proportion of the Chx10 positive retinal tissue was about 95%, and in Condition B, the proportion of the Chx10 positive retinal tissue was about 95%.

That is, it was found that efficient differentiation into a retinal tissue is also achieved, when the addition condition of exogenous BMP is any condition of Condition A and Condition B, under conditions including Precondition with a TGFβ signal transduction pathway inhibiting substance and a Sonic hedgehog signal transduction pathway activating substance in step 1, addition of a Wnt signal transduction pathway inhibiting substance and a TGFβ signal transduction pathway inhibiting substance in step 2 and step 3, and reduction of the concentration of the exogenous Wnt signal transduction pathway inhibiting substance and a TGFβ signal transduction pathway inhibiting substance to 3% or less in the course of step 3 (On day 10 after the start of suspension culture).

Example 20: Production Example of Retinal Tissue from Human iPS Cell Including Precondition with Sonic Hedgehog Signal Transduction Pathway Activating Substance in Step 1 and Use of Wnt Signal Transduction Pathway Inhibiting Substance and TGFβ Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for two days under conditions including addition of SAG (Sonic hedgehog signal transduction pathway activating substance (Shh), 300 nM) (step 1: Precondition (Shh) treatment, FIG. 21 "Precondition: Shh 48 h") in a Stem Fit (registered trade mark) medium (AK03N; manufactured by Ajinomoto Co., Inc.).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 it of a serum-free medium at $1.0 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium, and the cells were cultured in the serum-free medium. A cell aggregate was formed by day 2 after the start of suspension culture.

Figure 21:
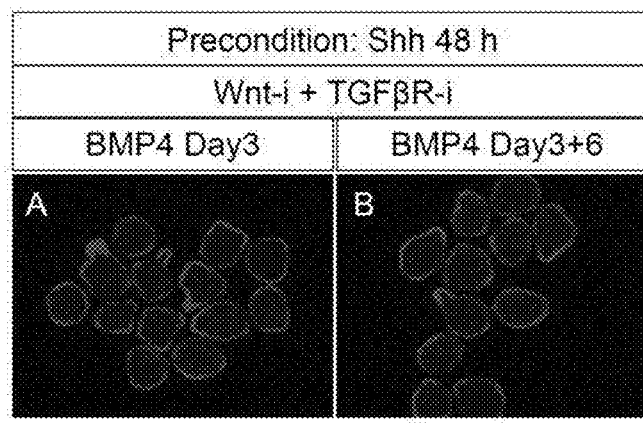
FIG. 21 shows the comparison results of expression of Chx10 in cell aggregates formed from human iPS cells under various culture conditions by immunohistostaining.

Condition. Condition including addition of IWR-1e (3 μM) as a Wnt signal transduction pathway inhibiting substance and SB431542 (5 μM) as a TGFβ signal transduction pathway inhibiting substance, and no addition of an exogenous Sonic hedgehog signal transduction pathway activating substance to the aforementioned serum-free medium at the start of step 2 (FIG. 21, A, B).

A cell aggregate was formed by day 2 after the start of suspension culture (step 2 completed, and step 3 started).

Furthermore, the cells were cultured in a serum-free medium under two conditions of the following Conditions A, B.

Condition A. On day 3 after the start of suspension culture, a medium not containing Y27632 or SAG, containing human recombinant BMP4 (manufactured by R&D) and further containing IWR-1e and SB431542 was added by 50 μl such that a final concentration of exogenous human recombinant BMP4 would be 1.5 nM (55 ng/ml) and the concentrations of exogenous IWR-1e (3 μM) and SB431542 (5 μM) would not change. Thereafter, a half-medium exchange operation was performed once every 2-4 days with the serum-free medium not containing Y27632, SAG, human recombinant BMP4 and further containing IWR-1e and SB431542 to avoid change of the concentration of exogenous IWR-1e and SB431542.

Condition B. On day 3 after the start of suspension culture, a medium not containing Y27632 or SAG, containing human recombinant BMP4 (manufactured by R&D) and further containing IWR-1e and SB431542 was added by 50 μl such that a final concentration of exogenous human recombinant BMP4 would be 1.5 nM (55 ng/ml) and the concentrations of exogenous IWR-1e (3 μM) and SB431542 (5 μM) would not change. Further, On day 6 after the start of suspension culture, a half-medium exchange operation was performed using the aforementioned serum-free medium not containing Y27632 or SAG and containing human recombinant BMP4 (manufactured by R&D) and IWR-1e and SB431542 such that the concentration of exogenous human recombinant BMP4 and the concentration of exogenous IWR-1e would not change. Thereafter, a half-medium exchange operation was performed once every 2-4 days with the serum-free medium not containing Y27632, SAG, human recombinant BMP4 and further containing IWR-1e and SB431542 to avoid change of the concentration of exogenous IWR-1e and SB431542.

The cells cultured under two conditions of the above-mentioned Conditions A, B were cultured as follows.

On day 10 after the start of suspension culture, a 80% medium exchange operation was performed 3 times by using the aforementioned serum-free medium so that the concentration of exogenous IWR-1e and SB431542 would be 3% or less as compared to that before medium exchange. Thereafter, a half-medium exchange operation was performed once every 2-4 days with the aforementioned serum-free medium not containing Y27632, SAG, human recombinant BMP4, IWR-1e and SB431542.

The thus-prepared cells on day 20 after the start of suspension culture were subjected to bright field observation using an inverted microscope (manufactured by Nikon Corporation, ECLIPSE Ti). As a result, it was found that a neural tissue was formed under Condition A and Condition B.

The aggregates on day 20 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers. These stained sections were observed with an inverted fluorescence microscope (manufactured by KEYENCE CORPORATION, BIOREVO) (FIG. 21A, B).

As a result, it was found that a neural tissue was formed under Condition A and Condition B. In Condition A, the proportion of the Chx10 positive retinal tissue was about 80%, and in Condition B, the proportion of the Chx10 positive retinal tissue was about 80%.

That is, it was found that efficient differentiation into a retinal tissue is also achieved, when the addition condition of exogenous BMP is any condition of Condition A and Condition B, under conditions including Precondition with a Sonic hedgehog signal transduction pathway activating substance in step 1, addition of a Wnt signal transduction pathway inhibiting substance and a TGFβ signal transduction pathway inhibiting substance in step 2 and step 3, and reduction of the concentration of the exogenous Wnt signal transduction pathway inhibiting substance and a TGFβ signal transduction pathway inhibiting substance to 3% or less in the course of step 3 (On day 10 after the start of suspension culture).

Example 21: Production Example of Retinal Tissue from Human iPS Cell Including Precondition with Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for two days under conditions including addition of SAG (Sonic hedgehog signal transduction pathway activating substance (Shh), 300 nM) (step 1: Precondition (Shh) treatment, FIG. 22) in a Stem Fit (registered trade mark) medium (AK03N; manufactured by Ajinomoto Co., Inc.).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.3 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium, and the cells were cultured in the serum-free medium under the following Condition and Condition 2.

Condition 1
Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 22A, B).

Condition 2
Condition including addition of IWR-1e (3 µM) as a Wnt signal transduction pathway inhibiting substance and addition of SAG (10 nM) as an exogenous Sonic hedgehog signal transduction pathway activating substance to the aforementioned serum-free medium at the start of step 2 (FIG. 22C, D).

A cell aggregate was formed by day 2 after the start of suspension culture under Condition 1 and Condition 2 (step 2 completed, and step 3 started).

On day 3 after the start of suspension culture, under Condition 1 and Condition 2, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change.

On day 6 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 18 after the start of suspension culture were subjected to bright field observation using an inverted microscope (manufactured by Nikon Corporation, ECLIPSE Ti). As a result, it was found that a neural tissue was formed under Condition 1 and Condition 2.

The aggregates on day 18 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig), which is one of retinal tissue markers. These stained sections were observed with an inverted fluorescence microscope (manufactured by KEYENCE CORPORATION, BIOREVO).

Figure 22:
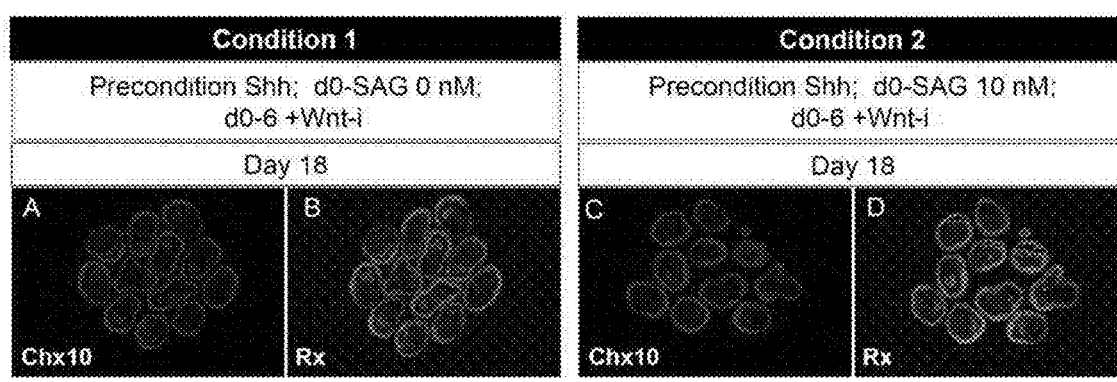
FIG. 22 shows the comparison results of expression of Chx10 and Rx in cell aggregates formed from human iPS cells under various culture conditions by immunohistostaining.

As a result, it was found that a neural tissue was formed under Condition 1 and Condition 2. In Condition 1, the proportion of the Chx10 positive retinal tissue was about 90% (FIG. 22A), and in Condition 2, the proportion of the Chx10 positive retinal tissue was about 80% (FIG. 22C). From the analysis of serial sections, it was found that the Chx10 positive cell in Condition 1 and Condition 2 is Rx co-positive cell (FIG. 22 B, D).

% or less after the start of suspension culture That is, it was found that efficient differentiation into a retinal tissue is also achieved, under conditions with or without addition of a Sonic hedgehog signal transduction pathway activating substance in step 2, under conditions including Precondition with a Sonic hedgehog signal transduction pathway activating substance in step 1, addition of a Wnt signal transduction pathway inhibiting substance in step 2 and step 3, reduction of the exogenous Wnt signal transduction pathway inhibiting substance to 3% or less in the course of step 3 (On day 6 after the start of suspension culture), Example 22: Production Example of Retinal Tissue Containing Photoreceptor Precursor Cell and Ganglion Cell from Human iPS Cell Including Precondition with Sonic Hedgehog Signal Transduction Pathway Activating Substance in Step 1 and Use of Wnt Signal Transduction Pathway Inhibiting Substance in Step 2 and Step 3

Human iPS cells (QHJI01s04 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells two days before subconfluence were feeder-free cultured for two days under conditions including addition of SAG (Sonic hedgehog signal transduction pathway activating substance (Shh), 300 nM) (step 1: Precondition (Shh) treatment, FIG. 23) in a Stem Fit (registered trade mark) medium (AK03N; manufactured by Ajinomoto Co., Inc.).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.3 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culture (day 0 after the start of suspension culture, start of step 2), Y27632 (final concentration 20 µM) was added to the above-mentioned serum-free medium, and the cells were cultured in the serum-free medium under the following Condition and Condition 2.

Condition 1
Condition including addition of IWR-1e (3 µM) as a Wnt signal transduction pathway inhibiting substance and no addition of an exogenous Sonic hedgehog signal transduction pathway activating substance to the aforementioned serum-free medium at the start of step 2 (FIG. 23A-D).

Condition 2
Condition including addition of IWR-1e (3 µM) as a Wnt signal transduction pathway inhibiting substance and addition of SAG (10 nM) as an exogenous Sonic hedgehog signal transduction pathway activating substance to the aforementioned serum-free medium at the start of step 2 (FIG. 23E-H).

A cell aggregate was formed by day 2 after the start of suspension culture under Condition 1 and Condition 2 (step 2 completed, and step 3 started).

On day 3 after the start of suspension culture, under Condition 1 and Condition 2, a medium not containing Y27632 or SAG, containing human recombinant BMP4 (manufactured by R&D) and further containing IWR-1e was added by 50 µl such that a final concentration of exogenous human recombinant BMP4 would be 1.5 nM (55 ng/ml) and the concentration (3 µM) of exogenous IWR-1e would not change.

On day 6 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 11 after the start of suspension culture were subjected to bright field observation using an inverted microscope (manufactured by Nikon Corporation, ECLIPSE Ti). As a result, it was found that a neural tissue was formed under Condition 1 and Condition 2.

A part of the aggregates on day 11 after the start of the aforementioned suspension culture was extracted and fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig), which is one of retinal tissue markers. These stained sections were observed with an inverted fluorescence microscope (manufactured by KEYENCE CORPORATION, BIOR-EVO).

As a result, it was found that a neural tissue was formed under Condition 1 and Condition 2. In Condition 1, the proportion of the Chx10 positive retinal tissue was about 90% (FIG. 23A), and in Condition B, the proportion of the Chx10 positive retinal tissue was about 90% (FIG. 23E).

Figure 23:
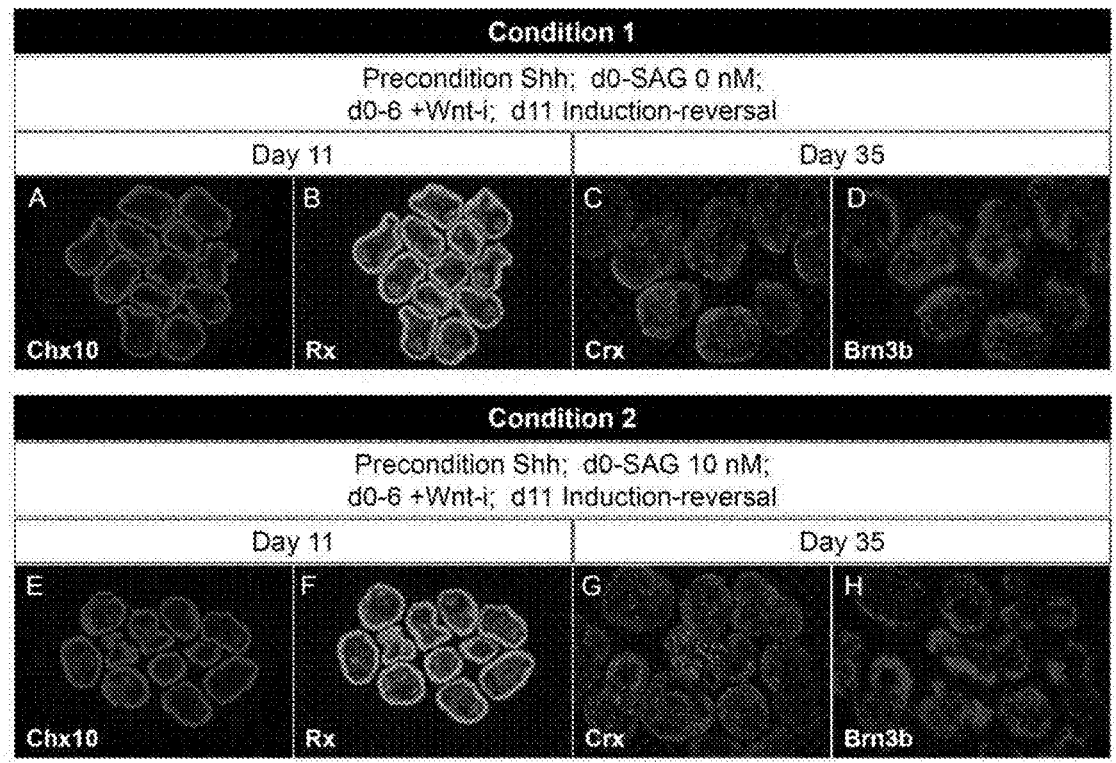
FIG. 23 shows the comparison results of expression of Chx10, Rx, Crx, and Brn3b in cell aggregates formed from human iPS cells under various culture conditions by immunohistostaining.

From the analysis of serial sections, it was found that the Chx10 positive cell in Condition 1 and Condition 2 is Rx co-positive cell (FIG. 23 B, F).

Under Condition 1 and Condition 2, a part of the cells on day 11 after the start of the aforementioned suspension culture was extracted and subjected to a differentiation culture according to the method described in "Nature Communications 6, 6286 (2015)".

The cell aggregate on day 11 after the start of suspension culture were transferred to a 90 mm low adhesive culture dish (manufactured by SUMITOMO BAKELITE CO., LTD.) and cultured in a serum-free medium (DMEM/F12 medium added with 1% N2 supplement) containing a Wnt signal transduction pathway activating substance (CHIR99021, 3 µM) and an FGF signal transduction pathway inhibiting substance (SU5402, 5 µM) at 37° C., 5% $CO_2$ for 3 days, i.e., up to day 14 after the start of suspension culture. During this period, about 50 aggregates were cultured in suspension in a 10 ml serum-free medium containing the aforementioned CHIR99021 and SU5402 per one 90-mm low adhesive culture dish. On day 14 after the start of suspension culture, a thin neuroepithelium was formed, and a retinal pigment epithelial (RPE)-like tissue was formed.

The cell aggregate on day 14 after the start of suspension culture were cultured in suspension in a 90-mm low adhesive culture dish (manufactured by SUMITOMO BAKELITE CO., LTD.) in a serum-containing medium (DMEM/F12 medium added with 10% fetal calf serum, 1% N2 supplement and 100 µM taurine) not containing a Wnt signal transduction pathway activating substance or an FGF signal transduction pathway inhibiting substance at 37° C., 5% $CO_2$, atmospheric oxygen concentration (about 20%) up to day 35 after the start of suspension culture (21 days). From day 20 after the start of suspension culture to the completion of the suspension culture, once every 2-4 days, a half-medium exchange operation was performed once every 2-4 days with the aforementioned serum-containing medium. During this period, about 30 aggregates per one 90-mm low adhesive culture dish were cultured in suspension in 15 ml of the aforementioned serum-containing medium.

The cell aggregates on day 35 after the start of suspension culture were subjected to bright field observation using an inverted microscope (manufactured by Nikon Corporation, ECLIPSE Ti). As a result, it was found that a neural retina-like tissue was present and a neural tissue having a continuous epithelial structure can be formed.

The thus-prepared cell aggregates on day 35 after the start of suspension culture were each fixed with 4% para-formaldehyde, and cryosections were prepared. These cryosections were immunostained for Crx (anti-Crx antibody, manufactured by Takara, rabbit), which is one of the photoreceptor precursor cell markers or Brn3b (anti-Brn3b antibody, manufactured by Santa Cruz, goat), which is one of the ganglion cell markers, and observed using an inverted fluorescence microscope (manufactured by KEYENCE CORPORATION, BIOREVO).

As a result, it was found that about 90% of retinal tissues containing Crx positive photoreceptor precursor cells were formed in the aforementioned cell aggregates on day 35 after the start of suspension culture under Condition 1 and Condition 2 (FIG. 23 C, G). From the analysis of serial sections, it was found that the retinal tissue contained Brn3b positive ganglion cells (FIG. 23 D, H).

From these results, it was found that feeder-free cultured human iPS cells as the starting material also efficiently differentiate into a retinal tissue under conditions with or without addition of a Sonic hedgehog signal transduction pathway activating substance in step 2 on the conditions including a Precondition treatment with a Sonic hedgehog signal transduction pathway activating substance in step 1 and addition of a Wnt signal transduction pathway inhibiting substance in step 2 and step 3. It was further found that retinal cells (or retina specific nerve cells), for example, photoreceptor precursor cell and ganglion cell can be produced by continuing differentiation culture of the prepared retinal tissues. In addition, it was found that photoreceptor precursor cells and ganglion cell form a continuous epithelial structure having a layer structure in the aforementioned retinal tissues.

Example 23: Production Example of Retinal Tissue Using Human iPS Cell Established Using Sendaivirus Vector as Starting Material and Including Precondition in Step 1 and Use of Wnt Signal Transduction Pathway Inhibiting Substance in Step 2

Human iPS cells (TFH-HA strain, established by Sumitomo Dainippon Pharma Co., Ltd.) were established as follows. They were established using peripheral blood mononuclear cells (PBMC) prepared by a well-known method as the starting material, commercially available Sendaivirus vector (4 factors of Oct3/4, Sox2, KLF4, L-Myc, CytoTune kit manufactured by ID Pharma Co., Ltd.), and StemFit (registered trade mark) medium (AK03N; manufactured by Ajinomoto Co., Inc.), Laminin511-E8 (manufactured by Nippi, Inc.).

Human iPS cells (TFH-HA strain) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 μM) and SAG (Sonic hedgehog signal transduction pathway activating substance (Shh), 300 nM) (step 1: Precondition (TGFβR-i+Shh) treatment, FIG. 24 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.3 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium, and the cells were cultured in a serum-free medium under two conditions of the following Conditions 1 and 2.

Condition 1
Condition including addition of IWR-1e (3 μM) as a Wnt signal transduction pathway inhibiting substance and no addition of an exogenous Sonic hedgehog signal transduction pathway activating substance to the aforementioned serum-free medium at the start of step 2 (FIG. 24A, B, "Condition 1").

Condition 2
Condition including addition of IWR-1e (3 μM) as a Wnt signal transduction pathway inhibiting substance and addition of SAG (10 nM) as an exogenous Sonic hedgehog signal transduction pathway activating substance to the aforementioned serum-free medium at the start of step 2 (FIG. 24E, F "Condition 2").

By day 2 after the start of suspension culture, cell aggregates were formed under Condition 1 and Condition 2 (step 2 completed, and step 3 started).

On day 3 after the start of suspension culture, a medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration of exogenous IWR-1e (3 μM) would not change. Thereafter, a half-medium exchange operation was performed once every 2-4 days with the aforementioned serum-free medium not containing Y27632, SAG, human recombinant BMP4 and further containing IWR-1e to avoid change of the concentration of exogenous IWR-1e.

On day 12 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 9 after the start of suspension culture were subjected to bright field observation using an inverted microscope (manufactured by Nikon Corporation, ECLIPSE Ti). As a result, it was found that a neural tissue was formed under Condition 1 and Condition 2.

Figure 24:
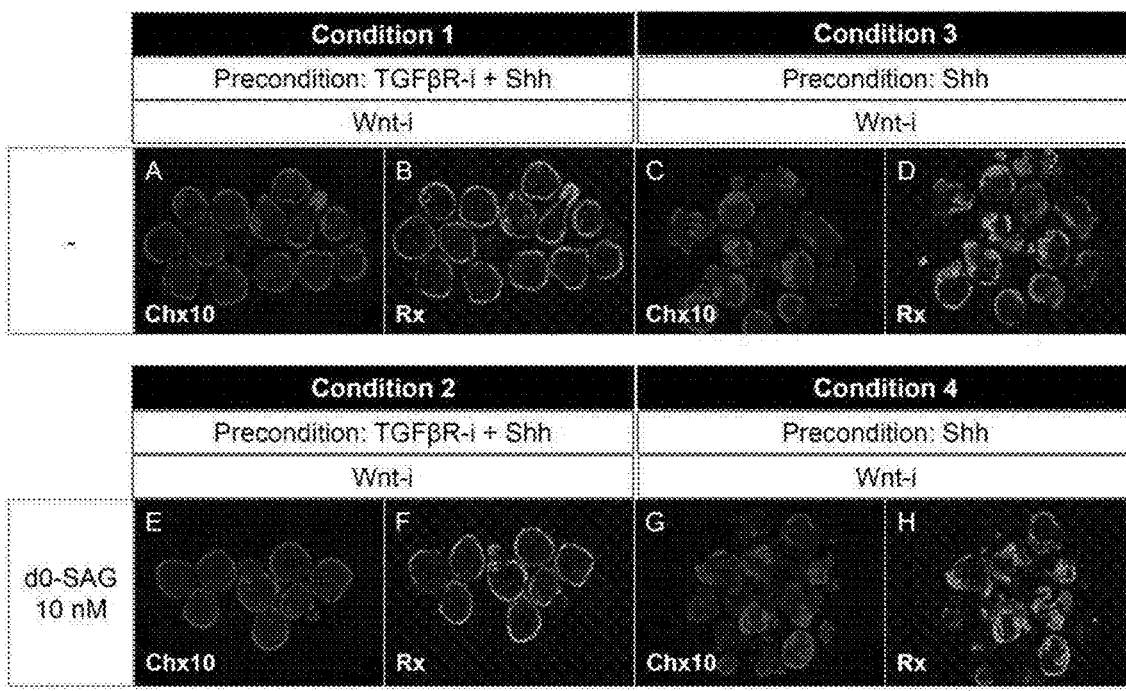
FIG. 24 shows the comparison results of expression of Chx10 and Rx in cell aggregates formed from human iPS cells under various culture conditions by immunohistostaining.

Cell aggregates on day 19 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These stained sections were observed with an inverted fluorescence microscope (manufactured by KEYENCE CORPORATION, BIOREVO) (FIG. 24).

As a result, it was found that a neural tissue could be formed in Condition 1and Condition 2. In Condition 1, the proportion of the Chx10 positive retinal tissue was about 90% (FIG. 24A), and in Condition 2, the proportion of the Chx10 positive retinal tissue was about 90% (FIG. 24E). From the analysis of serial sections, it could be confirmed that these Chx10 positive cells are Rx co-positive cells (FIG. 24B, F).

That is, using human iPS cells established using Sendaivirus vector as the starting material in Condition 1, it was found that efficient differentiation into a retinal tissue is also achieved under conditions including Precondition with a TGFβ signal transduction pathway inhibiting substance and a Sonic hedgehog signal transduction pathway activating substance in step 1, no addition of a Sonic hedgehog signal transduction pathway activating substance in step 2, addition of a Wnt signal transduction pathway inhibiting substance in step 2 and step 3, and reduction of the concentration of the exogenous Wnt signal transduction pathway inhibiting substance to 3% or less in the course of step 3 (on day 12 after the start of suspension culture). Furthermore, using human iPS cells established using Sendaivirus vector as the starting material in Condition 2, it was found that efficient differentiation into retinal cell is also achieved under conditions including Precondition with a TGFβ signal transduction pathway inhibiting substance and a Sonic hedgehog signal transduction pathway activating substance in step 1, addition of a Sonic hedgehog signal transduction pathway activating substance in step 2, and addition of a Wnt signal transduction pathway inhibiting substance in step 2 and step 3.

Example 24: Production Example of Retinal Tissue Using Human iPS Cell Established Using Sendaivirus Vector as Starting Material and Including Precondition in Step 1 and Use of Wnt Signal Transduction Pathway Inhibiting Substance in Step 2

Human iPS cells (TFH-HA strain, established by Sumitomo Dainippon Pharma Co., Ltd.) were established as describe in Example 23. Human iPS cells were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells 2 days before subconfluence were feeder-free cultured for two days under conditions including addition of SAG (Sonic hedgehog signal transduction pathway activating substance (Shh), 300 nM) (FIG. 24 "Precondition: Shh") in a Stem Fit (registered trade mark) medium (AK03N; manufactured by Ajinomoto Co., Inc.).

The thus-prepared Precondition (Shh)-treated human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.3 \times 10^4$ cells per well of a non-cell-adhesive 96-well culture plate (PrimeSurface 96V-bottom plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium, and the cells were cultured in a serum-free medium under two conditions of the following Conditions 3 and 4.

Condition 3

Condition including addition of IWR-1e (3 μM) as a Wnt signal transduction pathway inhibiting substance and no addition of an exogenous Sonic hedgehog signal transduction pathway activating substance to the aforementioned serum-free medium at the start of step 2 (FIG. 24C, D, "Condition 3").

Condition 4

Condition including addition of IWR-1e (3 μM) as a Wnt signal transduction pathway inhibiting substance and addition of SAG (10 nM) as an exogenous Sonic hedgehog signal transduction pathway activating substance to the aforementioned serum-free medium at the start of step 2 (FIG. 24G, H "Condition 4").

By day 2 after the start of suspension culture, cell aggregates were formed under Condition 3 and Condition 4 (step 2 completed, and step 3 started).

On day 3 after the start of suspension culture, a medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration of exogenous IWR-1e (3 μM) would not change. Thereafter, a half-medium exchange operation was performed once every 2-4 days with the aforementioned serum-free medium not containing Y27632, SAG, human recombinant BMP4 and further containing IWR-1e to avoid change of the concentration of exogenous IWR-1e.

On day 12 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 9 after the start of suspension culture were subjected to bright field observation using an inverted microscope (manufactured by Nikon Corporation, ECLIPSE Ti). As a result, it was found that a neural tissue was formed under Condition 3 and Condition 4.

Cell aggregates on day 19 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig.), which is one of the retinal tissue markers. These stained sections were observed with an inverted fluorescence microscope (manufactured by KEYENCE CORPORATION, BIOREVO) (FIG. 24).

As a result, it was found that a neural tissue could be formed in Condition 3 and Condition 4. In Condition 3, the proportion of the Chx10 positive retinal tissue was about 60% (FIG. 24C), and in Condition 4, the proportion of the Chx10 positive retinal tissue was about 50% (FIG. 24G). From the analysis of serial sections, it could be confirmed that these Chx10 positive cells are Rx co-positive cells (FIG. 24D, H).

That is, using human iPS cells established using Sendaivirus vector as the starting material in Condition 3, it was found that efficient differentiation into a retinal tissue is also achieved under conditions including Precondition with a Sonic hedgehog signal transduction pathway activating substance in step 1, no addition of a Sonic hedgehog signal transduction pathway activating substance in step 2, addition of a Wnt signal transduction pathway inhibiting substance in step 2 and step 3, and reduction of the concentration of the exogenous Wnt signal transduction pathway inhibiting substance to 3% or less in the course of step 3 (on day 12 after the start of suspension culture). Furthermore, using human iPS cells established using Sendaivirus vector as the starting material in Condition 4, it was found that efficient differentiation into retinal cell is also achieved under conditions including Precondition with a Sonic hedgehog signal transduction pathway activating substance in step 1, addition of a Sonic hedgehog signal transduction pathway activating substance in step 2, addition of a Wnt signal transduction pathway inhibiting substance in step 2 and step 3, and reduction of the concentration of the exogenous Wnt signal transduction pathway inhibiting substance to 3% or less in the course of step 3.

Example 25: Production Example of Retinal Tissue from Human iPS Cell Including Precondition with TGFβ Signal Transduction Pathway Inhibiting Substance and Sonic Hedgehog Signal Transduction Pathway Activating Substance in Step 1 and Use of Wnt Signal Transduction Pathway Inhibiting Substance in Step 2 and Step 3

Human iPS cells (1231A3 strain, obtained from Kyoto University) were cultured feeder free according to the method described in Example 1 and using StemFit (registered trade mark) medium (AK03N, manufactured by Ajinomoto Co., Inc.) as a feeder-free medium and Laminin 511-E8 (manufactured by Nippi, Inc.) as a feeder-free scaffold.

The feeder-free cultured human iPS cells one day before subconfluence were feeder-free cultured for one day under conditions including addition of SB431542 (TGFβ signal transduction pathway inhibiting substance (TGFβR-i), 5 μM) and SAG (Sonic hedgehog signal transduction pathway activating substance (Shh), 300 nM) (step 1: Precondition (TGFβR-i+Shh) treatment, FIG. 25 "Precondition: TGFβR-i+Shh") in a Stem Fit (registered trade mark) medium (AK03N; manufactured by Ajinomoto Co., Inc.).

The thus-prepared Precondition (TGFβR-i+Shh)-treated human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.3 \times 10^4$ cells per well of a non-cell-adhesive 96-well culture plate (PrimeSurface 96 slit well plate, manufactured by SUMITOMO BAKELITE). Thereafter, the cells were subjected to suspension culture at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culture (day 0 after the start of suspension culture, start of step 2), Y27632 (final concentration 20 μM) was added to the above-mentioned serum-free medium and the cells were cultured in a serum-free medium under the following Condition 2.

Condition 2

Condition including addition of IWR-1e (3 μM) as a Wnt signal transduction pathway inhibiting substance and addition of SAG (10 nM) as an exogenous Sonic hedgehog signal transduction pathway activating substance to the aforementioned serum-free medium at the start of step 2

A cell aggregate was formed by day 2 after the start of suspension culture (step 2 completed, and step 3 started).

On day 4 after the start of suspension culture, a medium not containing Y27632 or SAG, containing human recombinant BMP4 (manufactured by R&D) and further containing IWR-1e was added by 50 μl such that a final concentration of exogenous human recombinant BMP4 would be 1.5 nM (55 ng/ml) and the concentration (3 μM) of exogenous IWR-1e would not change. Thereafter, a half-medium exchange operation was performed once every 2-4 days with the serum-free medium not containing Y27632, SAG, human recombinant BMP4 and further containing IWR-1e to avoid change of the concentration of exogenous IWR-1e.

On day 10 after the start of suspension culture, a 80% medium exchange operation was performed 3 times by using the aforementioned serum-free medium so that the concentration of exogenous IWR-1e would be 3% or less as compared to that before medium exchange. Thereafter, a half-medium exchange operation was performed once every 2-4 days with the aforementioned serum-free medium not containing Y27632, SAG, human recombinant BMP4 and IWR-1e.

The thus-prepared cells on day 17 after the start of suspension culture were subjected to bright field observation using an inverted microscope (manufactured by Nikon Corporation, ECLIPSE Ti). As a result, it was found that a neural tissue was formed.

Figure 25:
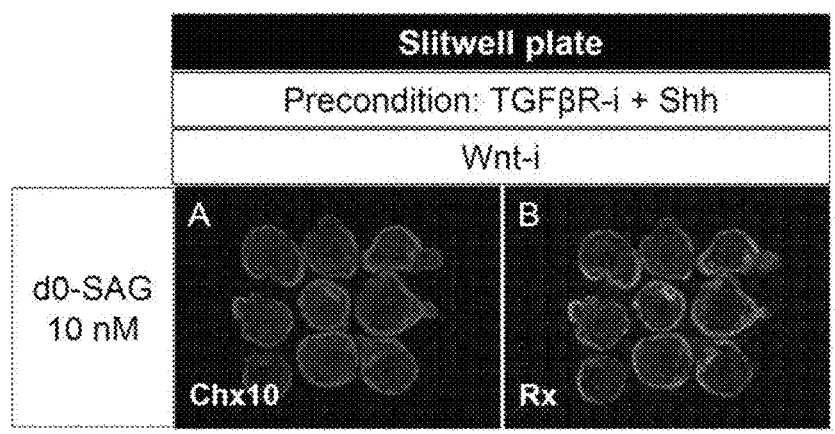
FIG. 25 shows the comparison results of expression of Chx10 and Rx in cell aggregates formed from human iPS cells by immunohistostaining.

The aggregates on day 17 after the start of the aforementioned suspension culture were fixed with 4% para-formaldehyde to produce cryosections. These cryosections were immunostained for Chx10 (anti-Chx10 antibody, Exalpha, sheep), which is one of the retinal tissue markers, or Rx (anti-Rx antibody, Takara, Guinea Pig), which is one of the retinal tissue markers. These stained sections were observed with an inverted fluorescence microscope (manufactured by KEYENCE CORPORATION, BIOREVO) (FIG. 25).

As a result, it was found that a neural tissue could be formed. In this condition, the proportion of the Chx10 positive retinal tissue was about 90% (FIG. 25A). From the analysis of serial sections, it could be confirmed that these Chx10 positive cells are Rx co-positive cells (FIG. 25, B).

That is, it was found that efficient differentiation into retinal cell is also achieved under conditions including Precondition with a TGFβ signal transduction pathway inhibiting substance and a Sonic hedgehog signal transduction pathway activating substance in step 1, addition of a Sonic hedgehog signal transduction pathway activating substance and seeding into a slit well plate in step 2, and addition of a Wnt signal transduction pathway inhibiting substance in step 2 and step 3.

INDUSTRIAL APPLICABILITY

According to the present invention, retinal cells or retinal tissues, and cell aggregates used to produce these can be produced with high efficiency from pluripotent stem cells cultured in the absence of feeder cells.

The contents disclosed in any publication stated in the present specification, including patents, patent applications and scientific literatures, are hereby incorporated in their entireties by reference, to the extent that they have been disclosed herein.

This application is based on a patent application No. 2016-086602 filed in Japan (filing date: Apr. 22, 2016), the contents of which are incorporated in full herein.

The invention claimed is:

1. A method for producing retinal progenitor cells comprising the following steps (a)-(c):
    (a) a first step of culturing pluripotent stem cells in the absence of feeder cells in a medium containing (1) a TGFβ family signal transduction pathway inhibiting substance and/or a Sonic hedgehog signal transduction pathway activating substance, and (2) a factor for maintaining undifferentiated state, wherein at least 60% of the cells obtained in the first step are Oct3/4 positive stem cells,
    (b) a second step of dispersing the cells obtained in the first step and culturing the dispersed cells in suspension in a medium containing a Wnt signal transduction pathway inhibiting substance to form a cell aggregate, and (c) a third step of culturing the aggregate obtained in the second step in suspension in the presence or absence of a Wnt signal transduction pathway inhibiting substance in a medium containing a BMP signal transduction pathway activating substance until retinal progenitor cells appear to obtain an aggregate containing retinal progenitor cells, wherein the TGFβ family signal transduction pathway inhibiting substance is selected from the group consisting of Lefty, SB431542, A-83-01, LDN193189, and Dorsomorphin, wherein the Sonic hedgehog signal transduction pathway activating substance is selected from the group consisting of Shh, SAG, and Purmorphamine, wherein the Wnt signal transduction pathway inhibiting substance is selected from the group consisting of CKI-7, D4476, IWR-1-endo, and IWP-2, and wherein the BMP signal transduction pathway activating substance is selected from the group consisting of BMP2, BMP4, BMP7, and GDF7.

2. The production method according to claim 1, wherein the pluripotent stem cells are cultured for 0.5 hr-144 hr in the first step.

3. The production method according to claim 1, wherein the culturing in the first step is performed by adhesion culture.

4. The production method according to claim 1, wherein the factor for maintaining undifferentiated state is one or more proteins selected from the group consisting of bFGF, FGF4, FGF8, EGF, Nodal, Activin A, Activin B, TGFβ31, and TGFβ132.

5. The production method according to claim 4, wherein the factor for maintaining the undifferentiated state is bFGF.

6. The production method according to claim 1, wherein the medium used for suspension culture in the second step further comprises a Sonic hedgehog signal transduction pathway activating substance selected from the group consisting of Shh, SAG, and Purmorphamine.

7. The production method according to claim 6, wherein the pluripotent stem cells are human pluripotent stem cells and, in the second step, the concentration of the Sonic hedgehog signal transduction pathway activating substance in the medium is a concentration corresponding to Sonic hedgehog signal transduction activity of SAG at 10 nM to 700 nM.

8. The production method according to claim 1, wherein the TGFβ family signal transduction pathway inhibiting substance is one or more substances selected from the group consisting of Lefty, SB431542, A-83-01 and LDN193189.

9. The production method according to claim 1, wherein, in the third step, the BMP signal transduction pathway activating substance is added to the medium between day 1 and day 9 from the start of the second step.

10. The production method according to claim 9, wherein, in the third step, the BMP signal transduction pathway activating substance is added to the medium between day 1 and day 6 from the start of the second step.

11. The production method according to claim 10, wherein, in the third step, the BMP signal transduction pathway activating substance is added to the medium between day 1 and day 3 from the start of the second step.

12. The production method according to claim 1, wherein the BMP signal transduction pathway activating substance is BMP4.

13. The production method according to claim 1, wherein, in the third step, the concentration of the Sonic hedgehog signal transduction pathway activating substance in the medium is not more than a concentration corresponding to Sonic hedgehog signal transduction activity of SAG at 700 nM.

14. The production method according to claim 1, wherein the culturing is performed in a medium containing a Wnt signal transduction pathway inhibiting substance for 3 days to for 18 days from the start of the second step.

15. The production method according to claim 1, wherein the culturing is performed in a medium containing a Wnt signal transduction pathway inhibiting substance for 10 days from the start of the second step.

16. The production method according to claim 1, wherein the Wnt signal transduction pathway inhibiting substance is IWR-1-endo.

17. The production method according to claim 1, wherein the pluripotent stem cells are human pluripotent stem cells.

18. The production method according to claim 1, wherein the pluripotent stem cells are induced pluripotent stem cells.

19. The production method according to claim 1, wherein a uniformed aggregate is formed in the second step.

20. The production method according to claim 1, wherein the suspension culture is performed in the absence of a basement membrane preparation.

21. A method for producing an aggregate comprising one or more cells selected from the group consisting of neural retinal progenitor cells, photoreceptor cells, rod photoreceptor cells, cone photoreceptor cells, horizontal cells, bipolar cells, amacrine cells, retinal ganglion cells, and retinal pigment epithelial cells comprising the following steps (a) and (b):

(a) producing an aggregate comprising retinal progenitor cells by the method of claim 1, and (b) suspension culturing of the aggregate obtained in step (a).

22. A method for producing a retinal tissue comprising the following steps (i) and (ii):

(i) producing an aggregate comprising one or more cells selected from the group consisting of neural retinal progenitor cells, photoreceptor cells, rod photoreceptor cells, cone photoreceptor cells, horizontal cells, bipolar cells, amacrine cells, retinal ganglion cells, and retinal pigment epithelial cells by the method of claim 21; and (ii) cutting out a retinal tissue from the aggregate obtained in step (i).

* * * * *

UNITED STATES PATENT AND TRADEMARK OFFICE
CERTIFICATE OF CORRECTION

PATENT NO. : 11,371,016 B2  
APPLICATION NO. : 16/095339  
DATED : June 28, 2022  
INVENTOR(S) : Kuwahara et al.

Page 1 of 1

It is certified that error appears in the above-identified patent and that said Letters Patent is hereby corrected as shown below:

In the Claims

Claim 4, Column 113, Lines 33-34, "TGFβ31, and TGFβ132" should read "TGFβ1, and TGFβ2."

Signed and Sealed this  
Eleventh Day of October, 2022

Katherine Kelly Vidal  
*Director of the United States Patent and Trademark Office*